(12) United States Patent
Lapina et al.

(10) Patent No.: US 9,884,873 B2
(45) Date of Patent: Feb. 6, 2018

(54) SOLID FORMS OF AN ANTIVIRAL COMPOUND

(71) Applicant: Gilead Pharmasset LLC, Foster City, CA (US)

(72) Inventors: Olga Viktorovna Lapina, Newark, CA (US); Bing Shi, Redwood City, CA (US); Fang Wang, Foster City, CA (US); Scott Alan Wolckenhauer, Redwood City, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

(21) Appl. No.: 15/459,785

(22) Filed: Mar. 15, 2017

(65) Prior Publication Data

US 2017/0247386 A1    Aug. 31, 2017

Related U.S. Application Data

(63) Continuation of application No. 14/733,101, filed on Jun. 8, 2015, now Pat. No. 9,630,972.

(60) Provisional application No. 62/010,919, filed on Jun. 11, 2014.

(51) Int. Cl.
    *C07D 491/052*    (2006.01)

(52) U.S. Cl.
    CPC ...... *C07D 491/052* (2013.01); *C07B 2200/13* (2013.01)

(58) Field of Classification Search
    CPC .................................................. C07D 491/052
    See application file for complete search history.

(56) References Cited

U.S. PATENT DOCUMENTS

| 8,575,135 B2 | 11/2013 | Bacon et al. |
| 8,921,341 B2 | 12/2014 | Bacon et al. |
| 2013/0156732 A1 | 6/2013 | Bacon et al. |
| 2014/0018313 A1 | 1/2014 | Bacon et al. |
| 2014/0309432 A1 | 10/2014 | Bacon et al. |

FOREIGN PATENT DOCUMENTS

| WO | WO-2012/068234 A2 | 5/2012 |
| WO | WO-2013/075029 A1 | 5/2013 |

OTHER PUBLICATIONS

Caira et al. (1998) "Crystalline Polymorphism of Organic Compounds," Topics in Current Chemistry 198. vol. 5: 163-208.
Intl. Search Report dated Aug. 3, 2015 for PCT/US2015/034649.

*Primary Examiner* — Laura L. Stockton
(74) *Attorney, Agent, or Firm* — Sheppard Mullin Richter & Hampton LLP

(57) ABSTRACT

Crystalline solid forms of methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (Compound I) were prepared and characterized in the solid state:

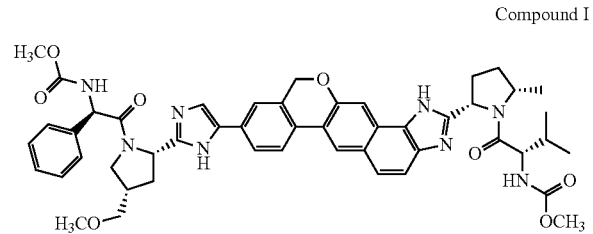

Compound I

Also provided are processes of manufacture and methods of using these crystalline forms.

20 Claims, 54 Drawing Sheets

Compound I bis-HCl Form II (MeOH solvate)   Compound I bis-HCl Form IV (1-propanol solvate)

Compound I bis-HCl Form III (EtOH solvate)   Compound I bis-HCl Form V (EtOH solvate)

SOLID FORMS OF AN ANTIVIRAL COMPOUND

CROSS REFERENCE TO RELATED APPLICATIONS

This application is a Continuation of U.S. patent application Ser. No. 14/733,101 filed Jun. 8, 2015, now U.S. Pat. No. 9,630,972, which claims priority to and the benefit of U.S. Provisional Application No. 62/010,919, filed Jun. 11, 2014, which is hereby incorporated by reference in its entirety.

BACKGROUND

The present disclosure relates generally to crystalline solid forms of the compound methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate, designated herein as Compound I, processes for making these forms, and their therapeutic methods of use.

Hepatitis C is recognized as a chronic viral disease of the liver. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

SUMMARY

Compound I which is known to exhibit antiviral properties can be synthesized according to the methods described in WO 2013/075029. Compound I has the formula:

The present disclosure provides crystalline forms of Compound I and its salts, co-crystals, hydrates, and solvates. Also described herein are processes for making the mesophase and crystalline forms of Compound I and methods for using them in the treatment of hepatitis C.

Thus, one embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (Compound I Form I) characterized by an X-ray powder diffractogram comprising the following peaks: 4.8, 5.2, and 6.0°2θ±0.2°2θ, as determined on a diffractometer using Cu—Kα radiation at a wavelength of 1.5406 Å.

Some embodiments provided herein relate to crystalline forms of the bis-hydrochloride salt of Compound I, methyl {(2S)-1-[(2S,5S)-2-(9-{2-[(2S,5S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride ("Compound I bis-HCl"), having the formula:

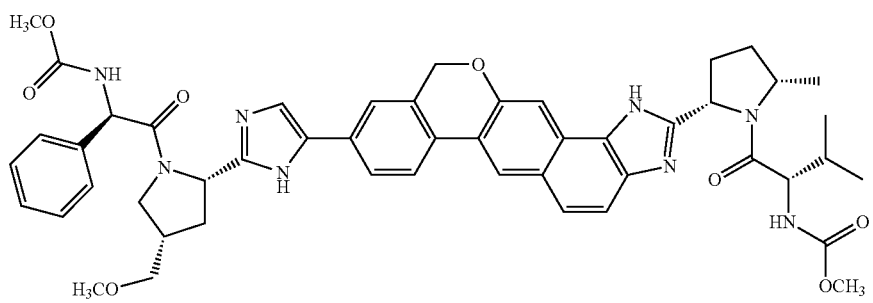

I

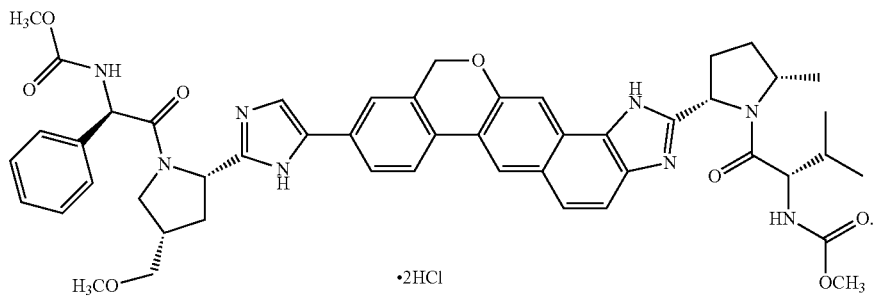

Compound I bis-HCl may provide 5 forms further described herein: Compound I bis-HCl Form II, Compound I bis-HCl Form III, Compound I bis-HCl Form IV, Compound I bis-HCl Form V, and Compound I bis-HCl Form VI.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form II) characterized by an X-ray powder diffractogram comprising the following peaks: 6.1, 7.3, and 9.6°2θ±0.2°2θ, as determined on a diffractometer using Cu—Kα radiation at a wavelength of 1.5406 Å.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form III) characterized by an X-ray powder diffractogram comprising the following peaks: 7.2 and 7.6°2θ±0.2°2θ, as determined on a diffractometer using Cu—Kα radiation at a wavelength of 1.5406 Å.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form IV) characterized by an X-ray powder diffractogram comprising the following peaks: 7.5, 11.2, and 14.5°2θ±0.2°2θ, as determined on a diffractometer using Cu—Kα radiation at a wavelength of 1.5406 Å.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form V) characterized by an X-ray powder diffractogram comprising the following peaks: 7.1, 10.6, and 14.1°2θ±0.2°2θ, as determined on a diffractometer using Cu—Kα radiation at a wavelength of 1.5406 Å.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form VI) characterized by an X-ray powder diffractogram comprising the following peaks: 6.7 and 7.6°2θ±0.2°2θ, as determined on a diffractometer using Cu—Kα radiation at a wavelength of 1.5406 Å.

Some embodiments provided herein relate to crystalline forms of a phosphate complex of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate ("Compound I Phosphate"), having the formula:

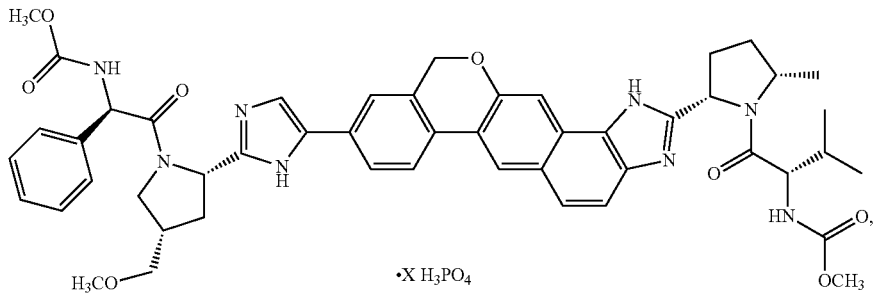 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

wherein X can be between 2 to 3.5. Compound I Phosphate may appear in several forms as further described herein: Compound I Phosphate Form VII, Compound I Phosphate Form VIII, Compound I Phosphate Form IX, Compound I Phosphate Form X, Compound I Phosphate Form XI, Compound I Phosphate Form XII, Compound I Phosphate Form XIII, Compound I Phosphate Form XIV, and Compound I Phosphate Form XV.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]

naphtho[1,2-d]imidazol-2-yl)-5-methylpyrrolidin-1-yl]-3-methyl-1-oxobutan-2-yl}carbamate phosphate (Compound I Phosphate Form VII) characterized by an X-ray powder diffractogram comprising the following peaks: 7.5, 14.6, and 21.6°2θ±0.2°2θ, as determined on a diffractometer using Cu—Kα radiation at a wavelength of 1.5406 Å.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form VIII) characterized by an X-ray powder diffractogram comprising the following peaks: 4.2, 8.3, and 16.0°2θ±0.2°2θ, as determined on a diffractometer using Cu—Kα radiation at a wavelength of 1.5406 Å.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form IX) characterized by an X-ray powder diffractogram comprising the following peaks: 8.4, 16.1, and 16.3°2θ±0.2°2θ, as determined on a diffractometer using Cu—Kα radiation at a wavelength of 1.5406 Å.

Another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form X) characterized by an X-ray powder diffractogram comprising the following peaks: 6.6, 9.5, and 10.6°2θ±0.2°2θ, as determined on a diffractometer using Cu—Kα radiation at a wavelength of 1.5406 Å.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XI) characterized by an X-ray powder diffractogram comprising the following peaks: 8.9, 13.1, and 18.1°2θ±0.2°2θ, as determined on a diffractometer using Cu—Kα radiation at a wavelength of 1.5406 Å.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XII) characterized by an X-ray powder diffractogram comprising the following peaks: 3.8, 7.5, and 16.9°2θ±0.2°2θ, as determined on a diffractometer using Cu—Kα radiation at a wavelength of 1.5406 Å.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XIII) characterized by an X-ray powder diffractogram comprising the following peaks: 4.1, 15.9, and 22.9°2θ±0.2°2θ, as determined on a diffractometer using Cu—Kα radiation at a wavelength of 1.5406 Å.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XIV) characterized by an X-ray powder diffractogram comprising the following peaks: 3.5 and 6.9°2θ±0.2°2θ, as determined on a diffractometer using Cu—Kα radiation at a wavelength of 1.5406 Å.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XV) characterized by an X-ray powder diffractogram comprising the following peaks: 4.0, 23.0, and 24.2°2θ±0.2°2θ, as determined on a diffractometer using Cu—Kα radiation at a wavelength of 1.5406 Å.

Some embodiments provided herein relate to crystalline forms of a L-tartrate complex of Compound I, {(2S)-1-[(2S,5 S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate L-tartrate ("Compound I L-tartrate"), having the following formula:

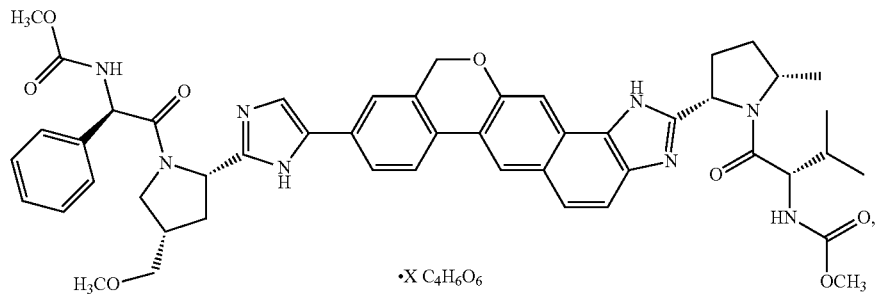

wherein X can be about 2.5 to about 3. In some embodiments, X can be about 2.5 or about 2.9. Compound I L-tartrate may appear in several forms as further described herein: Compound I L-tartrate Form XVI and Compound I L-tartrate Form XVII.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]

naphtho[1,2-d]imidazol-2-yl)-5-methylpyrrolidin-1-yl]-3-methyl-1-oxobutan-2-yl}carbamate L-tartrate (Compound I L-tartrate Form XVI) characterized by an X-ray powder diffractogram comprising the following peaks: 4.1, 8.1, and 15.6°2θ±0.2°2θ, as determined on a diffractometer using Cu—Kα radiation at a wavelength of 1.5406 Å.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate L-tartrate (Compound I L-tartrate Form XVII) characterized by an X-ray powder diffractogram comprising the following peaks: 8.2, 15.8, and 22.6°2θ±0.2°2θ, as determined on a diffractometer using Cu—Kα radiation at a wavelength of 1.5406 Å.

Some embodiments provided herein relate to crystalline forms of a bis-hydrobromide salt of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrobromide ("Compound I bis-HBr"), having the formula:

peaks: 6.7, 7.6, and 18.9°2θ±0.2°2θ, as determined on a diffractometer using Cu—Kα radiation at a wavelength of 1.5406 Å.

One embodiment is a composition comprising any one of Compound I Form I; Compound I bis-HCl Forms II to VI; Compound I Phosphate Forms VII to Form XV; Compound I L-tartrate Forms XVI to XVII; and Compound I bis-HBr Form XVIII.

Additionally, the invention provides in one embodiment a method for treating a subject having HCV. The method comprises administering to the subject a therapeutically effective amount of any one of Compound I Forms I to XVIII, as described generally above.

Another embodiment is the use of any one of Compound I Form I; Compound I bis-HCl Forms II to VI; Compound I Phosphate Forms VII to Form XV; Compound I L-tartrate Forms XVI to XVII; and Compound I bis-HBr Form XVIII for the prophylactic or therapeutic treatment of hepatitis C or a hepatitis C associated disorder.

Still an additional embodiment is the use of any one of Compound I Form I; Compound I bis-HCl Forms II to VI; Compound I Phosphate Forms VII to Form XV; Compound I L-tartrate Forms XVI to XVII; and Compound I bis-HBr

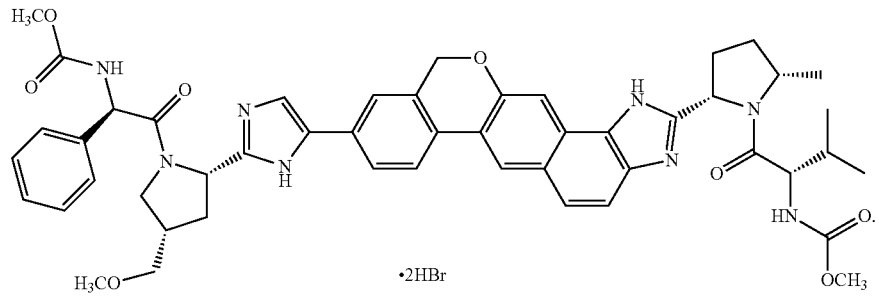 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrobromide (Compound I bis-HBr Form XVIII) characterized by an X-ray powder diffractogram comprising the following Form XVIII in the manufacture of a medicament for treating hepatitis C or a hepatitis C associated disorder in a subject.

Some embodiments provided herein relate to crystalline forms of a D-tartrate complex of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate L-tartrate ("Compound I D-tartrate"), having the following formula:

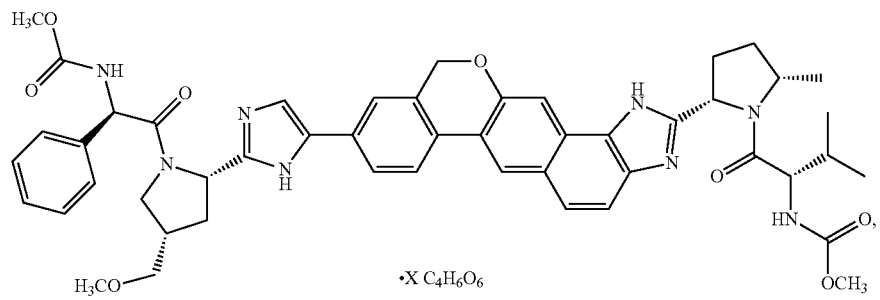

wherein X is in the range of from about 2 to about 4. In some embodiments X is about 2, 2.5, 3.0, 3.5, or 4.0. In other particular embodiments X is about 2.5, 3.0, or 3.5. Compound I D-tartrate may appear in several forms as further described herein: Compound I D-tartrate Form I and Compound I D-tartrate Form II.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate D-tartrate (Compound I D-tartrate Form I) characterized by an X-ray powder diffractogram comprising the following peaks: 4.2, 8.0, and 15.3°2θ±0.2°2θ, as determined on a diffractometer using Cu—Kα radiation at a wavelength of 1.5406 Å.

Yet another embodiment is crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate D-tartrate (Compound I D-tartrate Form II) characterized by an X-ray powder diffractogram comprising the following peaks: 4.2, 8.2, and 15.9°2θ±0.2°2θ, as determined on a diffractometer using Cu—Kα radiation at a wavelength of 1.5406 Å.

DETAILED DESCRIPTION

Figure 1:
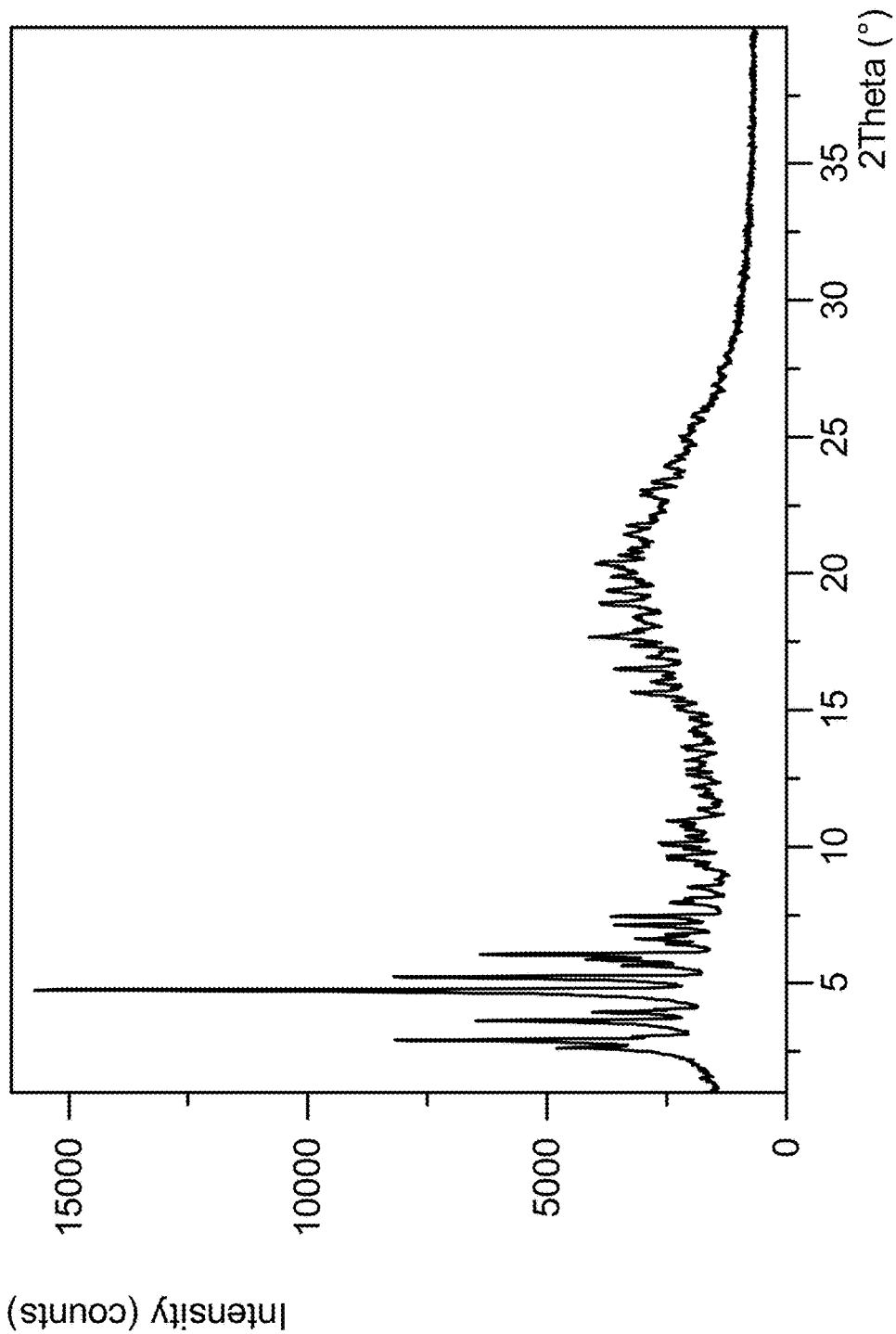
FIG. 1 shows a X-ray powder diffraction (XRPD) of Compound I Form I.

The compound methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate, designated herein as Compound I, has the formula:

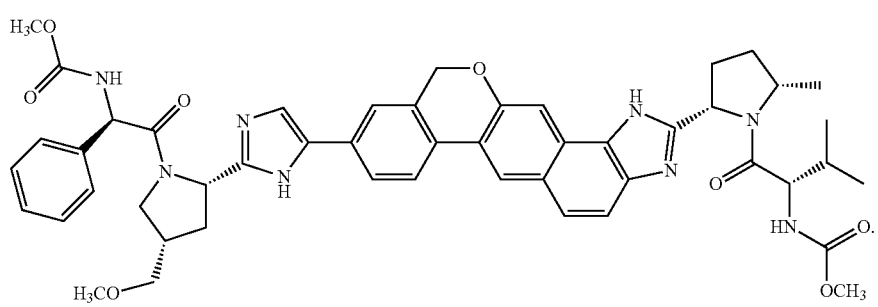 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

The present disclosure relates to the amorphous, mesophase, and crystalline forms of Compound I, and processes for making the mesophase and crystalline forms. Compound I also provides a form further described herein as "Compound I Form I."

Additional crystalline forms of Compound I are also further described herein. The hydrochloride salt of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate hydrochloride ("Compound I HCl"), has the formula:

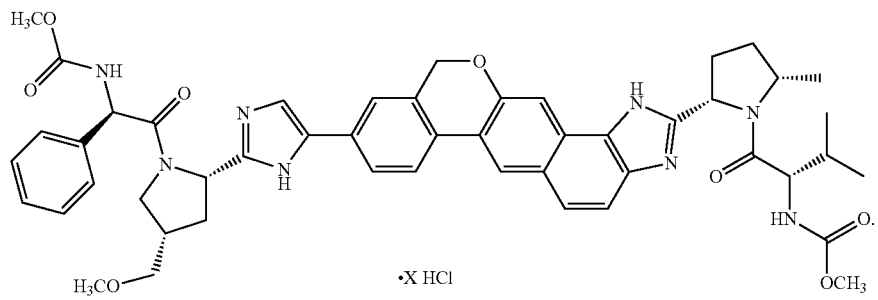 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

In some embodiments, X can be 1 or 2.

The bis-hydrochloride salt of Compound I, {(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride ("Compound I bis-HCl") may provide 5 forms further described herein: Compound I bis-HCl Form II, Compound I bis-HCl Form III, Compound I bis-HCl Form IV, Compound I bis-HCl Form V, and Compound I bis-HCl Form VI.

The phosphate complex of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate ("Compound I Phosphate"), has the formula:

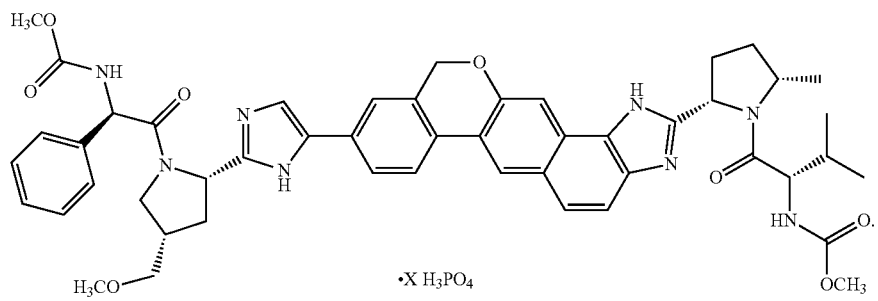 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

In some embodiments, X can be between 2 to 3.5. Compound I Phosphate may appear in several forms as further described herein: Compound I Phosphate Form VII, Compound I Phosphate Form VIII, Compound I Phosphate Form IX, Compound I Phosphate Form X, Compound I Phosphate Form XI, Compound I Phosphate Form XII, Compound I Phosphate Form XIII, Compound I Phosphate Form XIV, and Compound I Phosphate Form XV.

The L-tartrate complex of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate L-tartrate ("Compound I L-tartrate"), has the following formula:

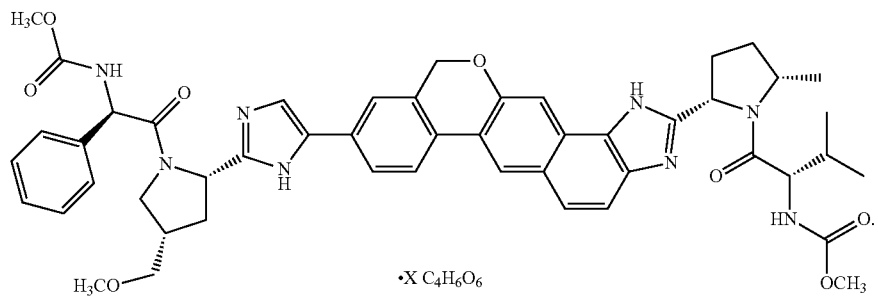 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

In some embodiments, X can be about 2.5. Compound I L-tartrate may appear in several forms as further described herein: Compound I L-tartrate Form XVI and Compound I L-tartrate Form XVII.

The D-tartrate complex of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate D-tartrate ("Compound I D-tartrate"), has the following formula:

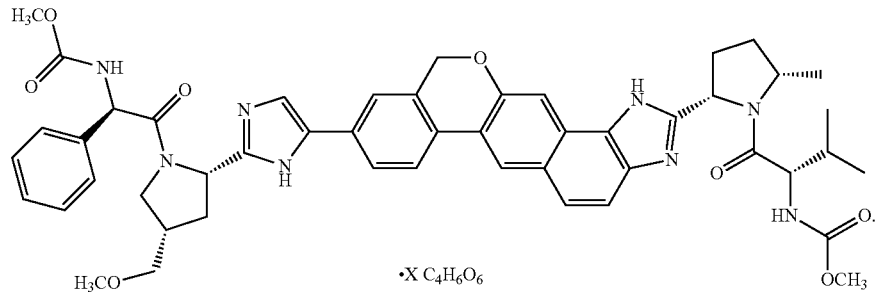

wherein X is in the range of from about 2 to about 4. In some embodiments X is about 2, 2.5, 3.0, 3.5, or 4.0. In other particular embodiments X is about 2.5, 3.0, or 3.5. Compound I D-tartrate may appear in several forms as further described herein: Compound I D-tartrate Form I and Compound I D-tartrate Form II.

The hydrobromide salt of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate hydrobromide ("Compound I HBr"), has the following formula:

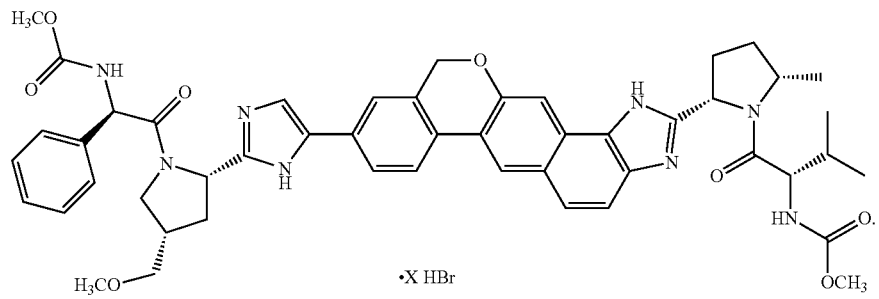 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

In some embodiments, X can be 1 or 2. The bis-hydrobromide salt of Compound I, {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrobromide ("Compound I bis-HBr"), may provide Compound I bis-HBr Form XVIII as further described herein.

Definitions

As used in the present specification, the following words and phrases are generally intended to have the meanings as set forth below, except to the extent that the context in which they are used indicates otherwise.

The term "complex" refers to a formation resulting from the interaction between Compound I and another molecule.

The term "solvate" refers to a complex formed by combining Compound I and a solvent.

The term "co-crystal" refers to a crystalline material formed by combining Compound I, or any Formula disclosed herein and one or more co-crystal formers (i.e., a molecule, ion or atom). In certain instances, co-crystals may have improved properties as compared to the parent form (i.e., the free molecule, zwitterion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

Any formula or structure given herein, including Compound I, is also intended to represent unlabeled forms as well as isotopically labeled forms of the compounds. Isotopically labeled compounds have structures depicted by the formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes Compound I in which from 1 to "n" hydrogens attached to a carbon atom is/are replaced by deuterium, in which n is the number of hydrogens in the molecule. Such compounds exhibit increased resistance to metabolism and are thus useful for increasing the half-life of Compound I when administered to a mammal. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogen atoms have been replaced by deuterium.

Deuterium labeled or substituted compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in Compound I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "therapeutically effective amount" refers to an amount that is sufficient to effect treatment, as defined below, when administered to a mammal in need of such treatment. The therapeutically effective amount will vary depending upon the subject being treated, the weight and age of the subject, the severity of the disease condition, the manner of administration and the like, which can readily be determined by one of ordinary skill in the art.

In addition, abbreviations as used herein have respective meanings as follows:

| | |
|---|---|
| μL | Microliter |
| μm | Micrometer |
| 2-MeTHF | 2-methyl tetrahydrofuran |
| ACN | Acetonitrile |
| API | Active pharmaceutical ingredient |
| BE | Butyl ether |
| BN | Butyronitrile |
| DCM | Dichloromethane |
| DSC | Differential scanning calorimetry |
| DVS | Dynamic vapor sorption |
| eq. | equivalents |
| EtOAc | Ethyl acetate |
| EtOH | Ethanol |
| g | Gram |
| h | Hour |
| IC | Ion chromatography |
| IPA | Isopropanol |
| IPE | Diisopropyl ether |
| IPAc | Isopropyl acetate |
| KF | Karl Fischer titration |
| kV | kilovolts |
| MEK | Methyl ethyl ketone |
| MeOH | Methanol |
| MIBK | Methyl iso-butyl ketone |
| mA | Milliamps |
| mg | Milligram |
| min | Minute |
| mL/ml | Milliliter |
| MTBE | Methyl tert-butyl ether |
| NMR | Nuclear magnetic resonance |
| PLM | Polarized light microscopy |
| RT | Room temperature |
| s | Second |
| TGA | Thermogravimetric analysis |
| THF | Tetrahydrofuran |
| XRPD | X-ray powder diffraction |

Forms of Compound I

As described generally above, the present disclosure provides mesophase and crystalline forms of Compound I and Compound I salts/co-crystals, which are designated as Forms I to XVI.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (Compound I Form I) is characterized by an X-ray powder diffractogram comprising the following peaks: 4.8, 5.2, and 6.0°2θ±0.2°2θ, as determined on a diffractometer using Cu—Kα radiation at a wavelength of 1.5406 Å. The diffractogram comprises additional peaks at 2.9 and 3.6°2θ±0.2°2θ. Compound I Form I is also characterized by its full X-ray powder diffractogram as substantially shown in FIG. 1.

Figure 2:
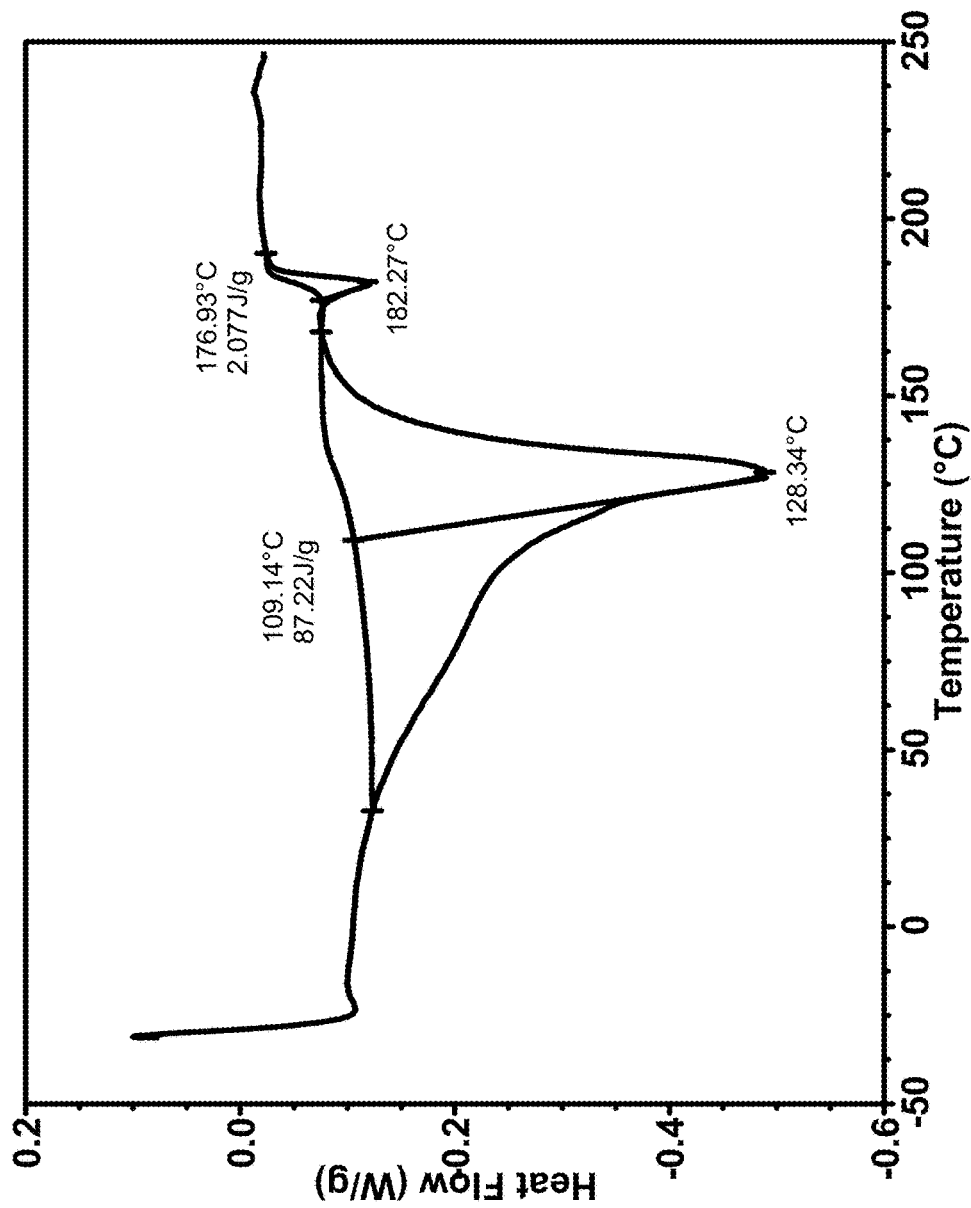
FIG. 2 shows a differential scanning calorimeter (DSC) curve of Compound I Form I.

In some embodiments, Compound I Form I is characterized by its differential scanning calorimetry (DSC) curve that comprises an endotherm at about 109° C. and an endotherm at about 177° C. Compound I Form I also is characterized by its full DSC curve as substantially as shown in FIG. 2.

Figure 4:
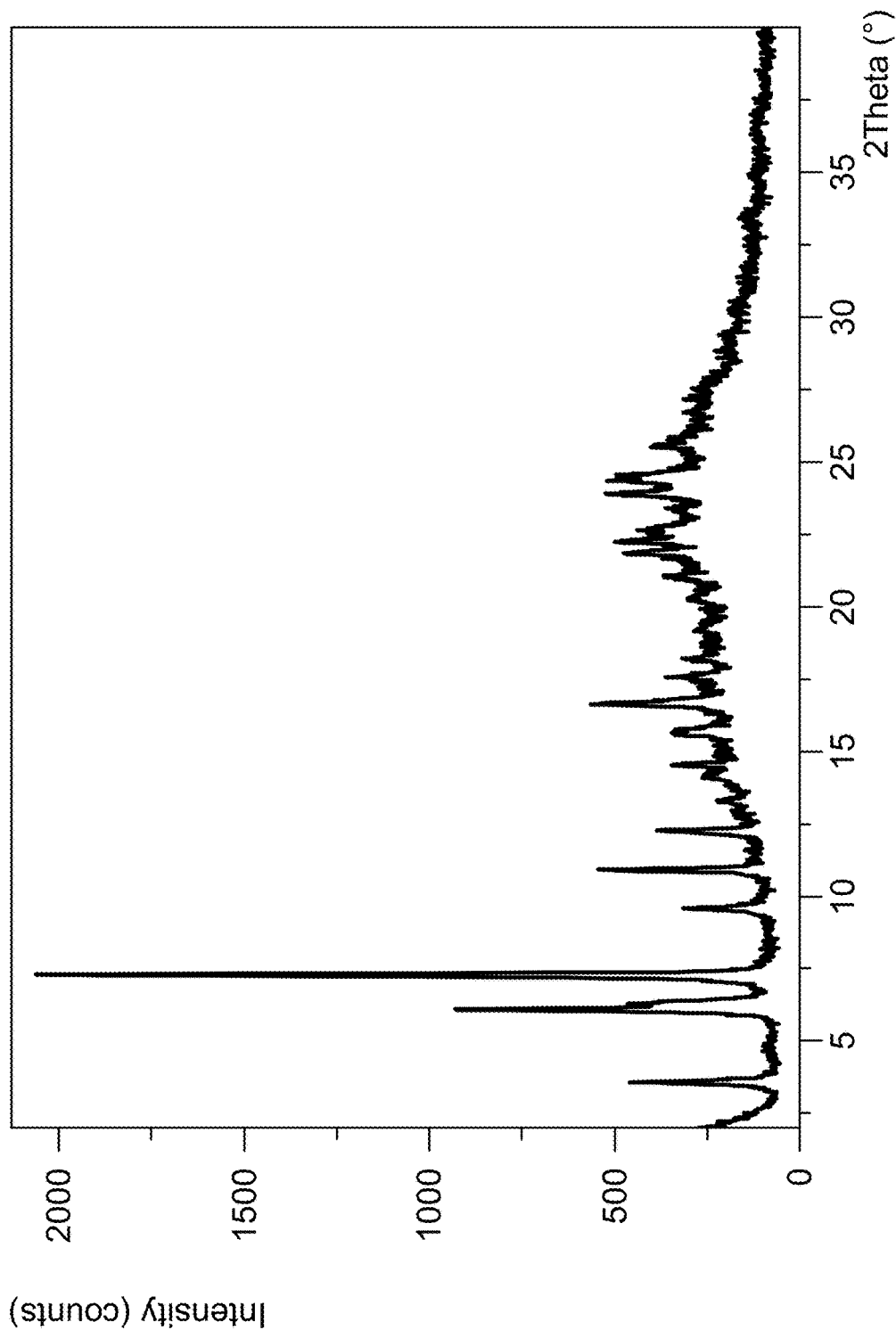
FIG. 4 shows a X-ray powder diffraction (XRPD) of Compound I bis-HCl Form II.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form II) is characterized by an X-ray powder diffractogram comprising the following peaks: 6.1, 7.3, and 9.6°2θ±0.2°2θ, as determined on a diffractometer using Cu—Kα radiation at a wavelength of 1.5406 Å. The diffractogram comprises additional peaks at 3.6 and 10.9°2θ±0.2°2θ. Compound I bis-HCl Form II is also characterized by its full X-ray powder diffractogram as substantially as shown in FIG. 4.

Figure 5:
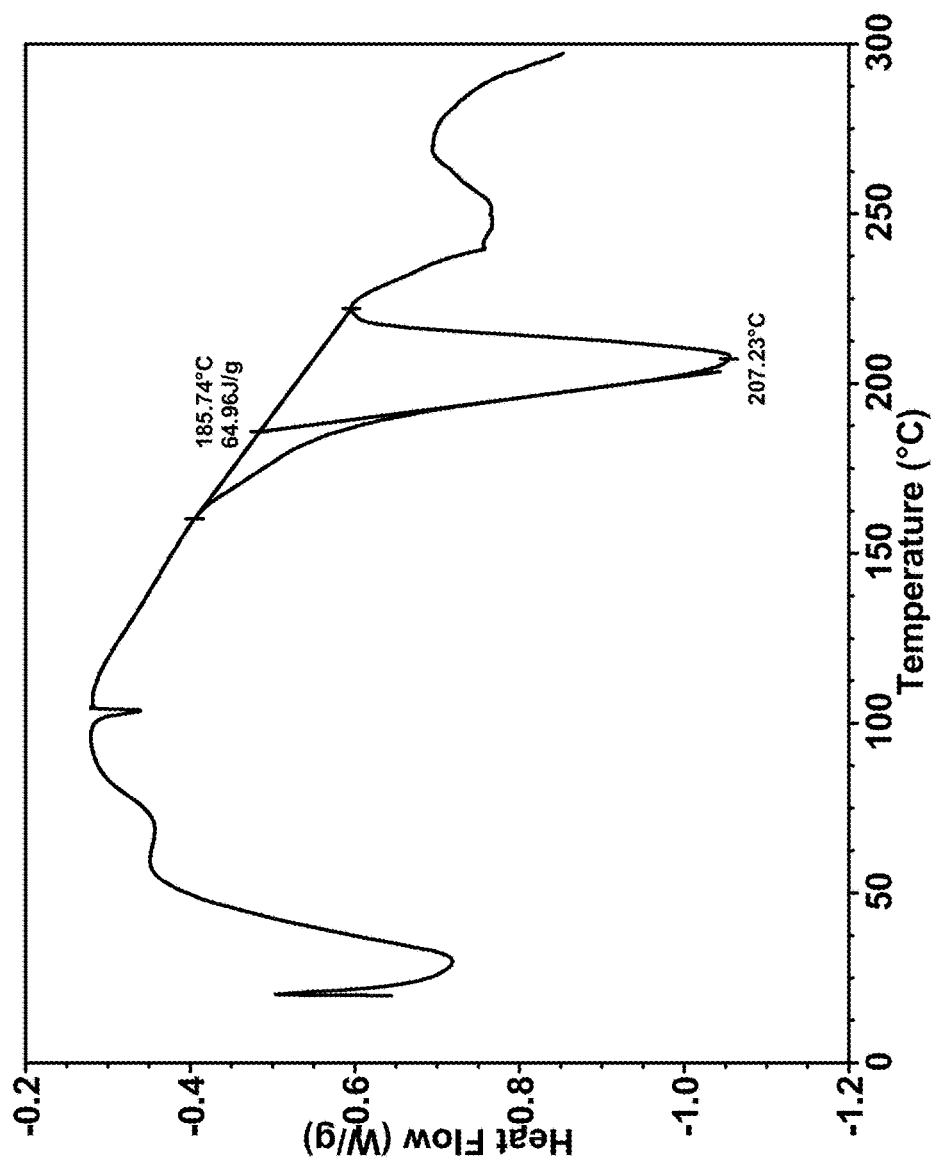
FIG. 5 shows a differential scanning calorimeter (DSC) curve of Compound I bis-HCl Form II.

In some embodiments, Compound I bis-HCl Form II is characterized by its differential scanning calorimetry (DSC) curve that comprises an endotherm at about 186° C. Compound I bis-HCl Form II also is characterized by its full DSC curve as substantially as shown in FIG. 5.

Figure 7:
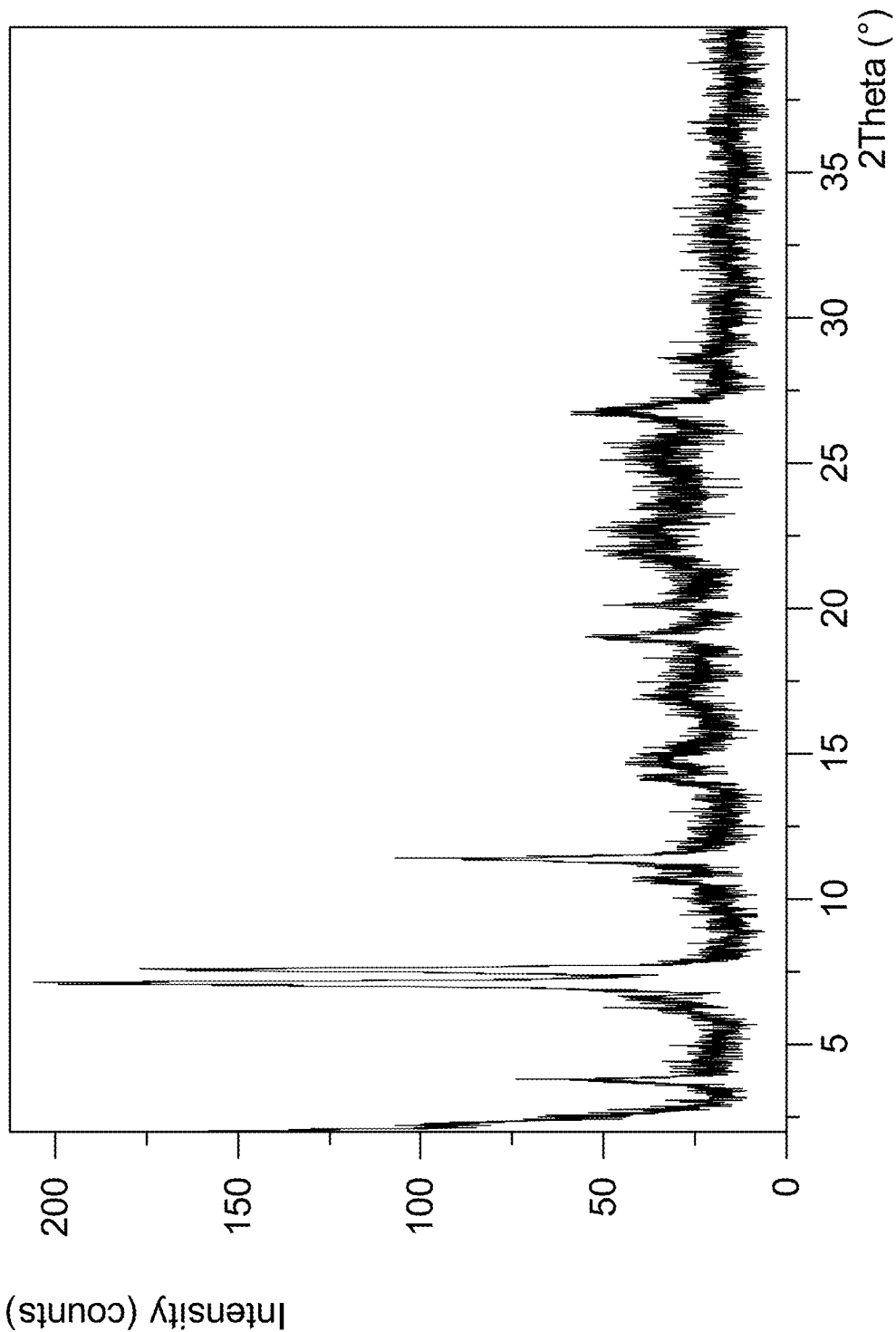
FIG. 7 shows a X-ray powder diffraction (XRPD) of Compound I bis-HCl Form III.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form III) is characterized by an X-ray powder diffractogram comprising the following peaks: 7.2 and 7.6°2θ±0.2°2θ, as determined on a diffractometer using Cu—Kα radiation at a wavelength of 1.5406 Å. The diffractogram comprises additional peaks at 3.8 and 11.4°2θ±0.2°2θ. Compound I bis-HCl Form III is also characterized by its full X-ray powder diffractogram as substantially as shown in FIG. 7.

Figure 8:
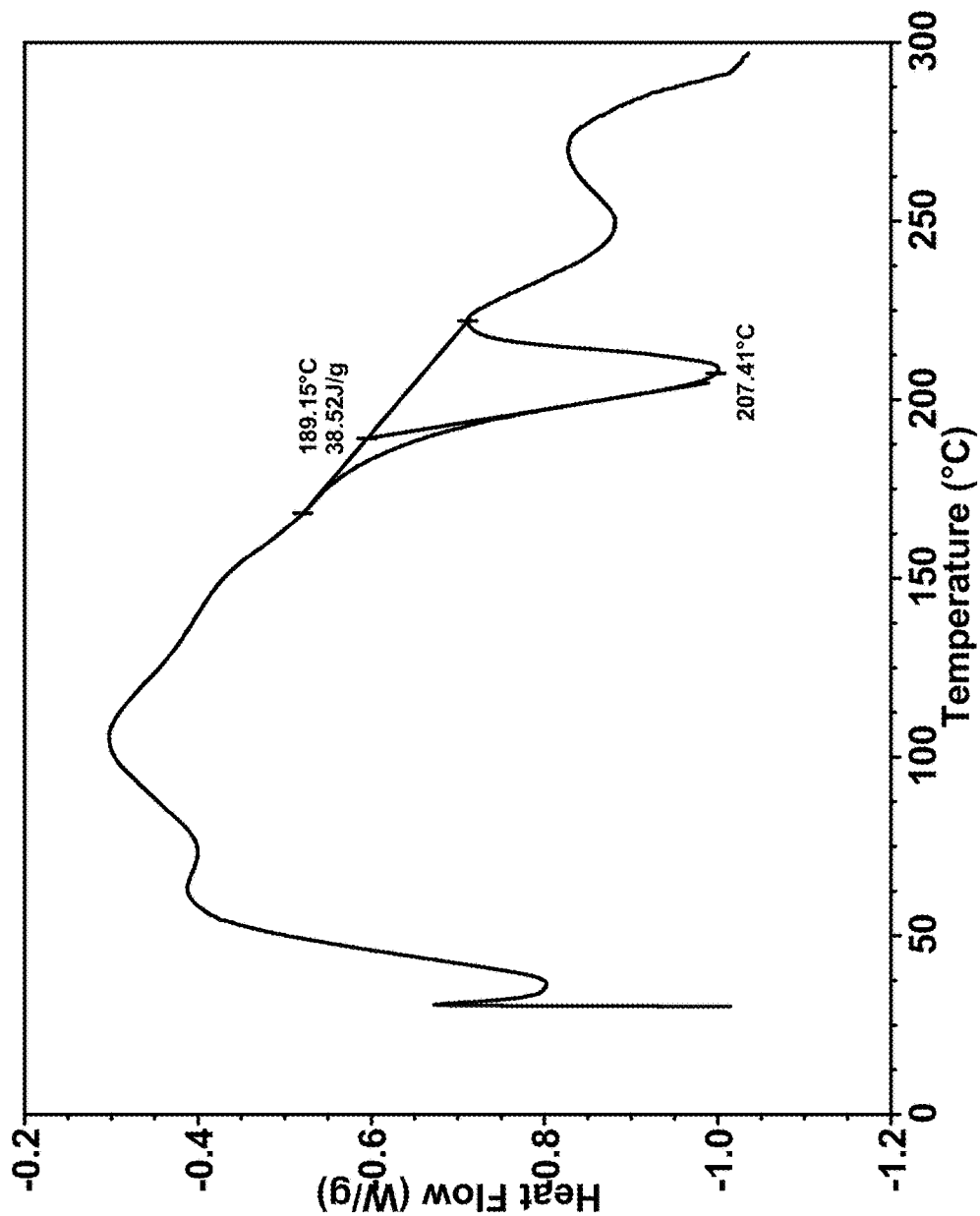
FIG. 8 shows a differential scanning calorimeter (DSC) curve of Compound I bis-HCl Form III.

In some embodiments, Compound I bis-HCl Form III is characterized by its differential scanning calorimetry (DSC) curve that comprises an endotherm at about 189° C. Compound I bis-HCl Form III also is characterized by its full DSC curve as substantially as shown in FIG. 8.

Figure 10:
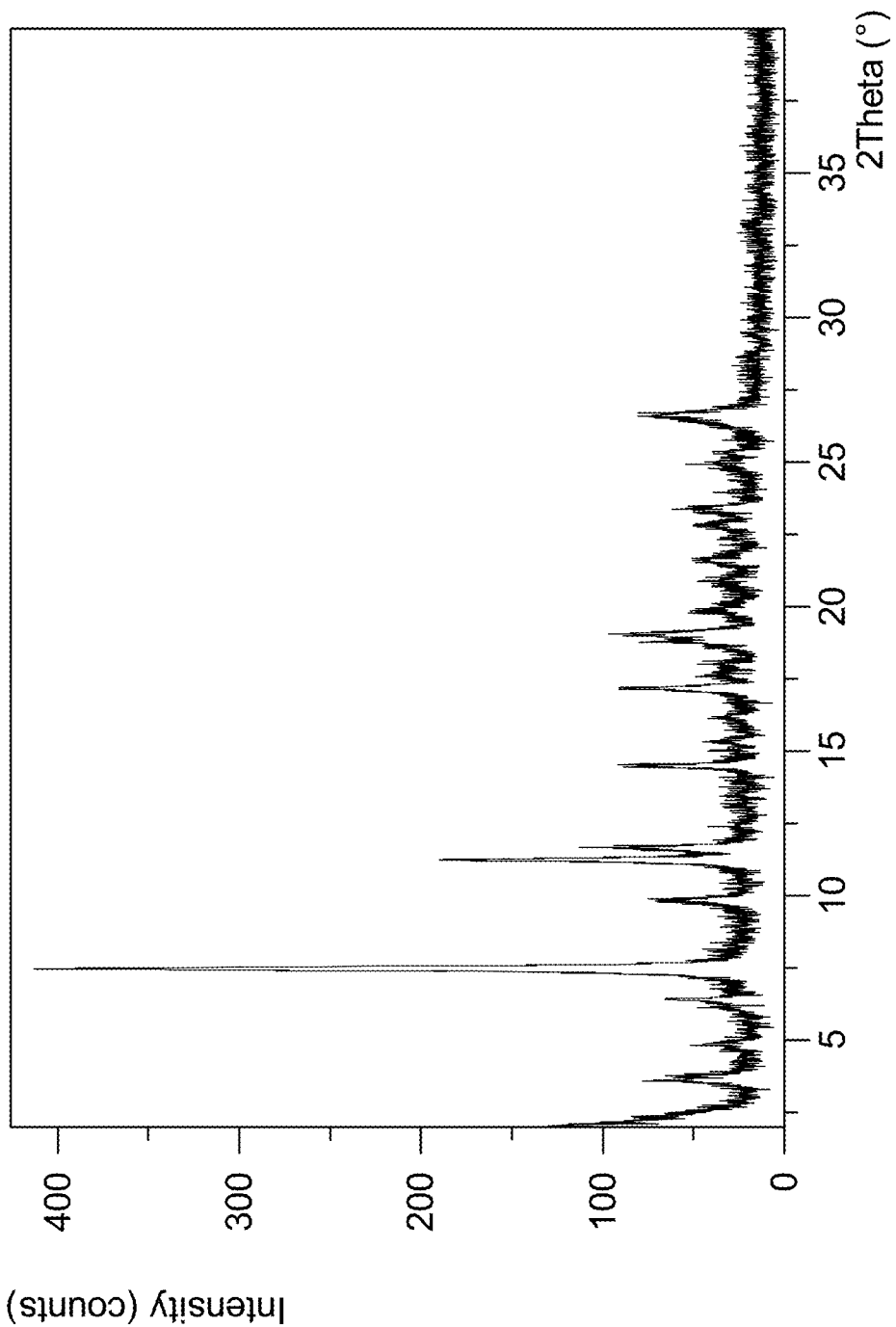
FIG. 10 shows a X-ray powder diffraction (XRPD) of Compound I bis-HCl Form IV.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form IV) is characterized by an X-ray powder diffractogram comprising the following peaks: 7.5, 11.2, and 14.5°2θ±0.2°2θ, as determined on a diffractometer using Cu—Kα radiation at a wavelength of 1.5406 Å. The diffractogram comprises peaks at 3.7 and 9.8°2θ±0.2°2θ. Compound I bis-HCl Form IV is also characterized by its full X-ray powder diffractogram as substantially as shown in FIG. 10.

Figure 11:
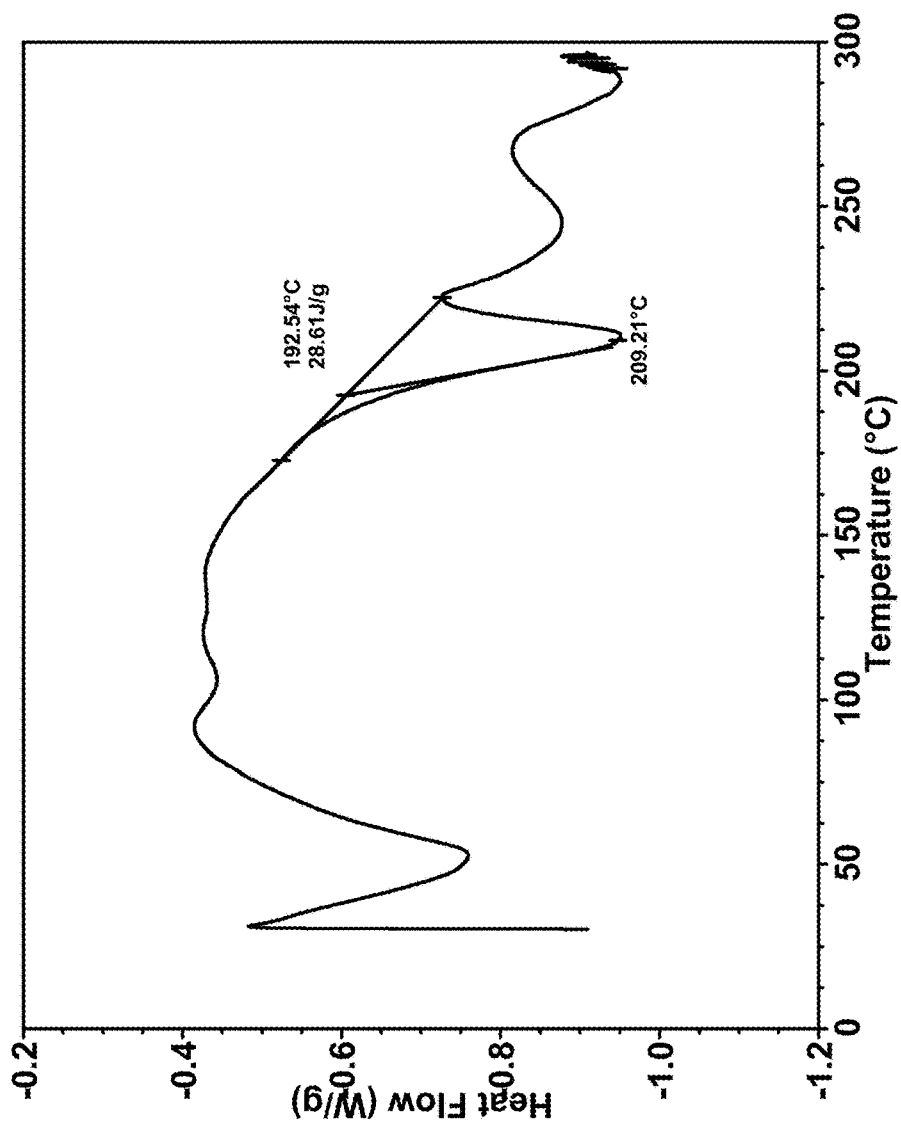
FIG. 11 shows a differential scanning calorimeter (DSC) curve of Compound I bis-HCl Form IV.

In some embodiments, Compound I bis-HCl Form IV is characterized by a differential scanning calorimetry (DSC) curve that comprises an endotherm at about 193° C. Compound I bis-HCl Form IV also is characterized by its full DSC curve as substantially as shown in FIG. 11.

Figure 13:
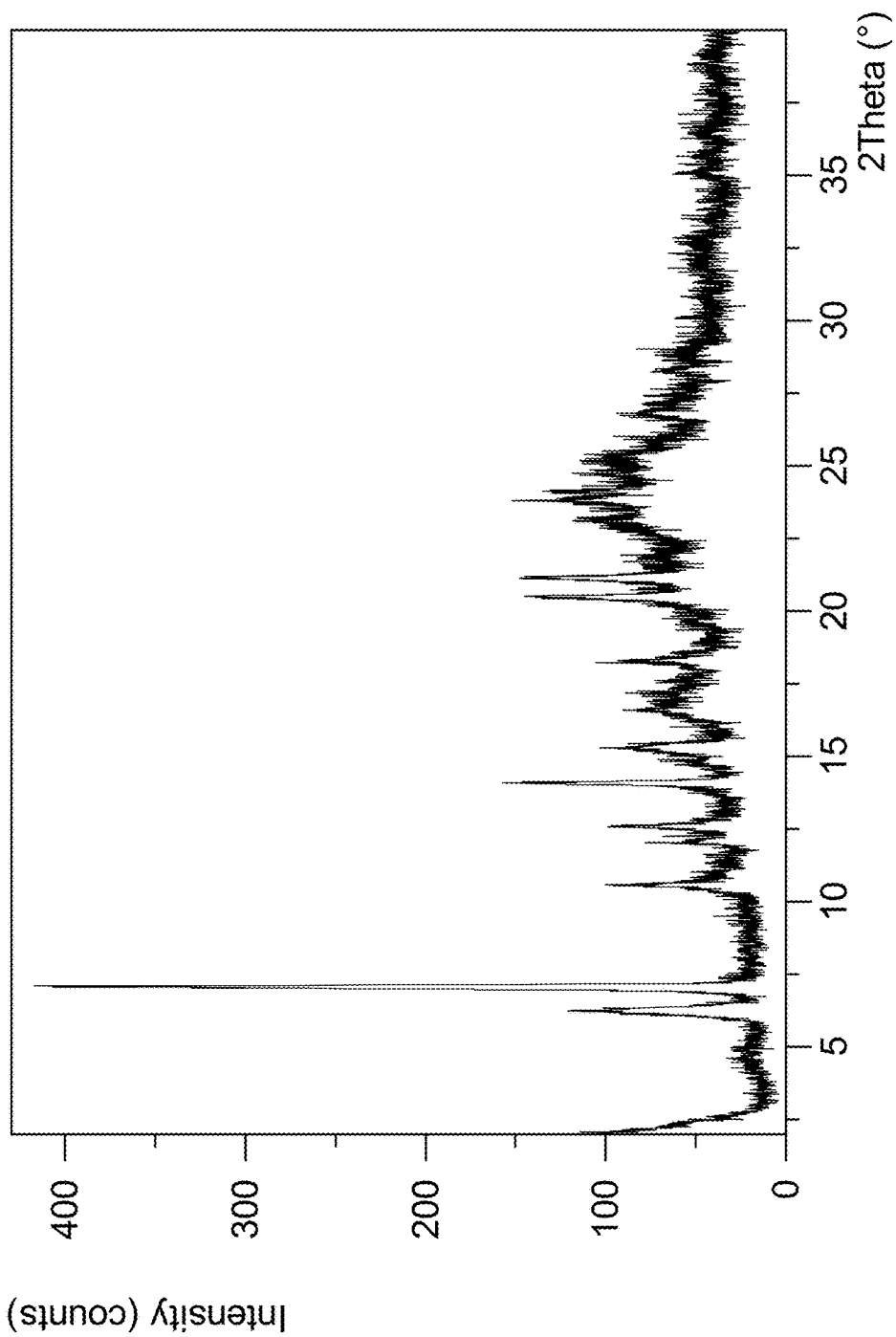
FIG. 13 shows a X-ray powder diffraction (XRPD) of Compound I bis-HCl Form V.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form V) is characterized by an X-ray powder diffractogram comprising the following peaks: 7.1, 10.6, and 14.1°2θ±0.2°2θ, as determined on a diffractometer using Cu—Kα radiation at a wavelength of 1.5406 Å. The diffractogram comprises peaks at 6.3 and 12.6°2θ±0.2°2θ. Compound I bis-HCl Form V is also characterized by its full X-ray powder diffractogram as substantially as shown in FIG. 13.

Figure 14:
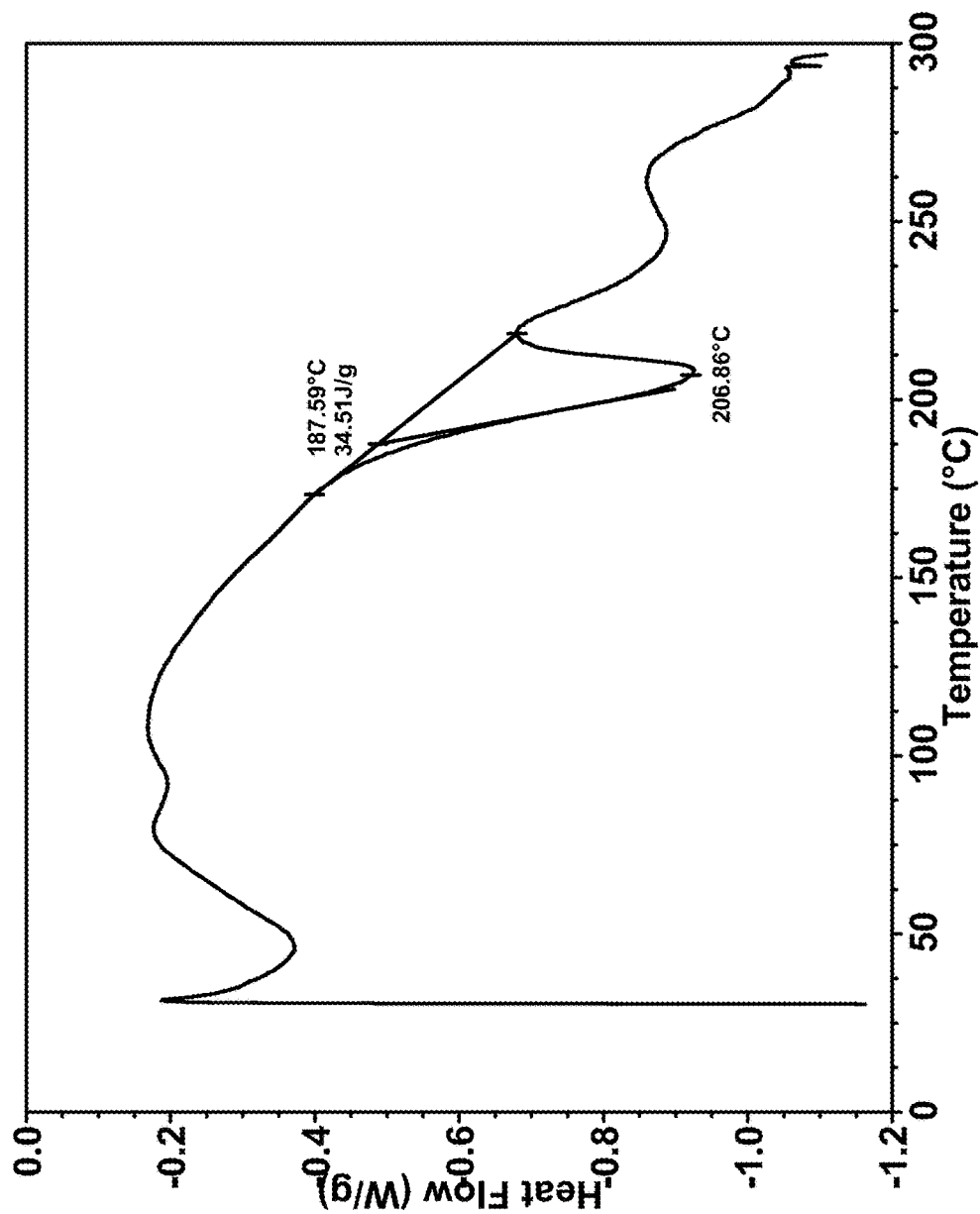
FIG. 14 shows a differential scanning calorimeter (DSC) curve of Compound I bis-HCl Form V.

In some embodiments, Compound I bis-HCl Form V is characterized by a differential scanning calorimetry (DSC) curve that comprises an endotherm at about 188° C. Compound I bis-HCl Form V also is characterized by its full DSC curve as substantially as shown in FIG. 14.

Figure 16:
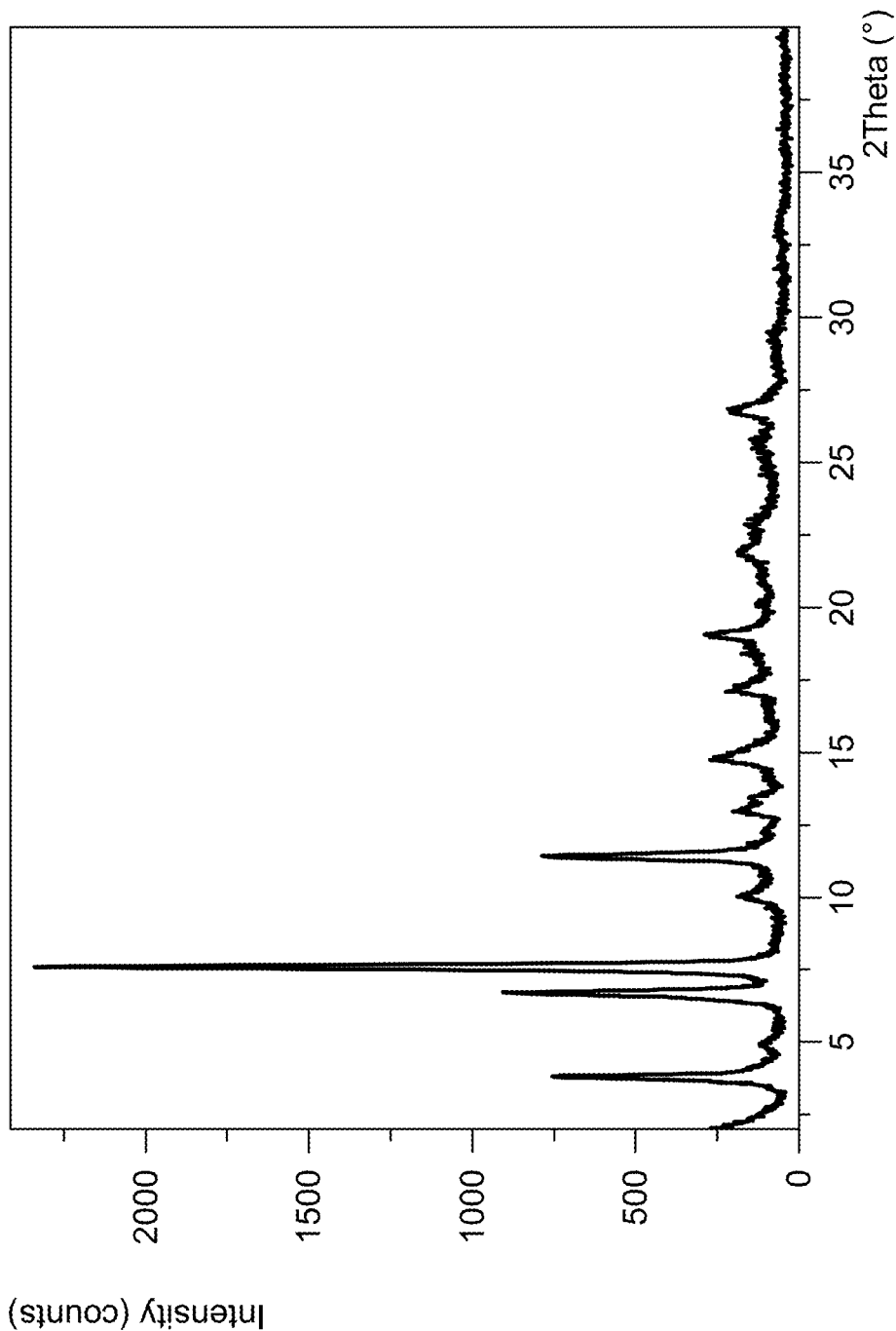
FIG. 16 shows a X-ray powder diffraction (XRPD) of Compound I bis-HCl Form VI.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrochloride (Compound I bis-HCl Form VI) is characterized by an X-ray powder diffractogram comprising the following peaks: 6.7 and 7.6°2θ±0.2°2θ, as determined on a diffractometer using Cu—Kα radiation at a wavelength of 1.5406 Å. The diffractogram comprises additional peaks at 3.8 and 11.4°2θ±0.2°2θ. Compound I bis-HCl Form VI is also characterized by its full X-ray powder diffractogram as substantially as shown in FIG. 16.

Figure 17:
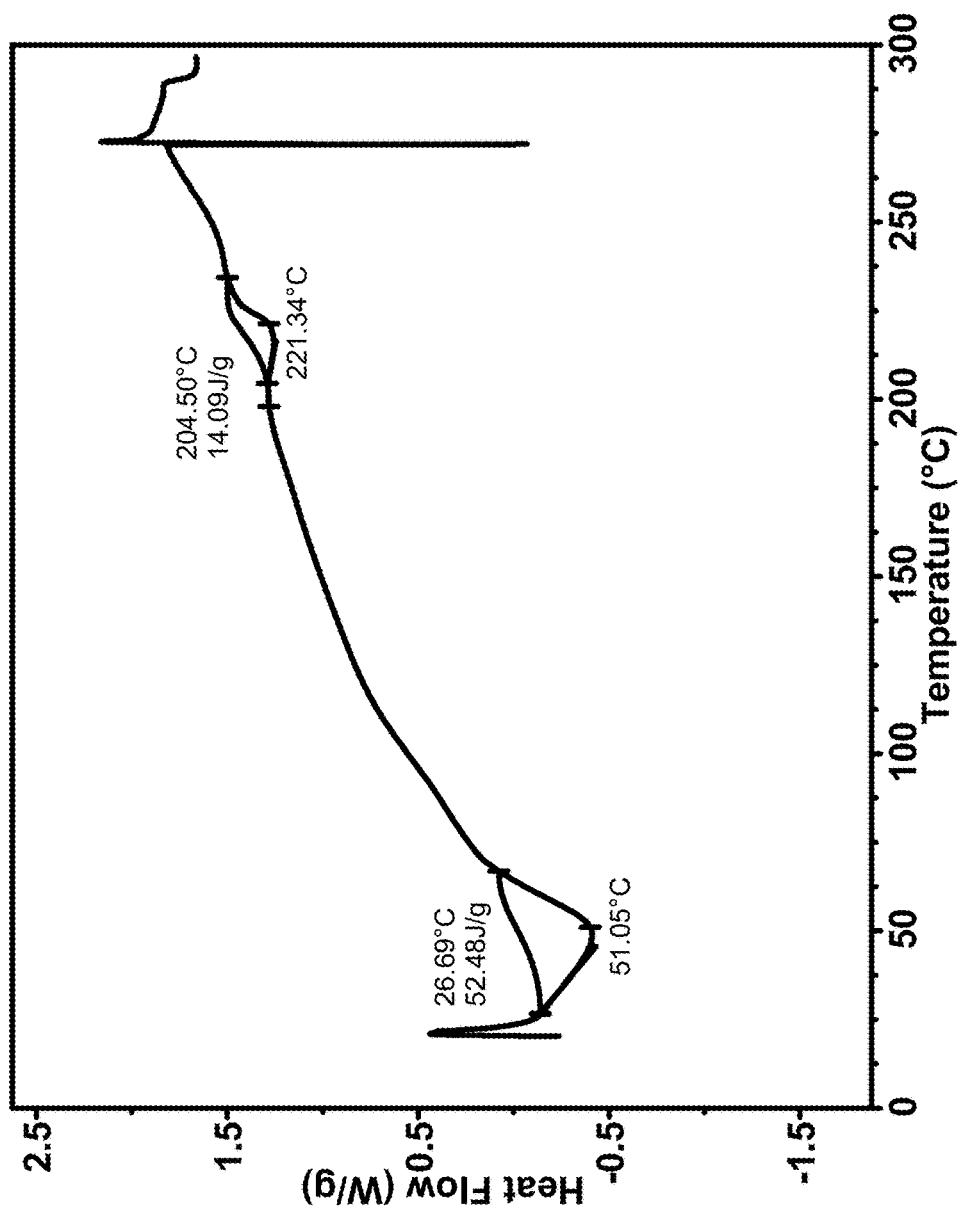
FIG. 17 shows a differential scanning calorimeter (DSC) curve of Compound I bis-HCl Form VI.

In some embodiments, Compound I bis-HCl Form VI is characterized by a differential scanning calorimetry (DSC) curve that comprises an endotherm at about 205° C. Compound I bis-HCl Form VI also is characterized by its full DSC curve as substantially as shown in FIG. 17.

Figure 20:
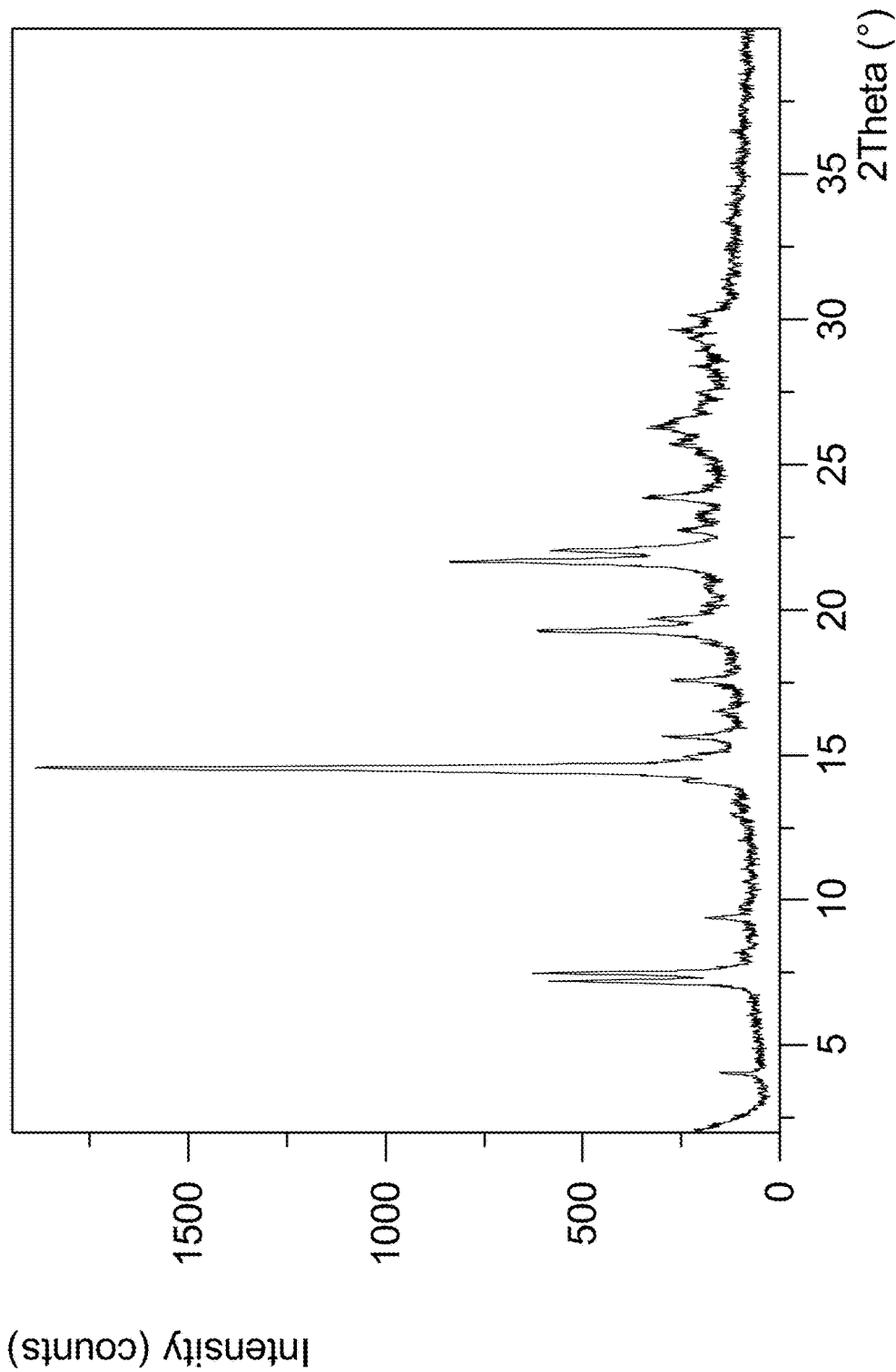
FIG. 20 shows a X-ray powder diffraction (XRPD) of Compound I Phosphate Form VII.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form VII) characterized by an X-ray powder diffractogram comprising the following peaks: 7.5, 14.6, and 21.6°2θ±0.2°2θ, as determined on a diffractometer using Cu—Kα radiation at a wavelength of 1.5406 Å. The diffractogram comprises additional peaks at 7.2 and 19.3°2θ±0.2°2θ. Compound I Phosphate Form VII is also characterized by its full X-ray powder diffractogram as substantially as shown in FIG. 20.

Figure 21:
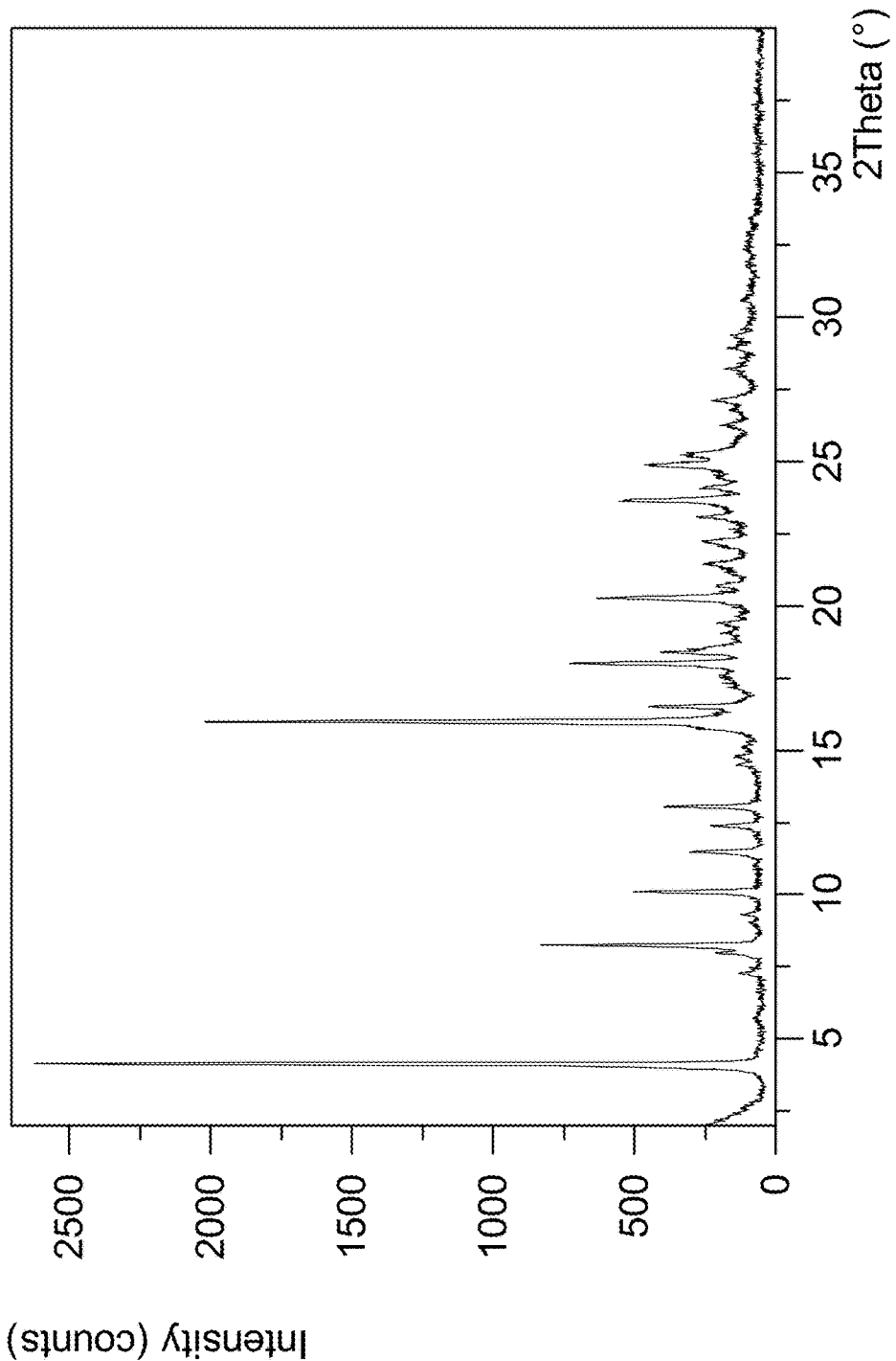
FIG. 21 shows a X-ray powder diffraction (XRPD) of Compound I Phosphate Form VIII.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form VIII) characterized by an X-ray powder diffractogram comprising the following peaks: 4.2, 8.3, and 16.0°2θ±0.2°2θ, as determined on a diffractometer using Cu—Kα radiation at a wavelength of 1.5406 Å. The diffractogram comprises additional peaks at 10.1, 11.5, and 13.1°2θ±0.2°2θ. Compound I Phosphate Form VIII is also characterized by its full X-ray powder diffractogram as substantially as shown in FIG. 21.

Figure 22:
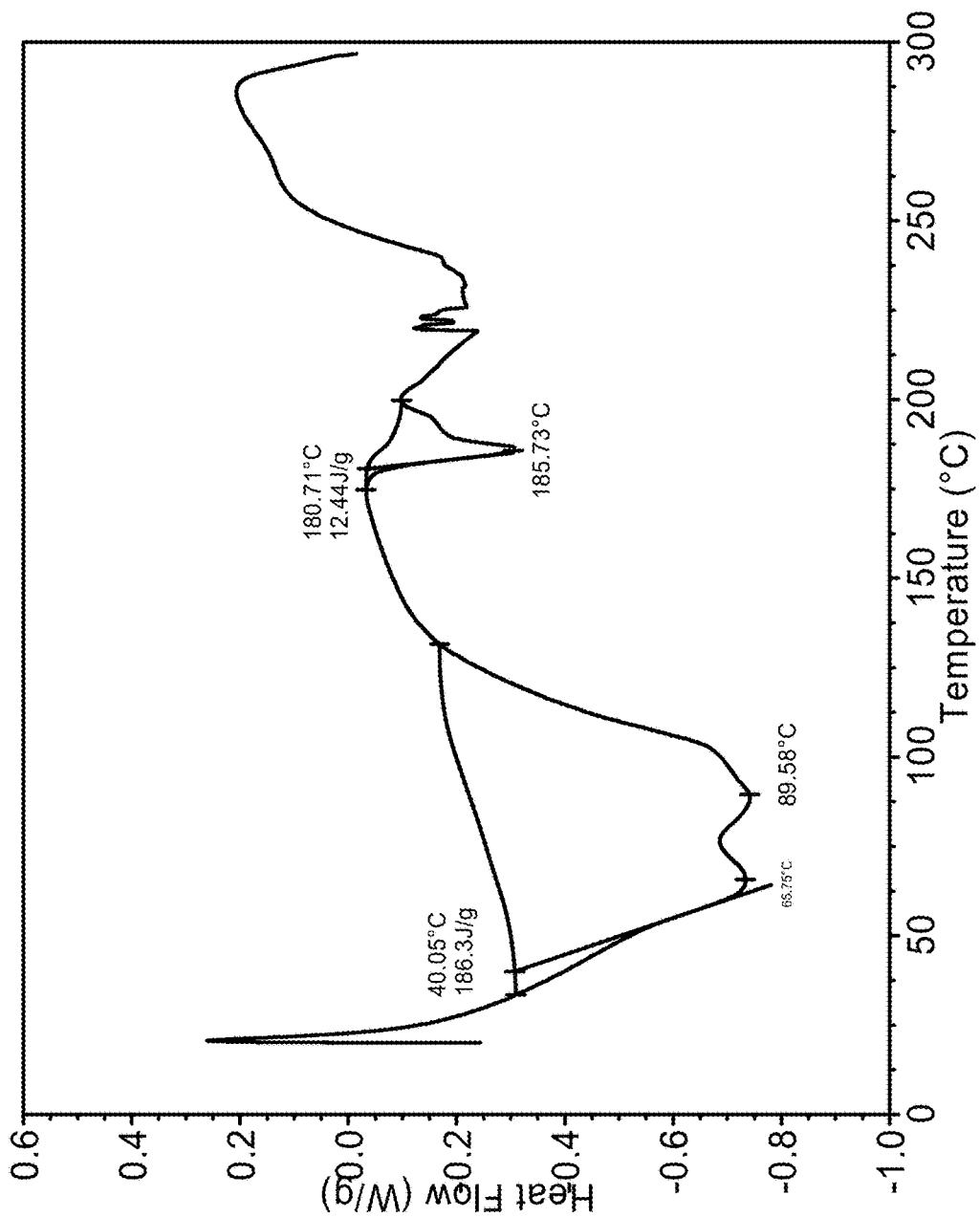
FIG. 22 shows a differential scanning calorimeter (DSC) curve of Compound I Phosphate Form VIII.

In some embodiments, Compound I Phosphate Form XII is characterized by a differential scanning calorimetry (DSC) curve that comprises an endotherm at about 181° C. Compound I Phosphate Form VIII is also characterized by its full DSC curve as substantially as shown in FIG. 22.

Figure 24:
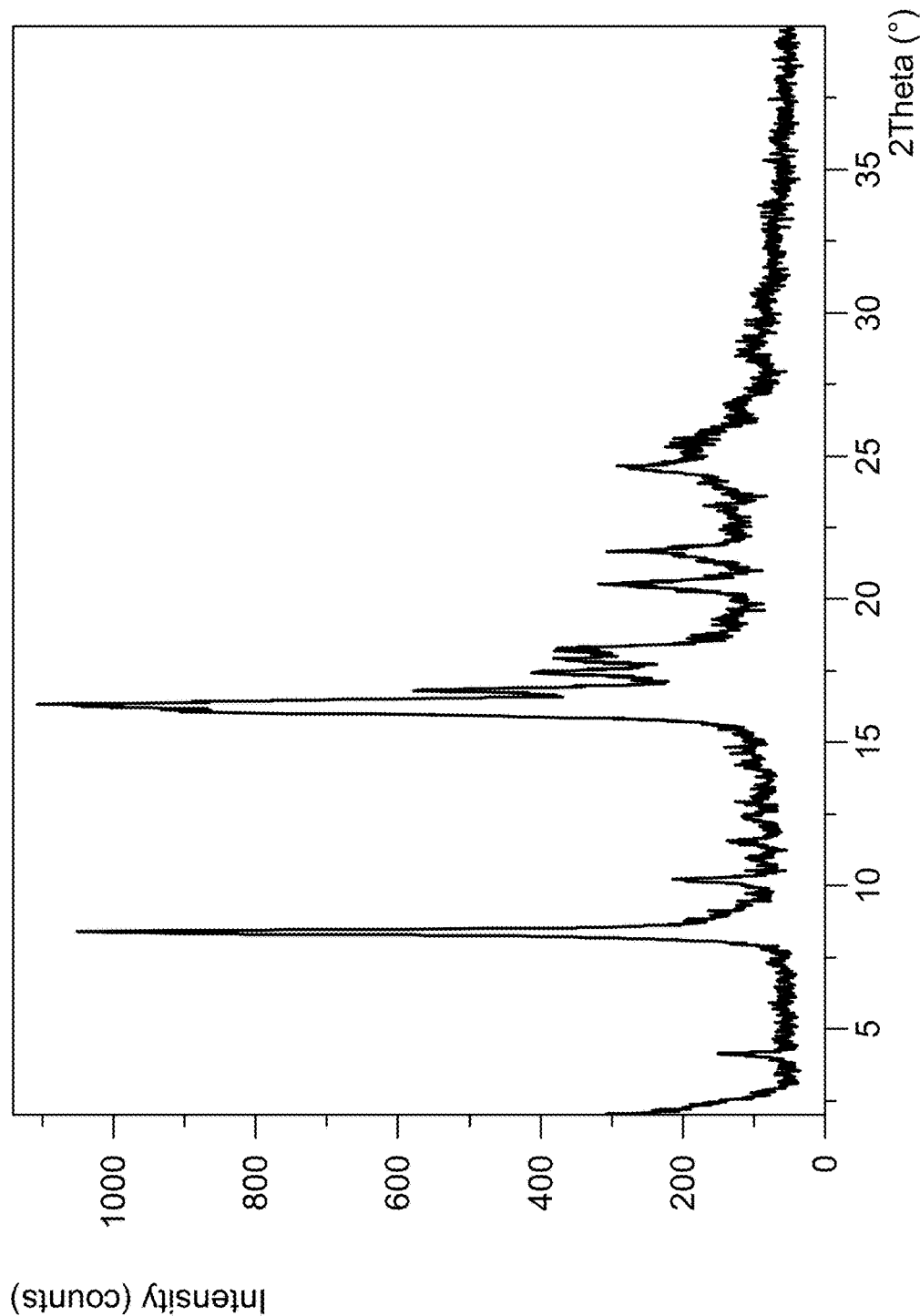
FIG. 24 shows a X-ray powder diffraction (XRPD) of Compound I Phosphate Form IX.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form IX) is characterized by an X-ray powder diffractogram comprising the following peaks: 8.4, 16.1, and 16.3°2θ±0.2°2θ, as determined on a diffractometer using Cu—Kα radiation at a wavelength of 1.5406 Å. The diffractogram comprises additional peaks at 10.2, 20.5, and 21.7°2θ±0.2°2θ. Compound I Phosphate Form IX is also characterized by its full X-ray powder diffractogram as substantially as shown in FIG. 24.

Figure 25:
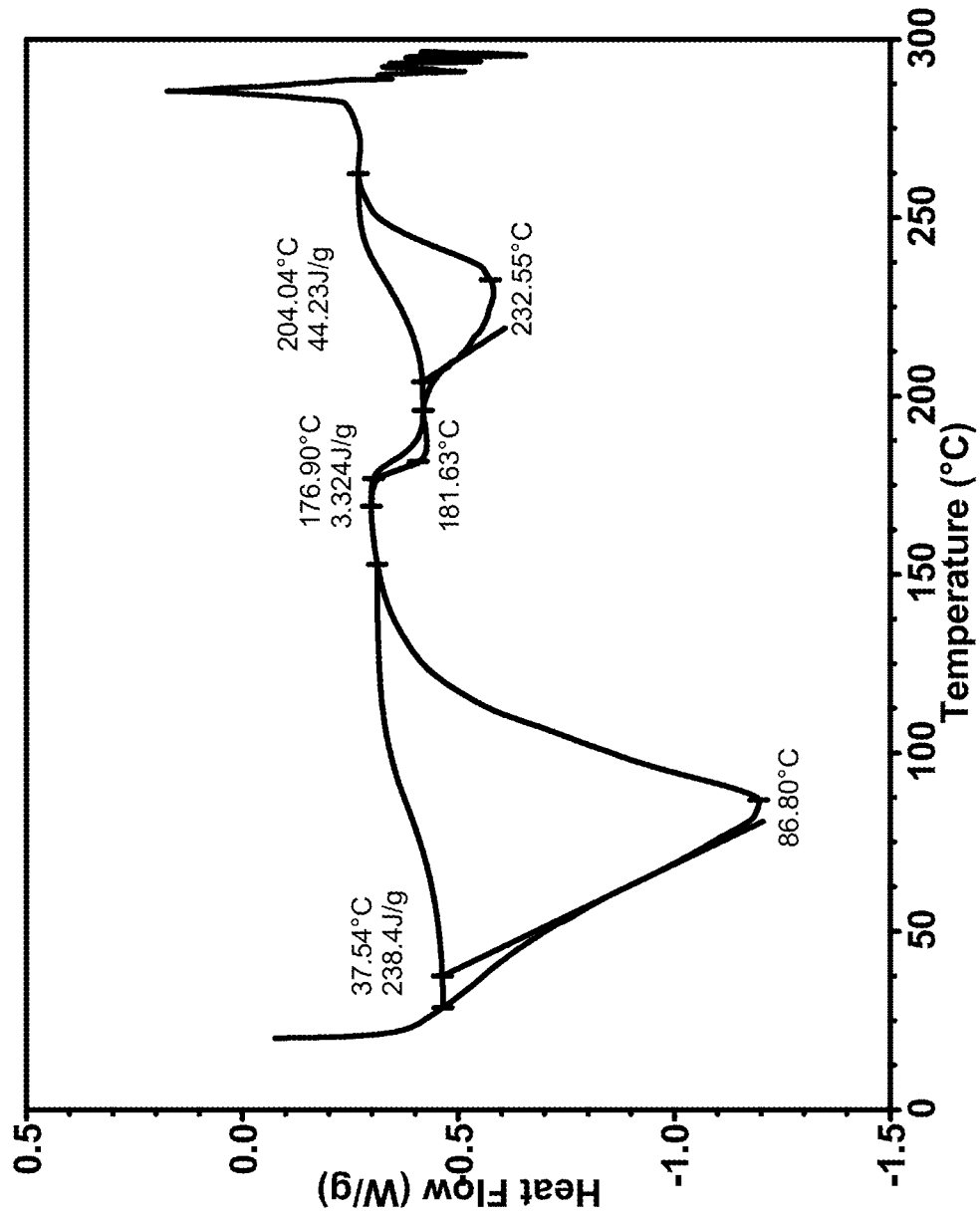
FIG. 25 shows a differential scanning calorimeter (DSC) curve of Compound I Phosphate Form IX.

In some embodiments, Compound I Phosphate Form IX is characterized by a differential scanning calorimetry (DSC) curve that comprises an endotherm at about 177° C. and an endotherm at about 204° C. Compound I Phosphate Form IX is also characterized by its full DSC curve as substantially as shown in FIG. 25.

Figure 27:
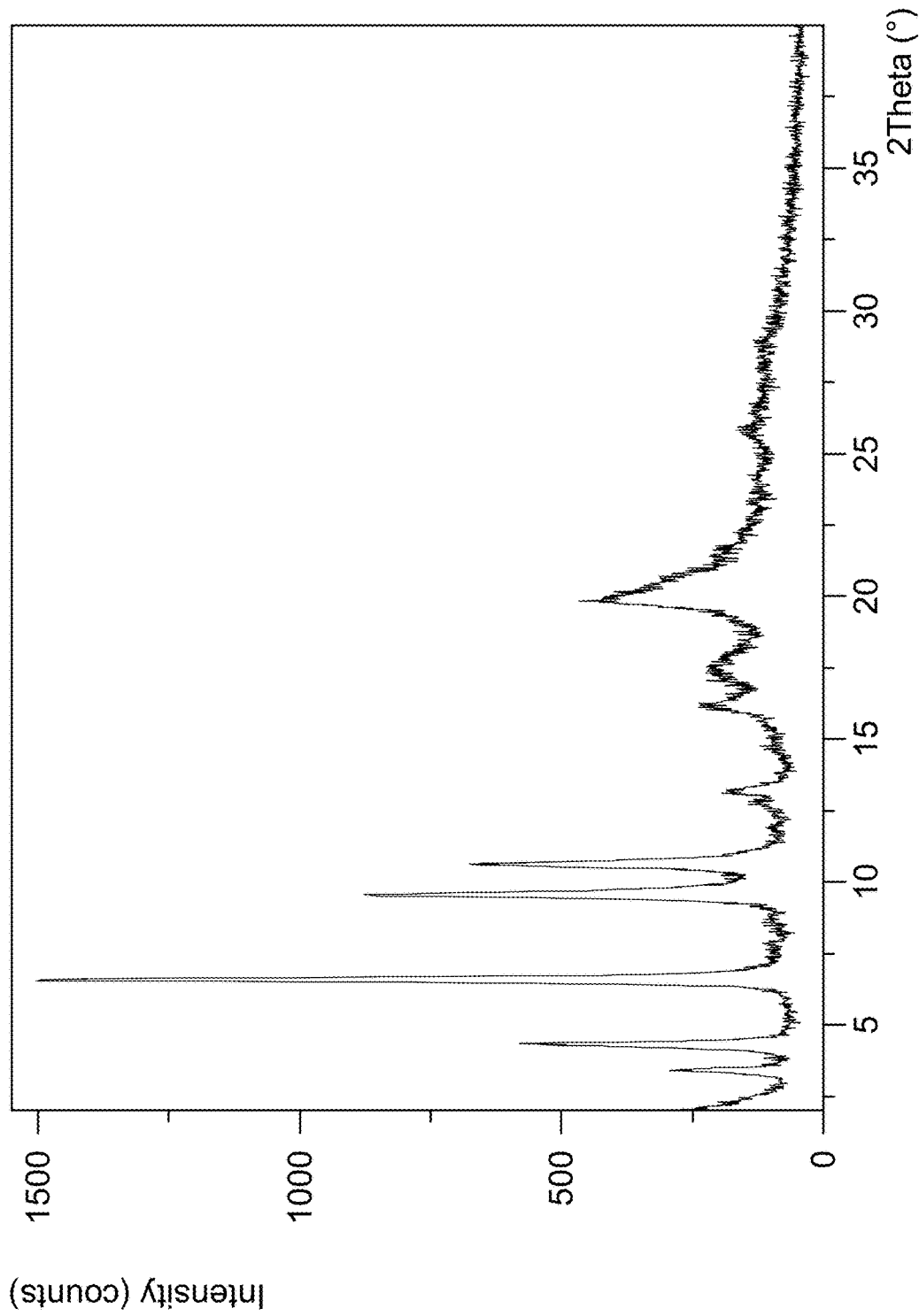
FIG. 27 shows a X-ray powder diffraction (XRPD) of Compound I Phosphate Form X.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form X) characterized by an X-ray powder diffractogram comprising the following peaks: 6.6, 9.5, and 10.6°2θ±0.2°2θ, as determined on a diffractometer using Cu—Kα radiation at a wavelength of 1.5406 Å. The diffractogram comprises additional peaks at 3.4 and 4.3°2θ±0.2°2θ. Compound I Phosphate Form X is also characterized by its full X-ray powder diffractogram as substantially as shown in FIG. 27.

Figure 28:
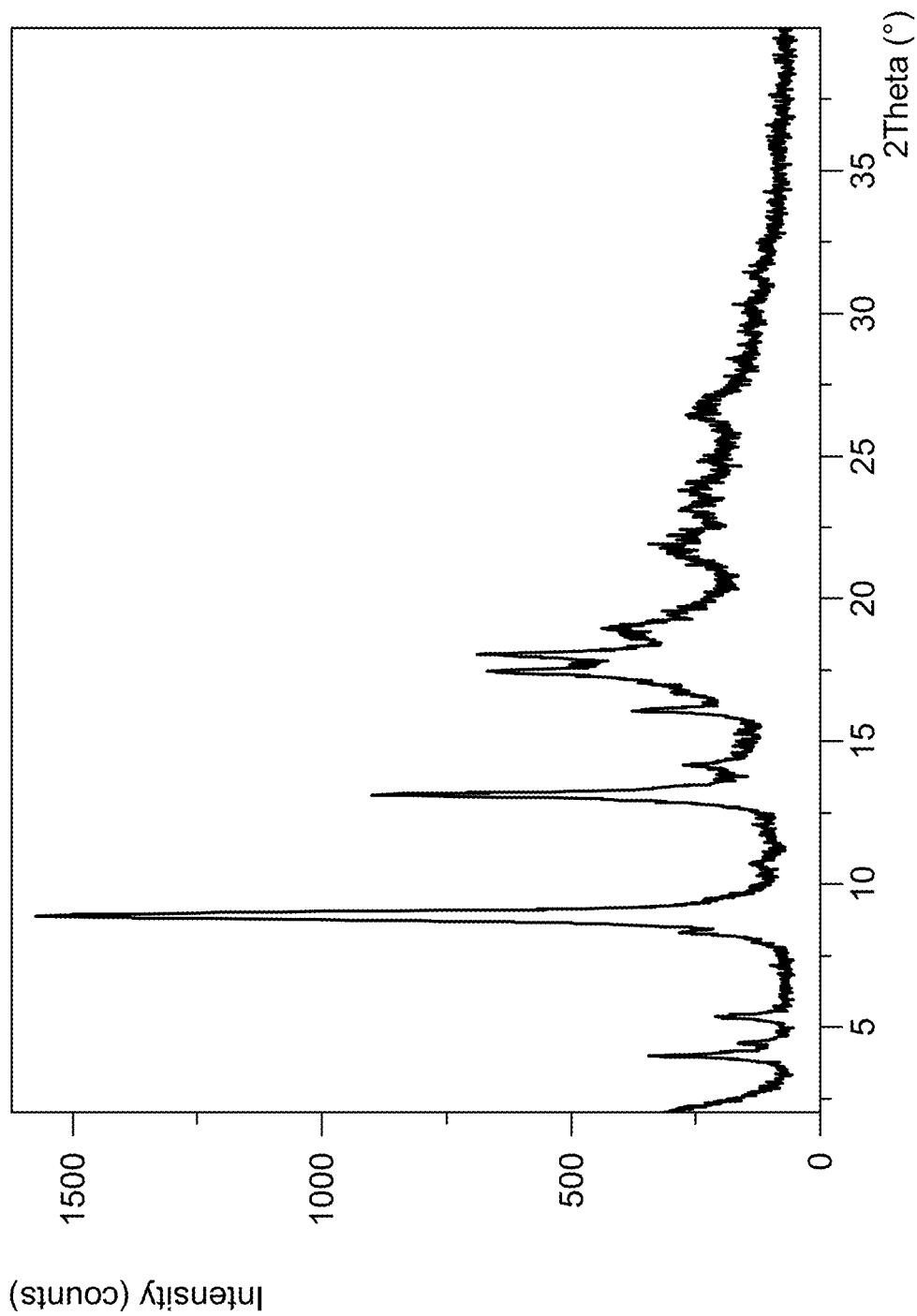
FIG. 28 shows a X-ray powder diffraction (XRPD) of Compound I Phosphate Form XI.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XI) is characterized by an X-ray powder diffractogram comprising the following peaks: 8.9, 13.1, and 18.1°2θ±0.2°2θ, as determined on a diffractometer using Cu—Kα radiation at a wavelength of 1.5406 Å. The diffractogram comprises additional peaks at 4.0 and 17.5°2θ±0.2°2θ. Compound I Phosphate Form XI is also characterized by its full X-ray powder diffractogram as substantially as shown in FIG. 28.

Figure 29:
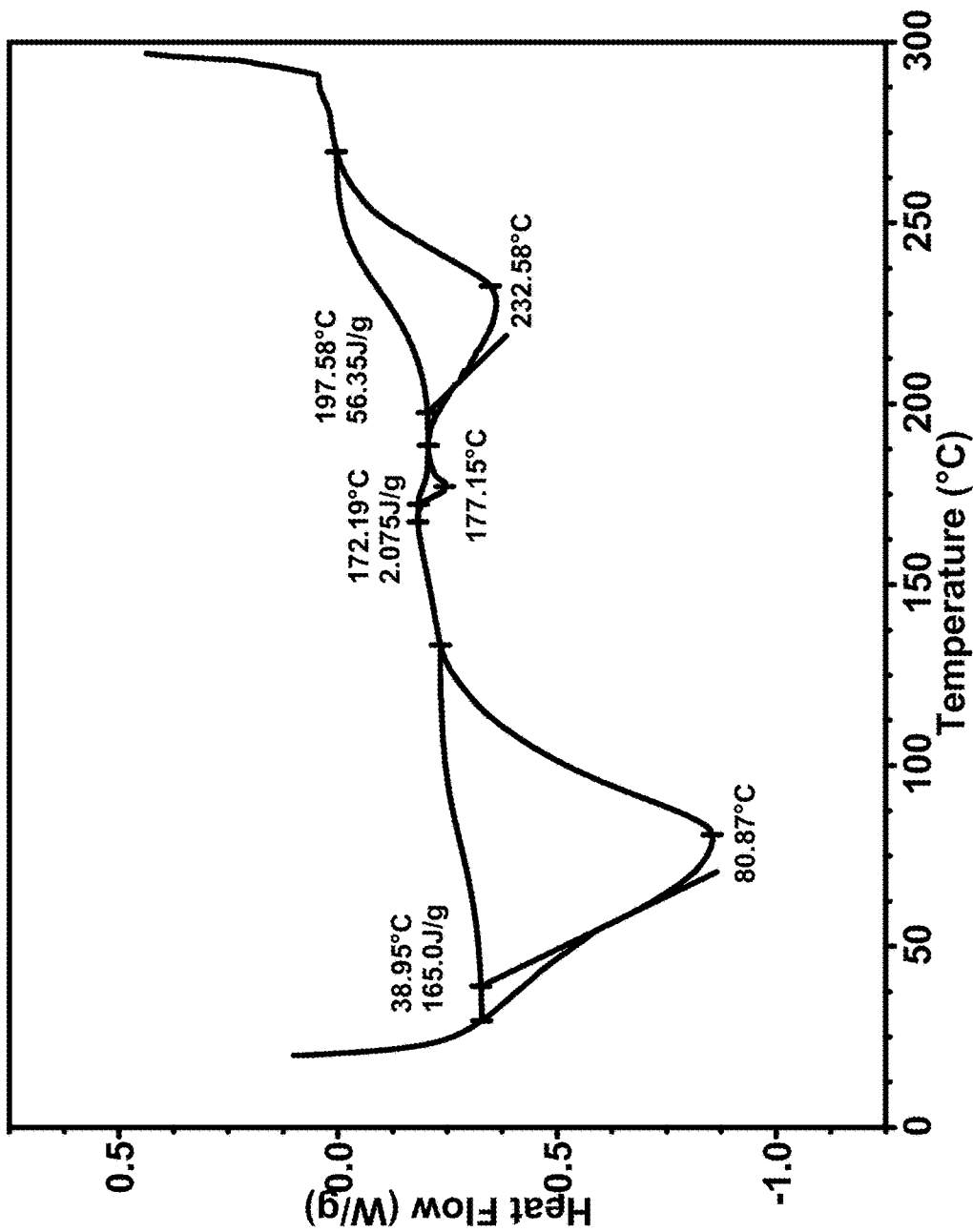
FIG. 29 shows a differential scanning calorimeter (DSC) curve of Compound I Phosphate Form XI.

In some embodiments, Compound I Phosphate Form XI is also characterized by a differential scanning calorimetry (DSC) curve that comprises an endotherm at about 172° C. and an endotherm at about 198° C. Compound I Phosphate Form XI is also characterized by its full DSC curve as substantially as shown in FIG. 29.

Figure 31:
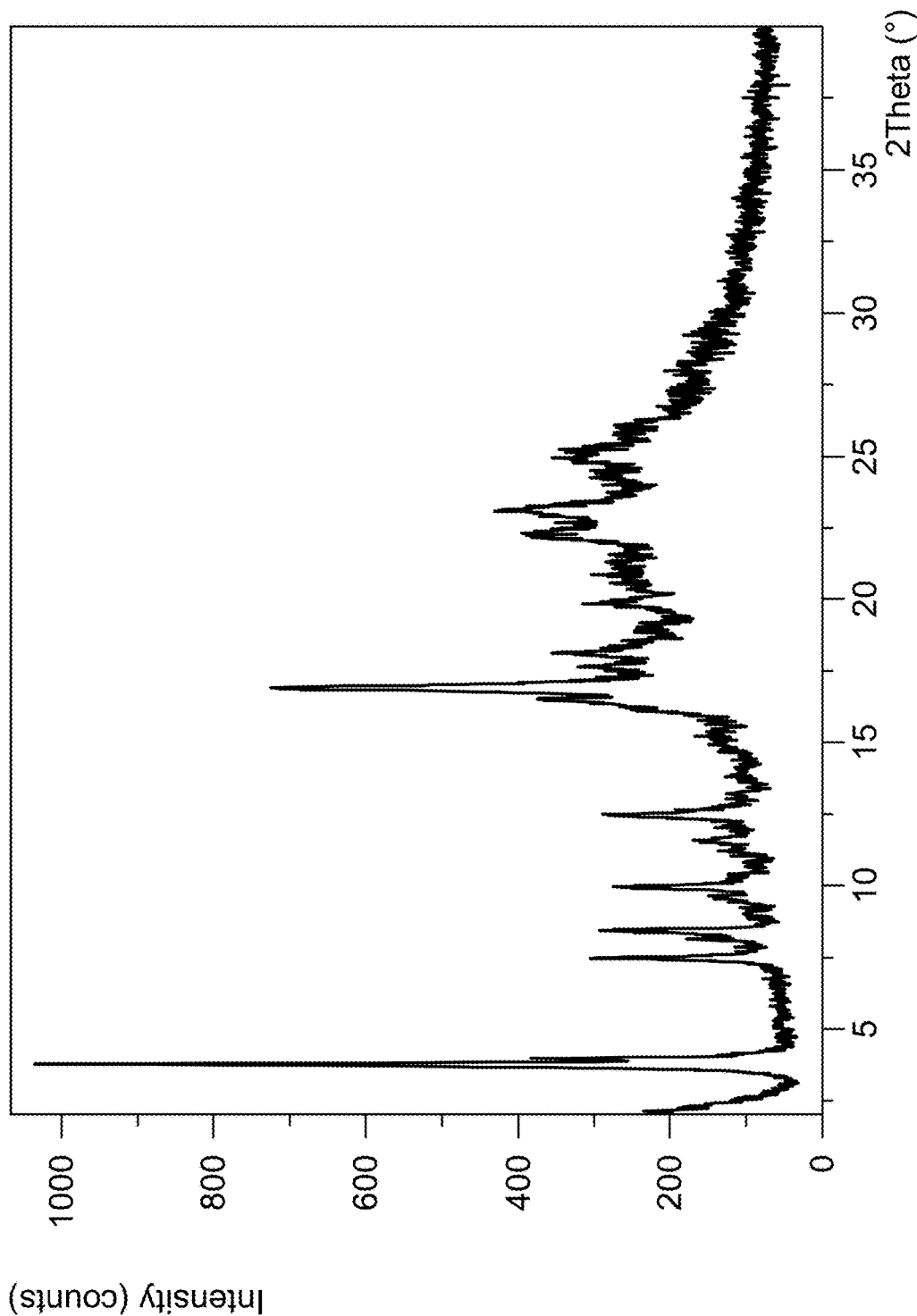
FIG. 31 shows a X-ray powder diffraction (XRPD) of Compound I Phosphate Form XII.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XII) is characterized by an X-ray powder diffractogram comprising the following peaks: 3.8, 7.5, and 16.9°2θ±0.2°2θ, as determined on a diffractometer using Cu—Kα radiation at a wavelength of 1.5406 Å. The diffractogram comprises additional peaks at 8.5, 10.0, and 12.4°2θ±0.2°2θ. Compound I Phosphate Form XII is also characterized by its full X-ray powder diffractogram as substantially as shown in FIG. 31.

Figure 32:
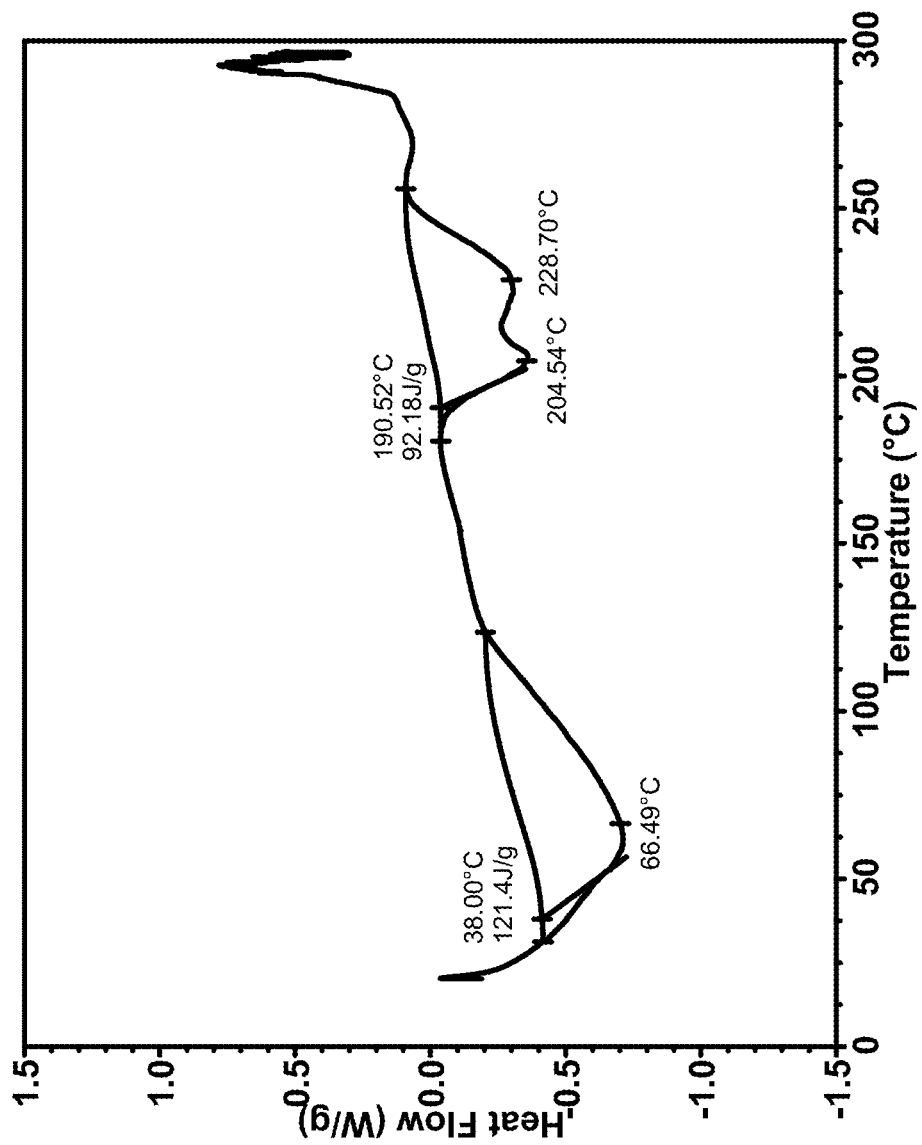
FIG. 32 shows a differential scanning calorimeter (DSC) curve of Compound I Phosphate Form XII.

In some embodiments, Compound I Phosphate Form XII is also characterized by a differential scanning calorimetry (DSC) curve that comprises an endotherm at about 205° C. and an endotherm at about 229° C. Compound I Phosphate Form XII is also characterized by its full DSC curve as substantially as shown in FIG. 32.

Figure 34:
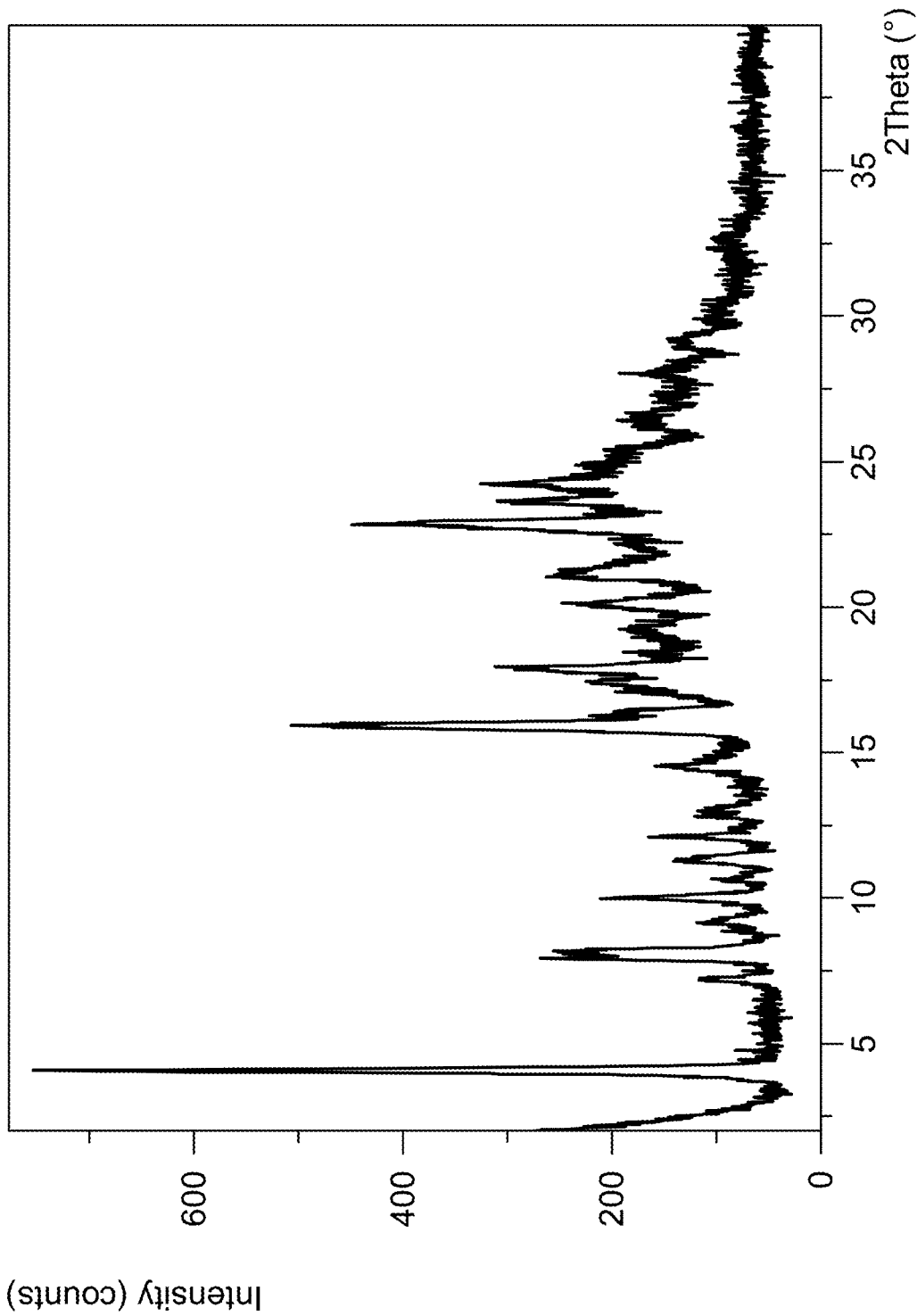
FIG. 34 shows a X-ray powder diffraction (XRPD) of Compound I Phosphate Form XIII.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XIII) 15 characterized by an X-ray powder diffractogram comprising the following peaks: 4.1, 15.9, and 22.9°2θ±0.2°2θ, as determined on a diffractometer using Cu—Kα radiation at a wavelength of 1.5406 Å. The diffractogram comprises additional peaks at 7.9, 10.0, and 17.9°2θ±0.2°2θ. Compound I Phosphate Form XIII is also characterized by its full X-ray powder diffractogram as substantially as shown in FIG. 34.

Figure 35:
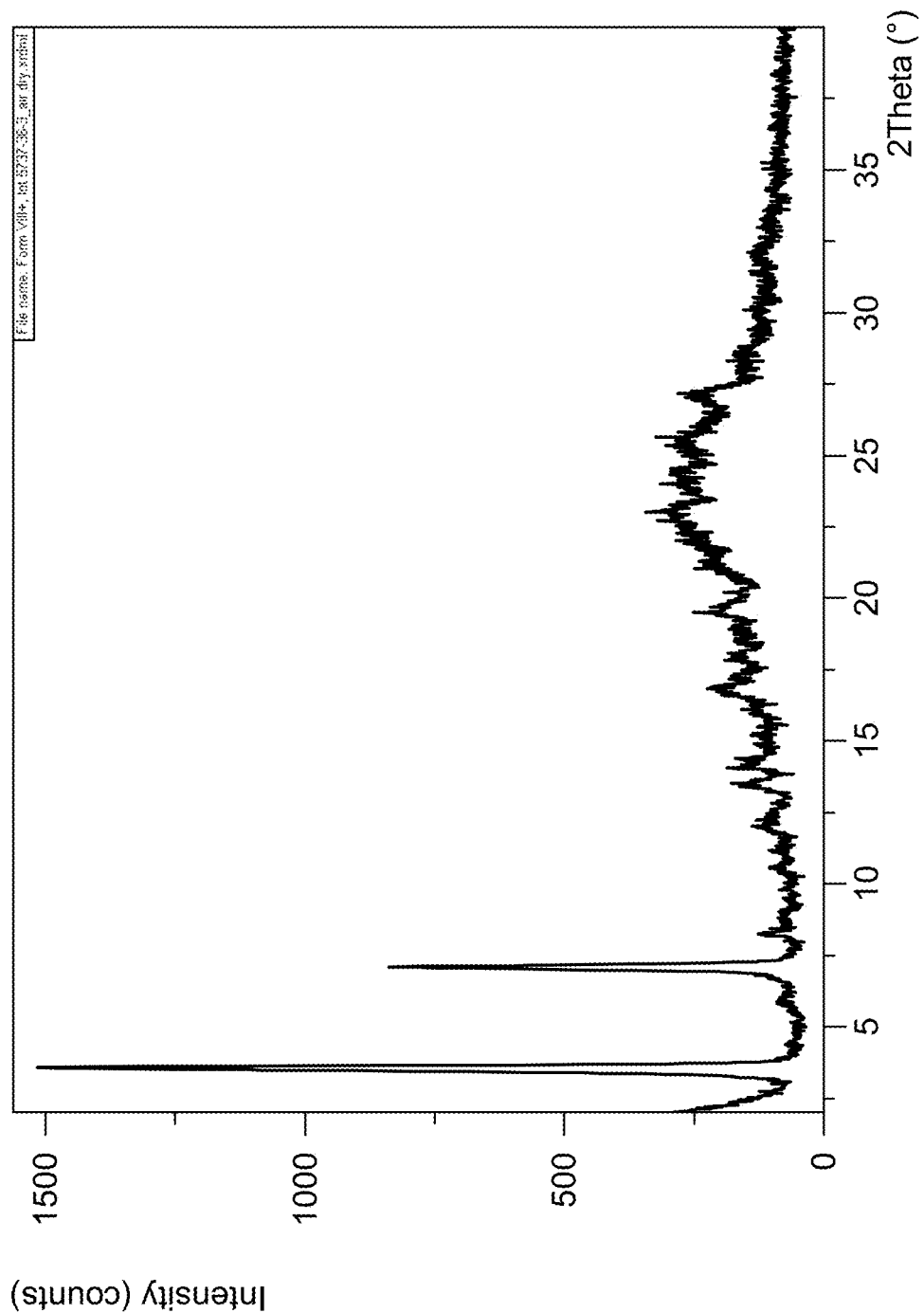
FIG. 35 shows a X-ray powder diffraction (XRPD) of Compound I Phosphate Form XIV.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XIV) is characterized by an X-ray powder diffractogram comprising the following peaks: 3.5 and 6.9°2θ±0.2°2θ, as determined on a diffractometer using Cu—Kα radiation at a wavelength of 1.5406 Å. The diffractogram comprises additional peaks at 8.3 and 12.0°2θ±0.2°2θ. Compound I Phosphate Form XIV is also characterized by its full X-ray powder diffractogram as substantially as shown in FIG. 35.

Figure 48:
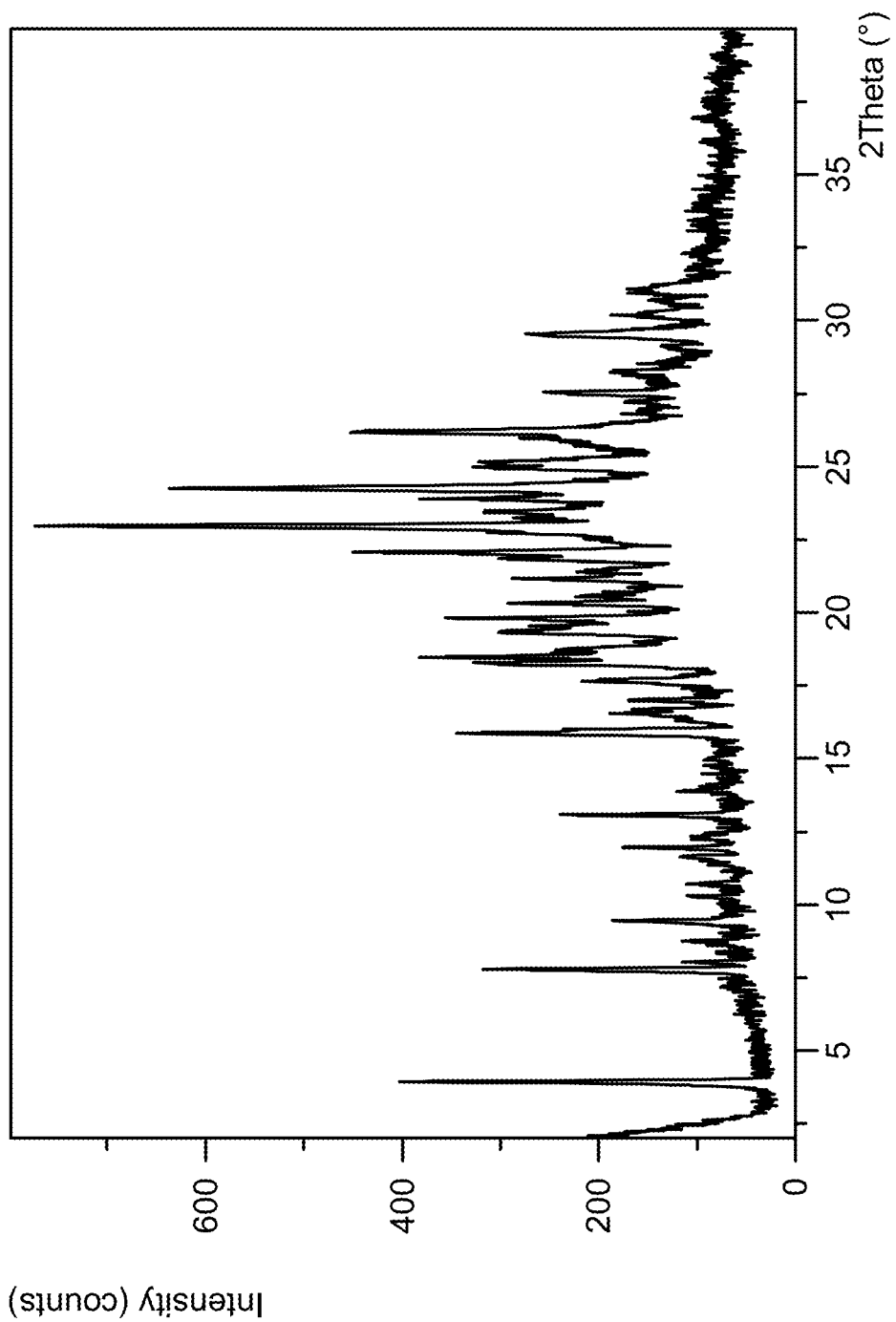
FIG. 48 shows a X-ray powder diffraction (XRPD) of Compound I Phosphate Form XV.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XV) characterized by an X-ray powder diffractogram comprising the following peaks: 4.0, 23.0, and 24.2°2θ±0.2°2θ, as determined on a diffractometer using Cu—Kα radiation at a wavelength of 1.5406 Å. The diffractogram further comprises peaks at 7.8 and 15.9°2θ±0.2°2θ. Compound I Phosphate Form XV is also characterized by its full X-ray powder diffractogram is substantially as shown in FIG. 48.

Figure 37:
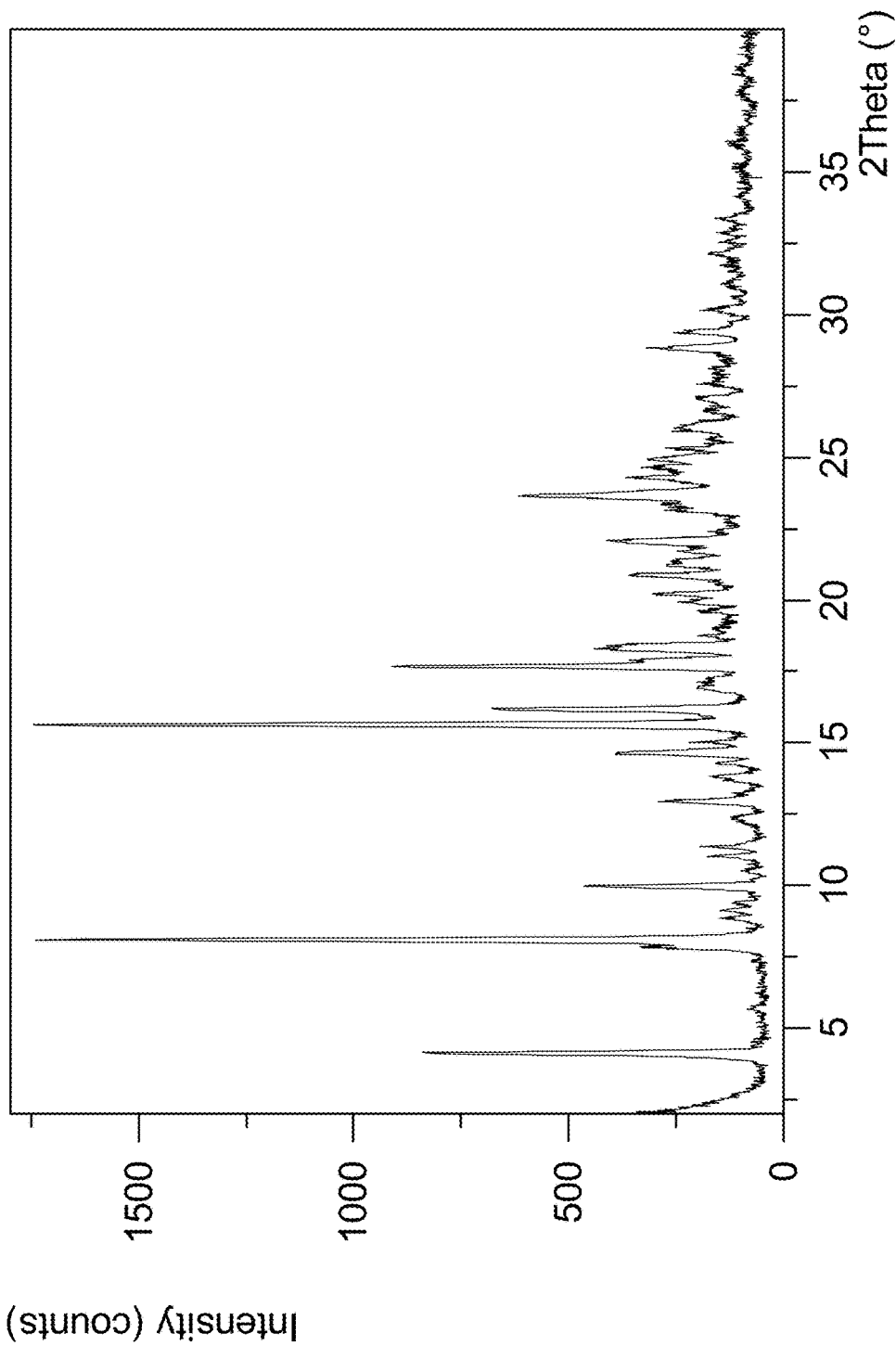
FIG. 37 shows a X-ray powder diffraction (XRPD) of Compound I L-tartrate Form XVI.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate L-tartrate (Compound I L-tartrate Form XVI) is characterized by an X-ray powder diffractogram comprising the following peaks: 4.1, 8.1, and 15.6°2θ±0.2°2θ, as determined on a diffractometer using Cu—Kα radiation at a wavelength of 1.5406 Å. The diffractogram comprises additional peaks at 10.0, 12.9, and 14.6°2θ±0.2°2θ. Compound I L-tartrate Form XVI is also characterized by its full X-ray powder diffractogram as substantially as shown in FIG. 37.

Figure 38:
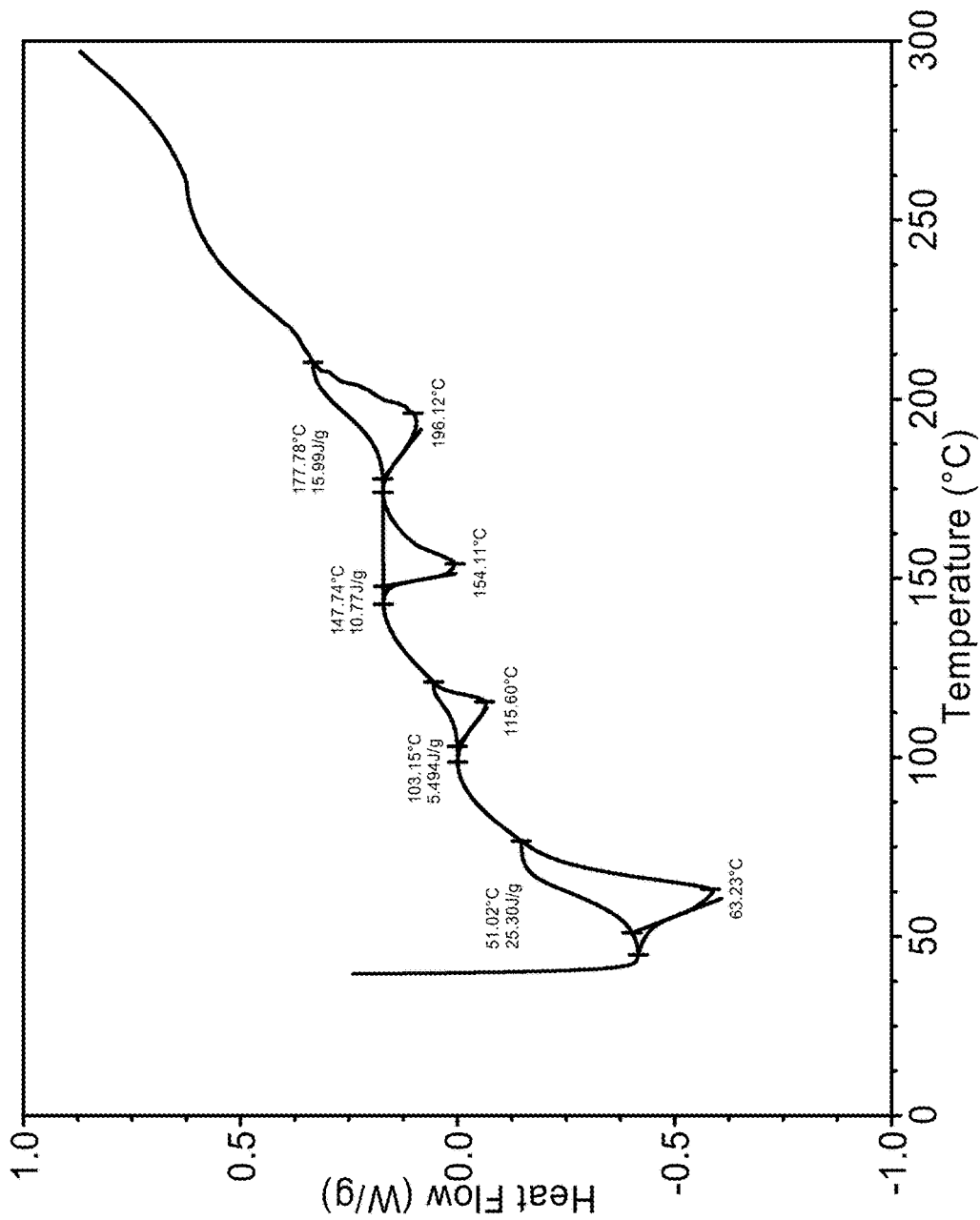
FIG. 38 shows a differential scanning calorimeter (DSC) curve of Compound I L-tartrate Form XVI.

In some embodiments, Compound I L-tartrate Form XVI is characterized by a differential scanning calorimetry (DSC) curve that comprises an endotherm at about 103° C., an endotherm at about 148° C., and an endotherm at about 178° C. Compound I L-tartrate Form XVI is also characterized by its full DSC curve as substantially as shown in FIG. 38.

Figure 40:
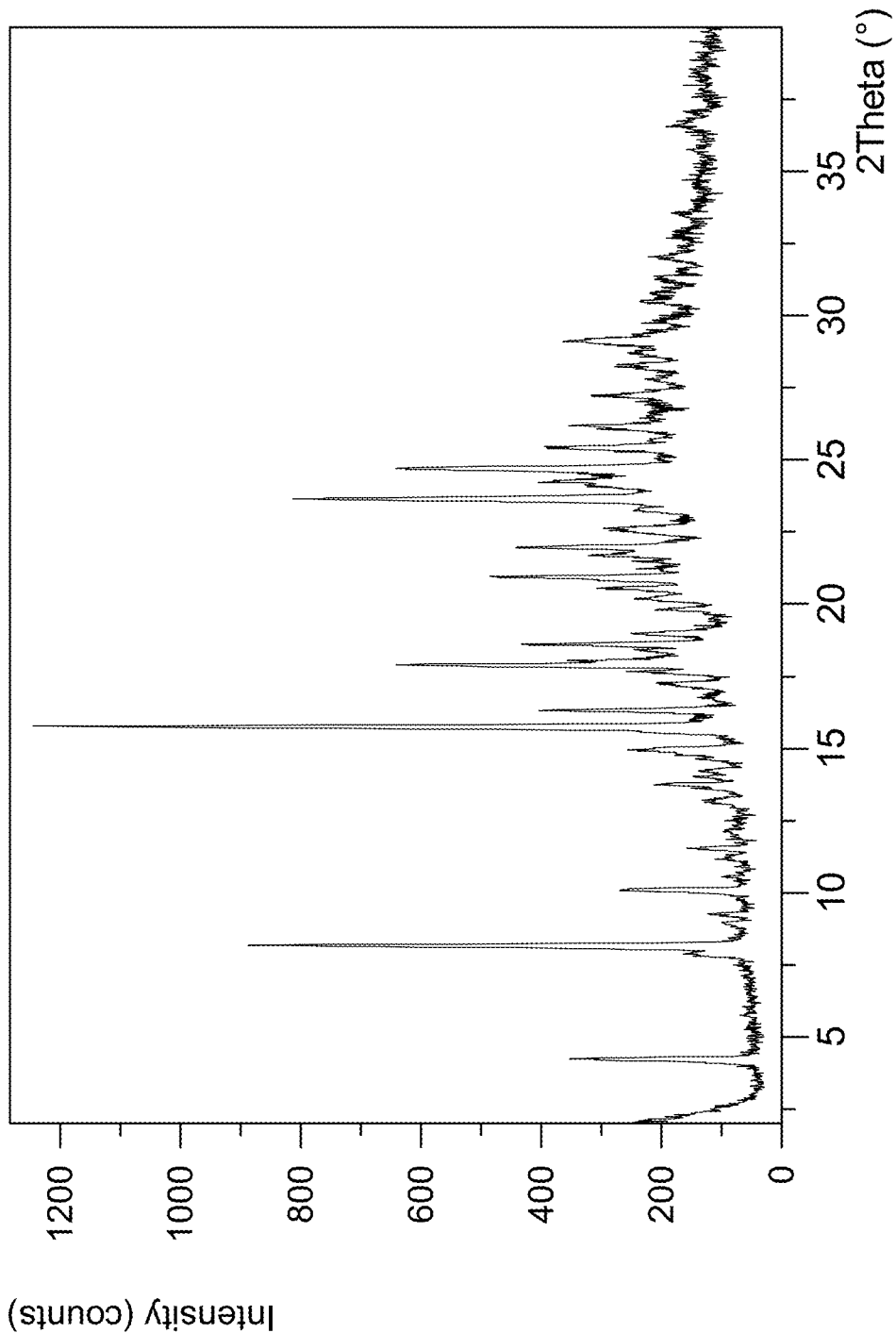
FIG. 40 shows a X-ray powder diffraction (XRPD) of Compound I L-tartrate Form XVII.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate L-tartrate (Compound I L-tartrate Form XVII) is characterized by an X-ray powder diffractogram comprising the following peaks: 8.2, 15.8, and 22.6°2θ±0.2°2θ, as determined on a diffractometer using Cu—Kα radiation at a wavelength of 1.5406 Å. The diffractogram comprises additional peaks at 4.3, 10.1, and 17.9°2θ±0.2°2θ. Compound I L-tartrate Form XVII is also characterized by its full X-ray powder diffractogram as substantially as shown in FIG. 40.

Figure 41:
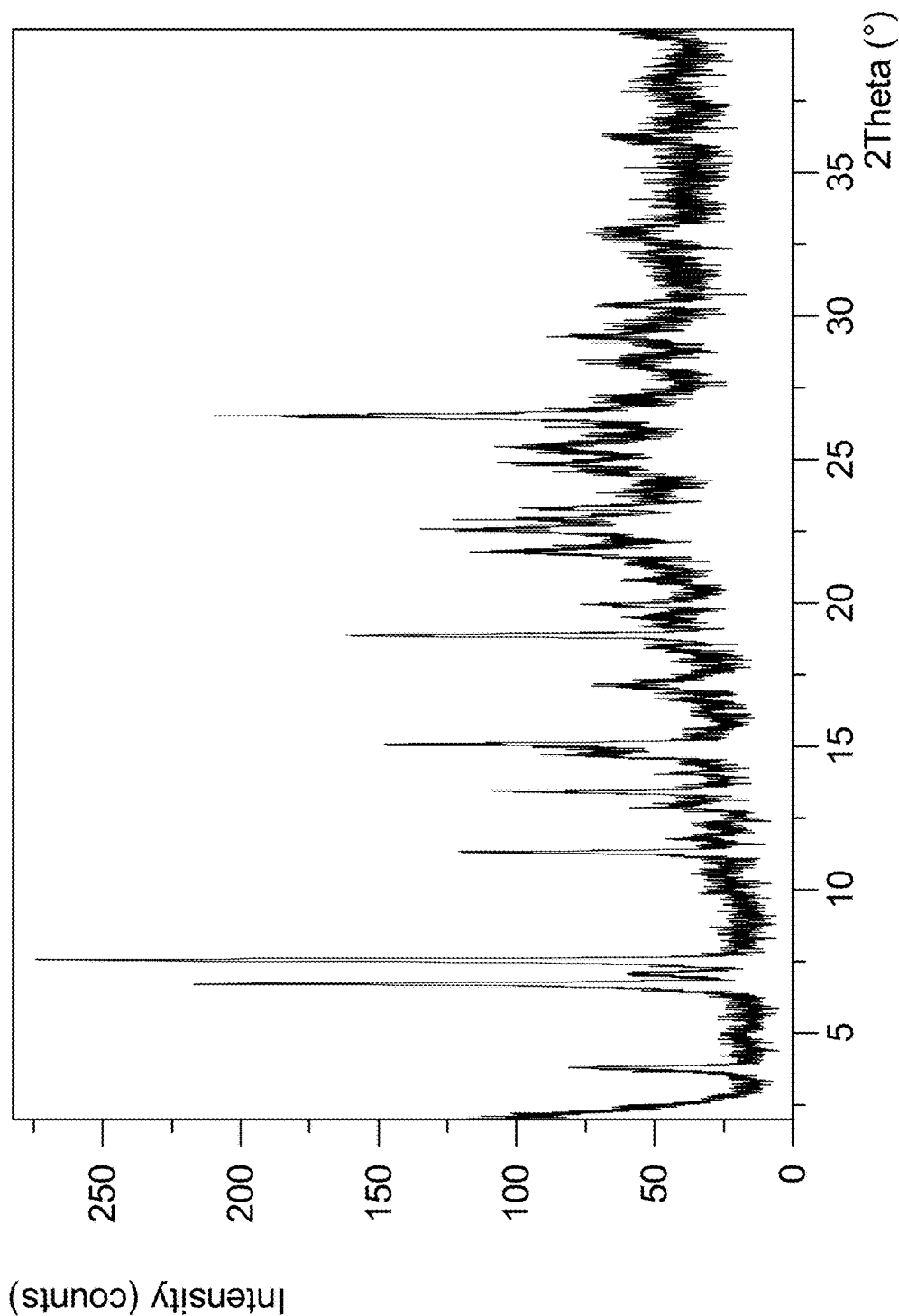
FIG. 41 shows a X-ray powder diffraction (XRPD) of Compound I bis-HBr Form XVIII.

Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate bis-hydrobromide (Compound I bis-HBr Form XVIII) is characterized by an X-ray powder diffractogram comprising the following peaks: 6.7, 7.6, and 18.9°2θ±0.2°2θ, as determined on a diffractometer using Cu—Kα radiation at a wavelength of 1.5406 Å. The diffractogram comprises additional peaks at 11.3, 15.1, and 21.8°2θ±0.2°2θ. Compound I bis-HBr Form XVIII is also characterized by its full X-ray powder diffractogram as substantially as shown in FIG. 41.

Figure 42:
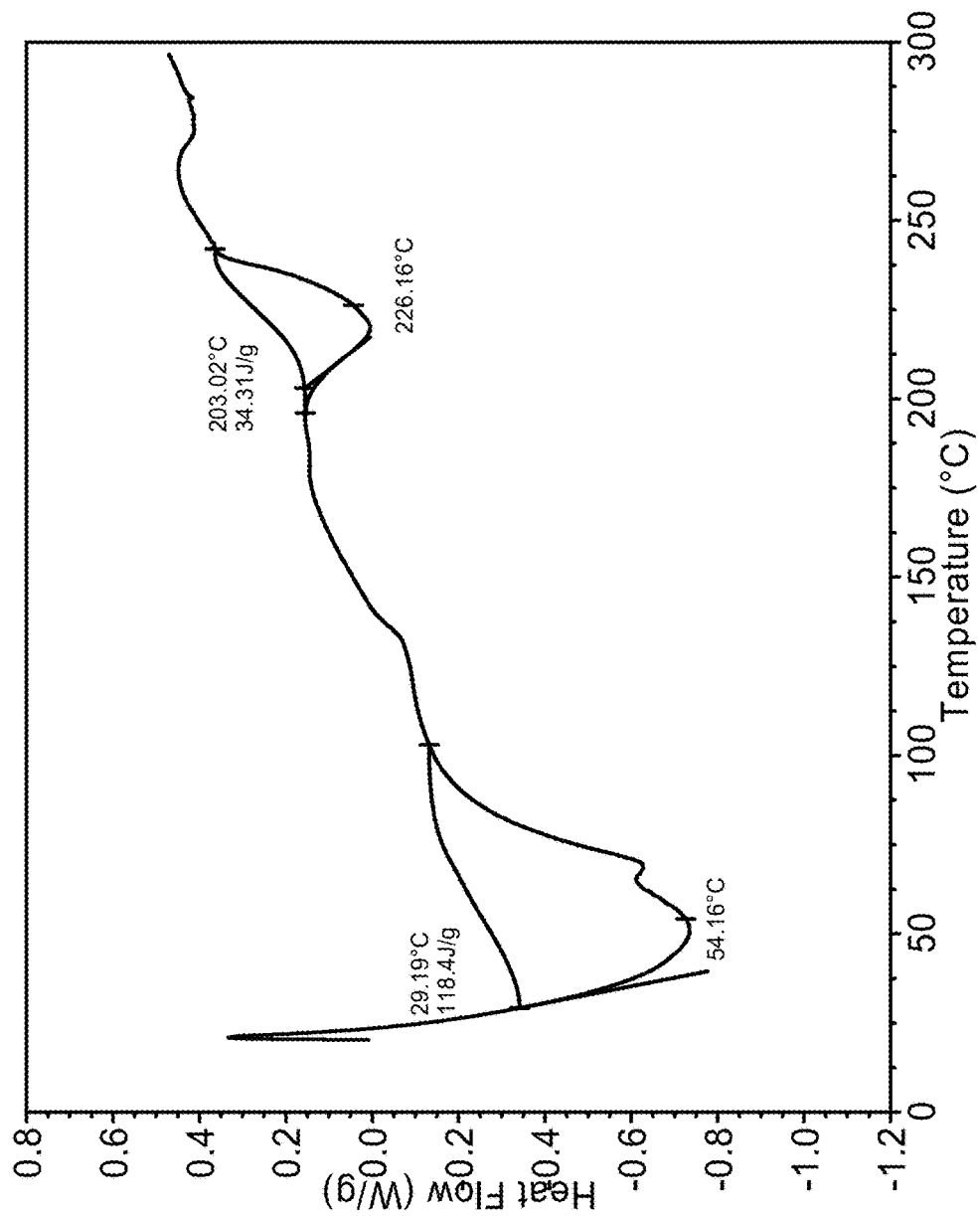
FIG. 42 shows differential scanning calorimeter (DSC) curve of Compound I bis-HBr Form XVIII.

In some embodiments, Compound I bis-HBr Form XVIII is characterized by a differential scanning calorimetry (DSC) curve that comprises an endotherm at about 203° C. Compound I bis-HBr Form XVIII is also characterized by its full DSC curve as substantially as shown in FIG. 42.

Methods of Use

The solid forms of Compound I described herein are administered for treatment of HCV. Administration routes include, for example, those described in any patents and patent applications incorporated by reference, such as rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

Oral administration can be carried out by delivering any of the Compound I forms by capsule or enteric coated tablets, or the like.

The compounds are preferably formulated in a unit dosage form. The term "unit dosage forms" refers to physically discrete units suitable as unitary dosages for human subjects and other mammals, each unit containing a predetermined quantity of active material calculated to produce the desired therapeutic effect. The compounds are generally administered in a pharmaceutically effective amount.

For oral administration, each dosage unit typically contains from 0.1 mg to 2 g of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

In one embodiment, an active ingredient (i.e., Compound I, and salts and complexes of Compound I, as described herein) or pharmaceutical composition comprising the active ingredient are effective in treating one or more of genotype 1 HCV infected subjects, genotype 2 HCV infected subjects, genotype 3 HCV infected subjects, genotype 4 HCV infected subjects, genotype 5 HCV infected subjects, and/or genotype 6 HCV infected subjects. In one embodiment, the active ingredient or pharmaceutical composition comprising the active ingredient are effective in treating genotype 1 HCV infected subjects, including genotype 1a and/or genotype 1b. In another embodiment, the active ingredient or pharmaceutical composition comprising the active ingredient are effective in treating genotype 2 HCV infected subjects, including genotype 2a, genotype 2b, genotype 2c and/or genotype 2d. In another embodiment, the active ingredient or pharmaceutical composition comprising the active ingredient are effective in treating genotype 3 HCV infected subjects, including genotype 3a, genotype 3b, genotype 3c, genotype 3d, genotype 3e and/or genotype 3f. In another embodiment, the active ingredient or pharmaceutical composition comprising the active ingredient are effective in treating genotype 4 HCV infected subjects, including genotype 4a, genotype 4b, genotype 4c, genotype 4d, genotype 4e, genotype 4f, genotype 4g, genotype 4h, genotype 4i and/or genotype 4j. In another embodiment, the active ingredient or pharmaceutical composition comprising the active ingredient are effective in treating genotype 5 HCV infected subjects, including genotype 5a. In another embodiment, the active ingredient or pharmaceutical composition comprising the active ingredient effective in treating genotype 6 HCV infected subjects, including genotype 6a.

In some embodiments, the active ingredient or pharmaceutical composition comprising the active ingredient is administered, either alone or in combination with one or more therapeutic agent(s) for treating HCV (such as a HCV NS3 protease inhibitor or an inhibitor of HCV NS5B polymerase), for about 24 weeks, for about 16 weeks, or for about 12 weeks, or less. In further embodiments, the active ingredient or pharmaceutical composition comprising the active ingredient is administered, either alone or in combination with one or more therapeutic agent(s) for treating HCV (such as a HCV NS3 protease inhibitor or an inhibitor of HCV NS5B polymerase), for about 24 weeks or less, about 22 weeks or less, about 20 weeks or less, about 18 weeks or less, about 16 weeks or less, about 12 weeks or less, about 10 weeks or less, about 8 weeks or less, or about 6 weeks or less or about 4 weeks or less. The active ingredient or pharmaceutical composition comprising the active ingredient may be administered once daily, twice daily, once every other day, two times a week, three times a week, four times a week, or five times a week.

In further embodiments, a sustained virologic response is achieved at about 4 weeks, 6 weeks, 8 weeks, 12 weeks, or 16 weeks, or at about 20 weeks, or at about 24 weeks, or at about 4 months, or at about 5 months, or at about 6 months, or at about 1 year, or at about 2 years.

EXAMPLES

Example 1. Stable Form Screens

Compound I can be synthesized according to the methods described in WO 2013/075029 or U.S. Provisional Application No. 62/010,813 (filed concurrently herewith and titled "Processes for Preparing Antiviral Compounds"), both of which are incorporated by reference in their entirety. A stable form screen was performed in an attempt to obtain a crystalline form of Compound I using 10 to 20 volumes of the primary solvent and 5 to 10 volumes of anti-solvent (if applicable).

1.1 Compound I Form I

An additional stable form screen was performed using the same procedure as described above but included a crystalline intermediate (Compound II shown below) as seeds.

Compound II

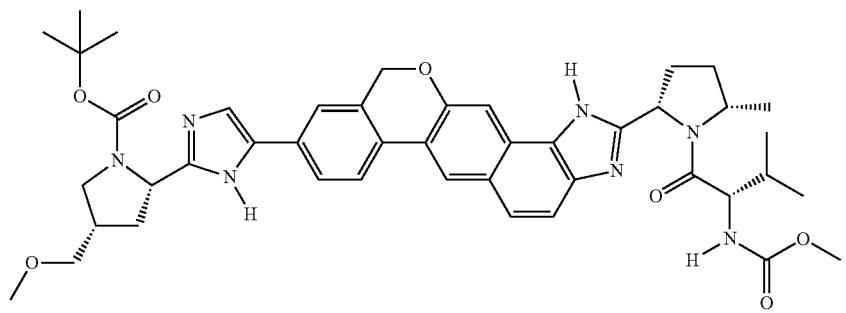

Compound II can be synthesized according to the methods described in WO 2013/075029 or U.S. Provisional Application No. 62/010,813. Needle-like particles were formed in butyronitrile, propionitrile, MEK/toluene, MEK/IPE and 2-pentanone/toluene. XRPD patterns of the wet solids were mostly consistent with each other with minor shifting in the peaks. The new form is named Compound I Form I, which is believed to be isostructural channel solvates with the respective solvents. After air drying all solids afforded amorphous XRPD patterns.

Another stable form screen was performed using carbon (Darco G-60) treated Compound I, solvents, antisolvent (diisopropyl ether (IPE)), and seeds of Compound I Form I. This screen afforded crystalline solids from additional solvents as summarized in Table 1. The XRPD patterns of all of these solvates are consistent with Form I. The solvates were observed to convert to amorphous solids after drying. The XRPD patterns of Compound I were obtained in the experimental setting as follows: 45 kV, 40 mA, K$\alpha$1=1.5406 Å, scan range 2-40°, step size 0.0167°, counting time: 15.875 s.

TABLE 1

Stable form screen of carbon treated Compound I

| Solvents | PLM | Comments |
|---|---|---|
| Water | Amorphous | Slurry |
| Water/EtOH | Amorphous | Sticky phase coating |
| ACN/IPE | Birefringent | Slurry of needles |
| MeOH/IPE | Solution | Seeds dissolved |
| EtOH/IPE | Solution | Seeds dissolved |
| Acetone/IPE | Birefringent | Thick slurry of needles |
| IPA/IPE | Amorphous | Sticky coating |
| MEK/IPE | Birefringent | Thick slurry of needles |
| MIBK/IPE | Birefringent | White paste |
| DCM/IPE | Birefringent | Thick slurry of small needles |
| THF/IPE | Solution | Seeds dissolved |
| 2-MeTHF/IPE | Amorphous | slurry |
| EtOAc/IPE | Birefringent | Thick slurry of needles |
| IPAc/IPE | Amorphous | slurry |
| Toluene | Amorphous | Sticky coating |

The crystallinity of Compound I Form I can be improved by using a butyronitrile/butyl ether (BN/BE) mixture according to the following procedure.

The crystallization experiment was started with 40 to 75 mg Compound I in 1.1 to 3.0 mL of a BN/BE in a ratio of 7:4 (anhydrous solvents). The sample was held at RT over $P_2O_5$ for 23 days without agitation, and crystals formed in the solution. Afterwards, the liquid phase was replaced with butyl ether and the solids were obtained by centrifuge. These solids, corresponding to Compound I Form I, were used for the subsequent step as seed.

Purified Compound I (709.8 mg) was prepared from reflux of ethanol solution with Darco G-60 and was added to a new vial via a filter. While stirring, 7 mL of anhydrous butyronitrile (BN) was added. A clear orange solution was obtained. While stirring, 4 mL of anhydrous butyl ether (BE) was added slowly. To the solution was added 7.7 mg of Compound I Form I (from previous BN:BE crystallization experiment) as seed. The solution became cloudy and the seeds did not dissolve. The sample was stirred for ~10 minutes before the agitation was stopped. The vial was capped and placed into a jar with some $P_2O_5$ solids at room temperature. After 6 days, a thin layer of bright yellow precipitate was observed on the wall and the bottom of the vial. The liquid phase was withdrawn and 3 mL of anhydrous butyl ether was added. Solids were scraped down with a spatula from the vial. The suspension was heated to about 30° C. for over half hour period and was held for ~1 hour before cooling to 20° C. at about 0.1° C./min (without agitation). The sample was stored in a jar with $P_2O_5$ solids for 5 days. The sample was vacuum filtered using 0.22 μm nylon filter, washed with 2×200 μL of anhydrous butyl ether, and air dried under reduced pressure for about 5 minutes.

XRPD analysis of the sample showed good very sharp peaks as shown in FIG. 1. The XRPD analysis setting was as follows: 45 kV, 40 mA, K$\alpha$1=1.5406 Å, scan range 1-40°, step size 0.0167°, counting time: 36.83 s. The characteristic peaks of crystalline Compound I Form I include: 2.9, 3.6, 4.8, 5.2, 6.0°2θ (FIG. 1). The XRPD pattern of Form I was successfully indexed, indicating that Form I is composed primarily of a single crystalline phase. Extremely large unit cell volume containing up to ~60 API molecules in the unit cell was observed. The amorphous halo observed in the XRPD pattern could be a result of the size of the unit cell. Butyl ether stoichiometry could not be estimated. Two alternative indexing solutions were found: monoclinic and orthorhombic.

Figure 3:
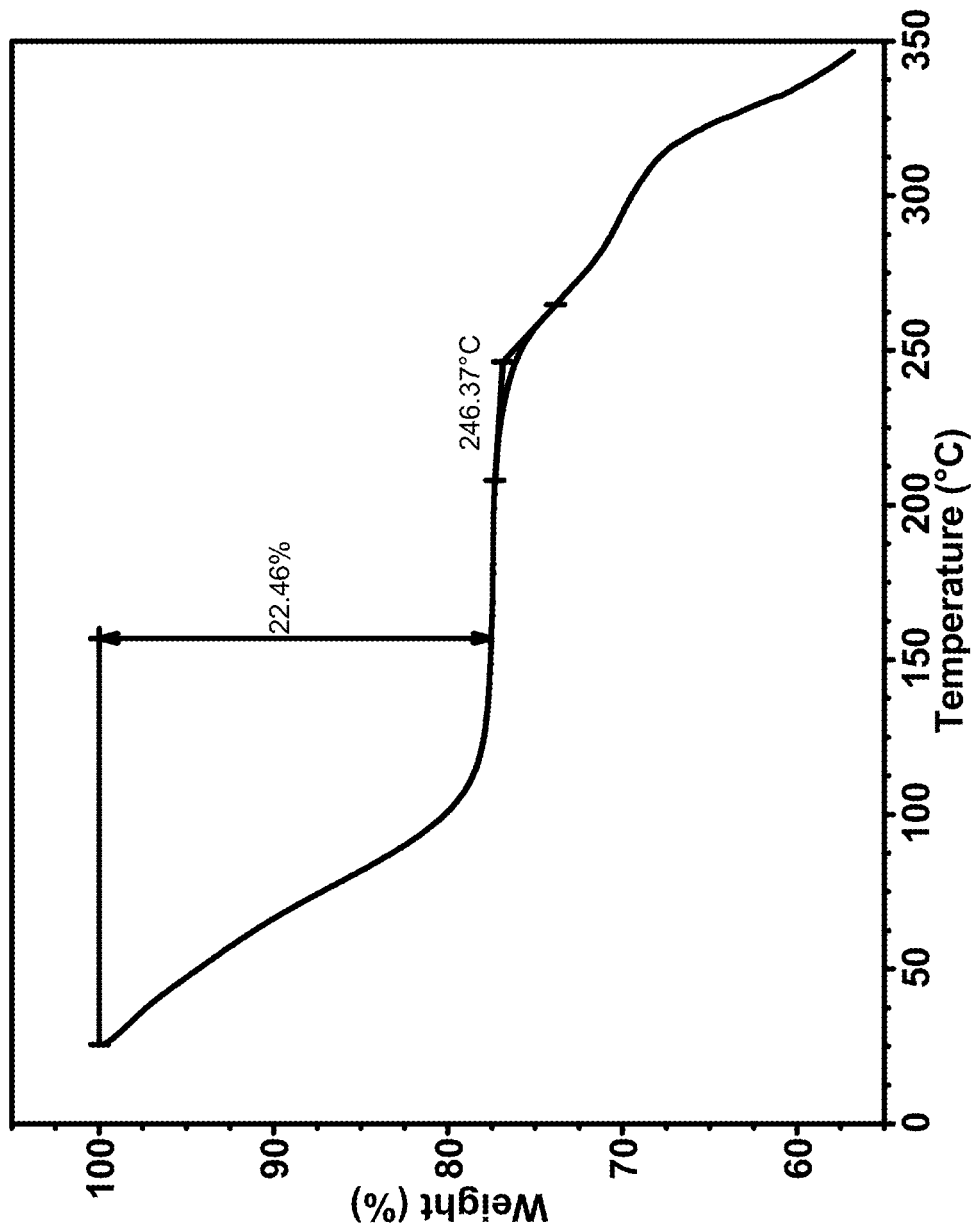
FIG. 3 shows a thermogravimetric analysis (TGA) of Compound I Form I.

DSC and TGA data confirmed that Form I is a solvated form. DSC shows a broad endotherm with onset at 109° C. and small endotherm with onset at 177° C. (FIG. 2). TGA shows 22% weight loss below 150° C. (FIG. 3).

Example 2. Compound I Salt/Co-Crystal Screens

Salt/co-crystal screens afforded four crystalline salts or complexes with hydrochloric acid, phosphoric acid, L-tartaric acid, and hydrobromic acid. Among those salts, Compound I bis-HCl has several crystalline and mesophase forms, Compound I Phosphate has eight unique XRPD patterns, Compound I L-tartrate has two unique XRPD patterns, and Compound I bis-HBr has one crystalline form.

2.1 Compound I bis-HCl

Figure 44:
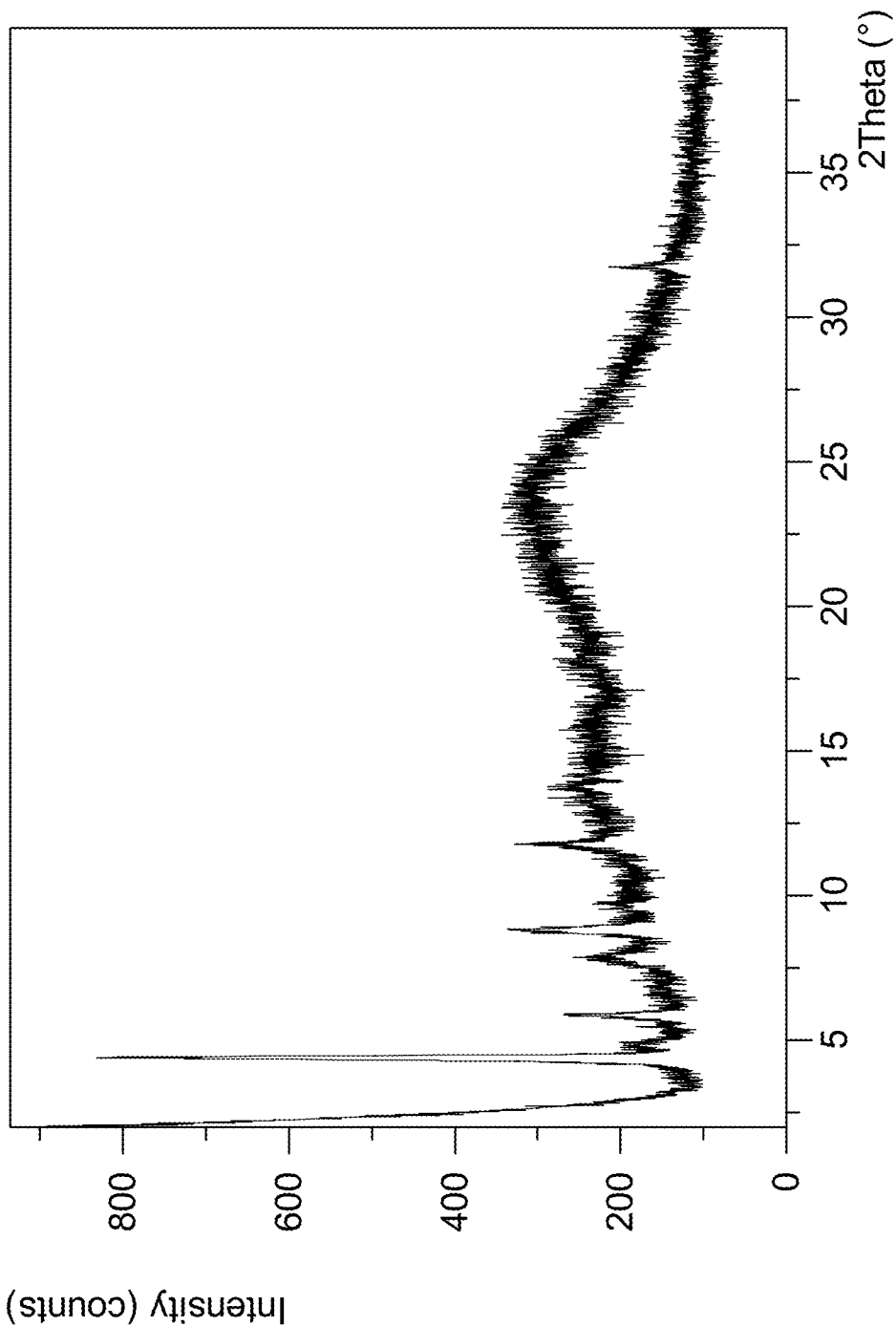
FIG. 44 shows a X-ray powder diffraction (XRPD) of mesophase Compound I bis-HCl solids from acetone. The peak at 32°2° is from NaCl impurity.
Figure 45:
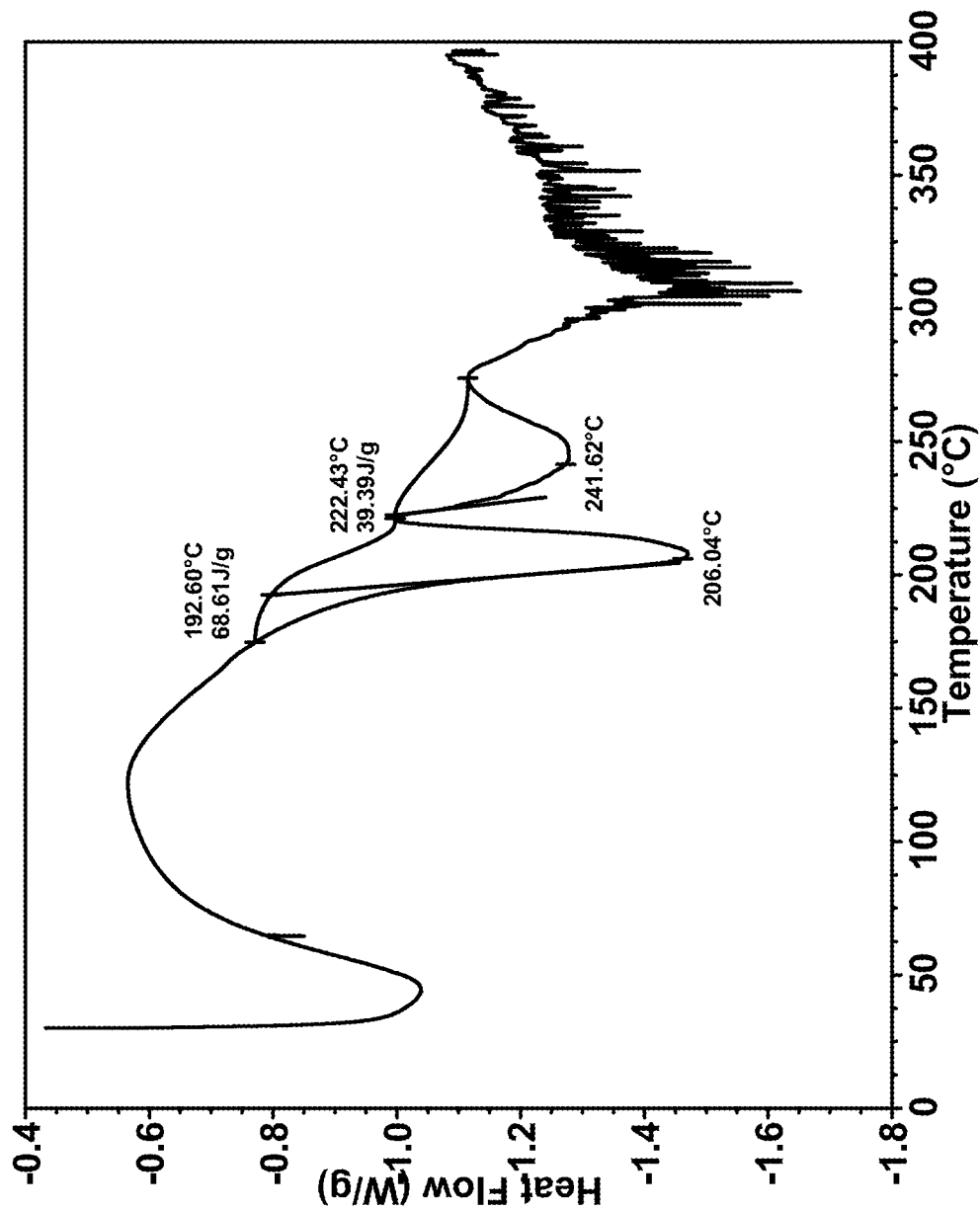
FIG. 45 shows a differential scanning calorimeter (DSC) curve of mesophase Compound I bis-HCl from acetone (dried under vacuum at room temperature).
Figure 46:
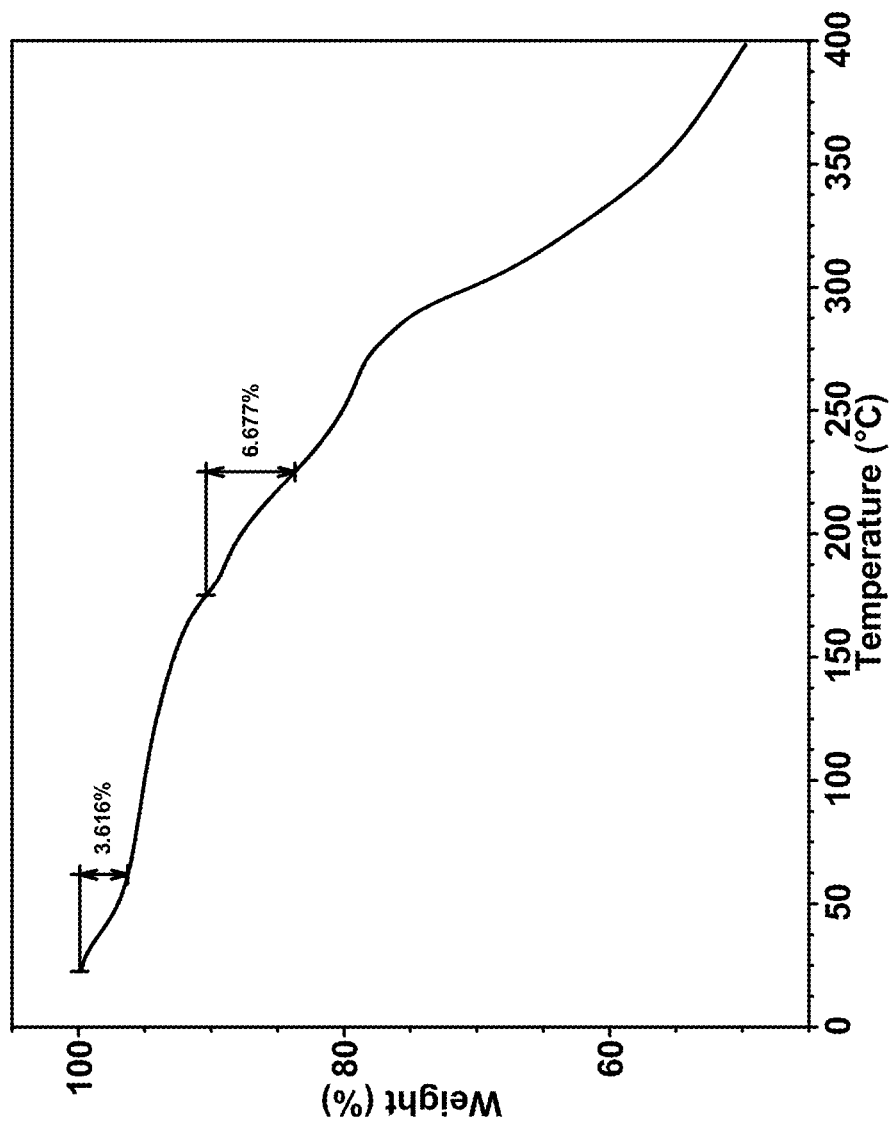
FIG. 46 shows a thermogravimetric analysis (TGA) of mesophase Compound I bis-HCl from acetone (dried under vacuum at room temperature).

The mesophase solids were obtained from acetonitrile during salt formation using 10 volumes of solvent and 2 equivalents of HCl. Re-slurry of this mesophase material in acetone (10 volumes) afforded plate crystals. However, XRPD showed that although the solids from acetone (FIG. 44) had more peaks in the XRPD pattern than those from acetonitrile, the intensity and number of the peaks do not meet the expectation for crystals, and it is therefore still considered a mesophase. These XRPD patterns were obtained in the experimental setting as follows: 45 kV, 40 mA, K$\alpha$1=1.5406 Å, scan range 2-40°, step size 0.0084°, counting time: 8.26 s. The DSC analysis of Compound I bis-HCl from acetone was conducted using 10° C./min heating rate over the range of 25-400° C. and showed multiple endothermic events (FIG. 45). The TGA data of Compound I bis-HCl from acetone were obtained using 10° C./min heating rate over the range of 25-400° C. and showed 3.6% weight loss below 60° C. and 6.7% weight loss at 170-220° C. (FIG. 46).

Figure 47:
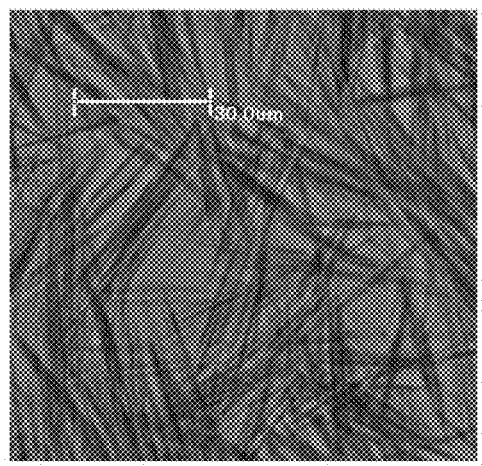
FIG. 47 shows a Polarized Light Microscopy (PLM) of Compound I bis-HCl Form II (MeOH solvate) (top left panel); Compound I bis-HCl Form III (EtOH solvate) (bottom left panel); Compound I bis-HCl Form IV (1-propanol solvate) (top right panel); and Compound I bis-HCl Form V (EtOH solvate) (bottom right panel).
Figure 47:
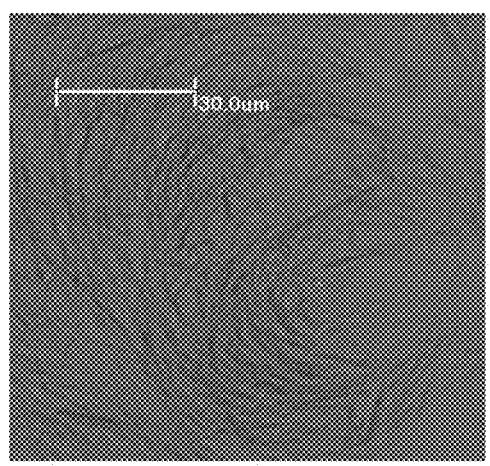
Figure 47:
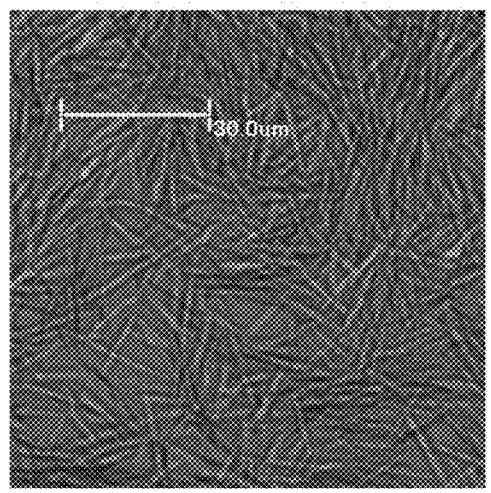
Figure 47:
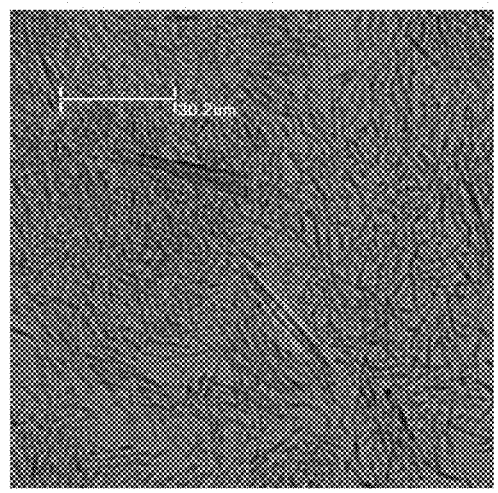

The stable form screen of Compound I bis-HCl was performed using 20 solvents (5-10 volumes) in an attempt to discover all crystalline forms, as summarized in Table 2. Four crystalline solvates were discovered in the slurries, which utilized alcohols such as methanol, ethanol and 1-propanol. With ethanol, the initial precipitation was Compound I bis-HCl Form III solids; after stirring for two weeks, the solids became Compound I bis-HCl Form V. The shapes of these crystals appeared as needles, shown in FIG. 47. After vacuum drying, these solvates lost solvents easily and changed to Compound I bis-HCl Form VI. As a desolvated form, Compound I bis-HCl Form VI absorbs water quickly when in contact with air. For example, Compound I bis-HCl Form VI contains 8.8% water by KF after drying the methanol solvate and contains 5.2% water after drying the ethanol solvate. Each form was characterized by XRFD, DSC and TGA (FIGS. 4-19). TGA and DSC analysis were conducted after the samples were dried at room temperature in vacuum oven for 1 hour.

2.1.2 Compound I bis-HCl Form III

Crystalline Compound I bis-HCl Form III was obtained from EtOH slurry (10 volumes). The following procedure was used to scale-up this form: a solution of Compound I (1.0 g) in ethanol (12.5 ml) was mixed with 37% HCl (0.28 ml) at 45° C. followed by adding Compound I bis-HCl Form III seeds (5 mg), which were prepared according to the method described in Section 2.1 above. The mixture was cooled from 45° C. to 20° C. The solids were isolated by

TABLE 2

Results from Stable Form Screen of Compound I bis-HCl

| Solvent | Initial form | Solubility (mg/ml) | Final form | Notes |
|---|---|---|---|---|
| Water | Solution | <1 | Amorphous | |
| EtOH/water | Solution | >20 | Solution | |
| ACN | Mesophase | | Mesophase | Gel |
| MeOH | Compound I bis-HCl Form II | 50 | Compound I bis-HCl Form II | Crystalline |
| EtOH | Compound I bis-HCl Form III | 9 | Compound I bis-HCl Form V | Crystalline; Compound I bis-HCl Form III and Compound I bis-HCl Form V converted to Compound I bis-HCl Form II after vacuum drying at room temperature |
| IPA | Mesophase | | Mesophase | Gel |
| 1-Propanol | Compound I bis-HCl Form IV | 9 | Compound I bis-HCl Form IV | Crystalline; Compound I bis-HCl Form IV converted to Compound I bis-HCl Form II after vacuum drying at room temperature |
| 1-Butanol | Mesophase | | Mesophase | Gel like mesophase |
| 2-Butanol | Solution | >50 | Solution | |
| Acetone | Mesophase | 6 | Mesophase | Mesophase |
| MEK | Amorphous | | Amorphous | |
| MIBK | Mesophase | <1 | Mesophase | Mesophase |
| DCM | Solution | >20 | Solution | Amorphous after adding heptane |
| THF | Solution | | Solution | Mesophase after adding heptane |
| 2-MeTHF | Amorphous | | Amorphous | |
| Ethyl acetate | Mesophase | <1 | Mesophase | Mesophase |
| IPAc | Mesophase | <1 | Mesophase | Mesophase |
| MTBE | Amorphous | <1 | Amorphous | |
| Toluene | Mesophase | <1 | Mesophase | Mesophase |
| heptane | Amorphous | <1 | Amorphous | |

2.1.1 Compound I bis-HCl Form II

Crystalline Compound I bis-HCl Form II was obtained from MeOH slurry (10 volumes). The XRPD analysis was performed while covering the sample with a kapton film to prevent solvent evaporation. The XRPD experimental settings are: 45 kV, 40 mA, Kα1=1.5406 Å, scan range 2-40°, step size 0.0084°, counting time: 8.26 s. The characteristic peaks of Compound I bis-HCl Form II include: 3.6, 6.1, 7.3, 9.6, 10.9°2θ (FIG. 4).

The DSC analysis was conducted using 2.1 mg of Compound I bis-HCl Form II sample and at a heating rate of 10° C./min over the range of 20-300° C. (FIG. 5). DSC thermogram showed multiple endothermic events including solvent loss below 100° C. and melting point with onset at 186° C.

Figure 6:
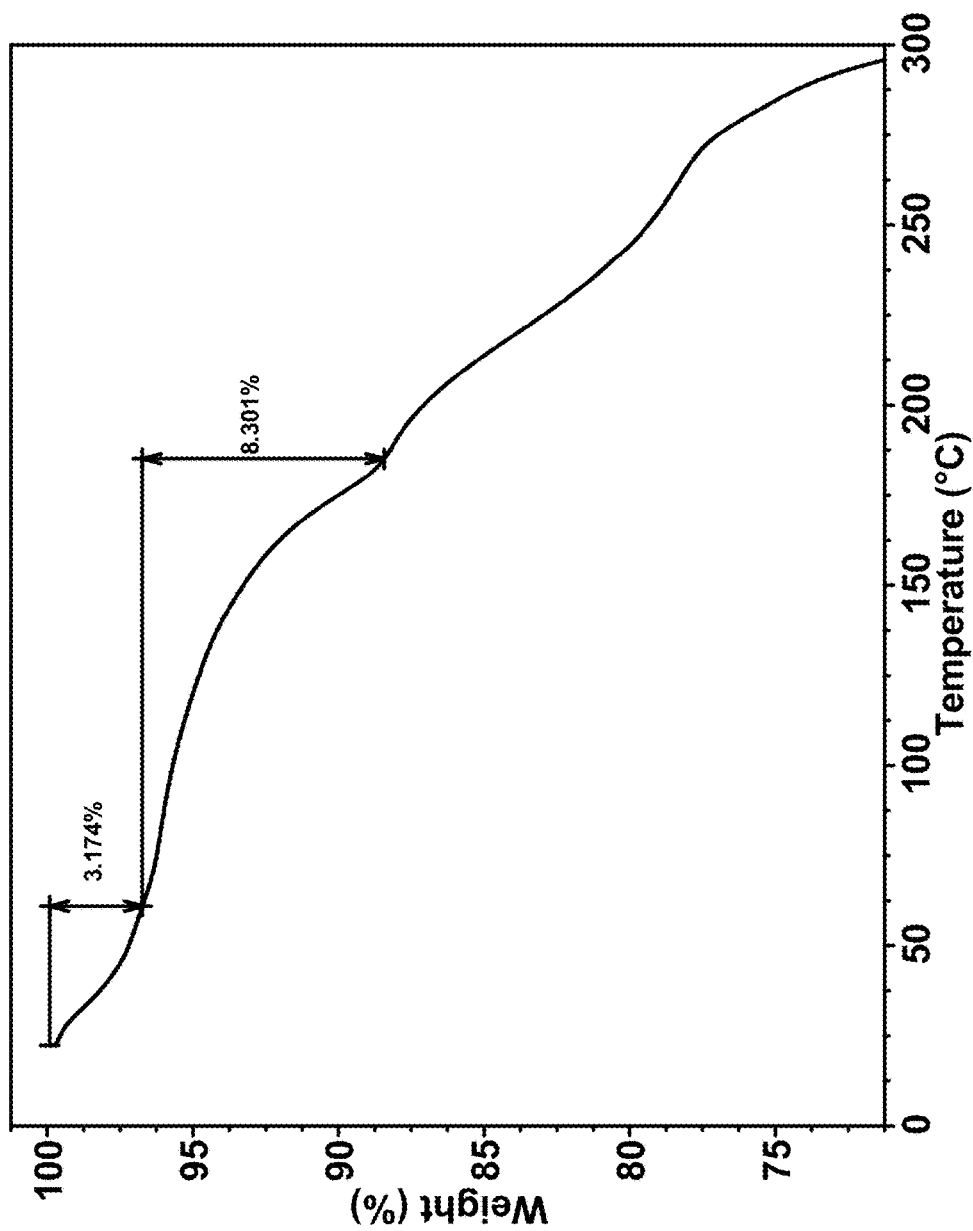
FIG. 6 shows a thermogravimetric analysis (TGA) of Compound I bis-HCl Form II.

The TGA data were obtained using 1.2 mg Compound I bis-HCl Form II and at a heating rate of 10° C./min over the range of 20-300° C. (FIG. 6). TGA thermogram of Compound I bis-HCl Form II showed 3.2% weight loss below 60° C. and 8.3% weight loss at 60-190° C. Thermal data suggest that Compound I bis-HCl Form II is a methanol solvate.

filtration, rinsed with ethanol (2×2 ml) and dried to afford Compound I bis-HCl Form III (0.91 g)

The XRPD analysis was performed using the following experimental setting: 45 kV, 40 mA, Kα1=1.5406 Å, scan range 2-40°, step size 0.0084°, counting time: 8.26 s. The characteristic peaks of Compound I bis-HCl Form III include: 3.8, 7.2, 7.6, 11.4°2θ (FIG. 7).

The DSC analysis was conducted using 2.1 mg of Compound I bis-HCl Form III sample and a heating rate of 10° C./min over the range of 20-300° C. (FIG. 8). DSC thermogram showed multiple endothermic events including solvent loss below 100° C. and melting with onset at 189° C.

Figure 9:
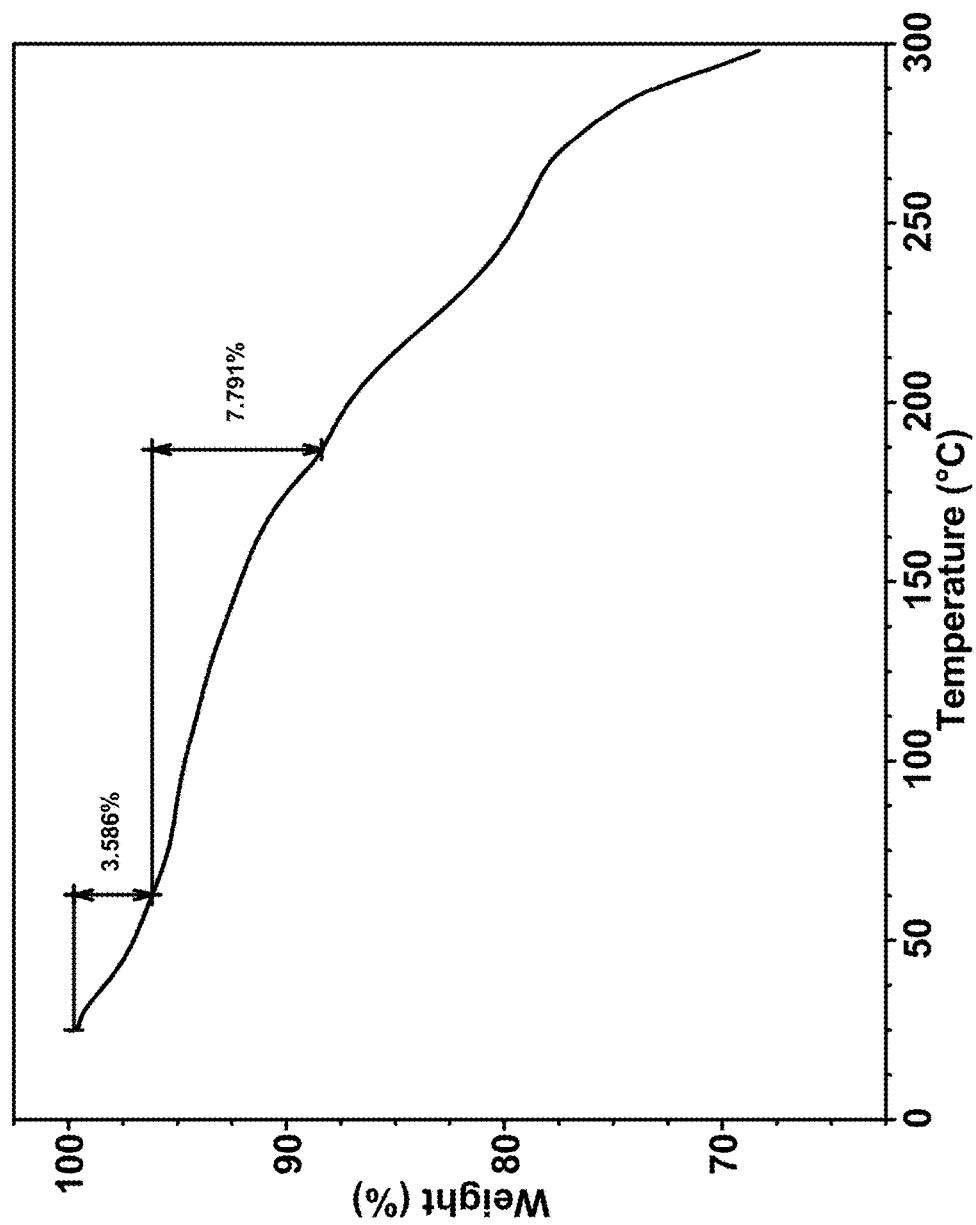
FIG. 9 shows a thermogravimetric analysis (TGA) of Compound I bis-HCl Form III.

The TGA data were obtained using 1.2 mg Compound I bis-HCl Form III and at a heating rate of 10° C./min over the range of 20-300° C. (FIG. 9). TGA thermogram of Compound I bis-HCl Form III showed 3.6% weight loss below 60° C. and 7.8% weight loss at 60-190° C. Thermoanalysis data suggest that Compound I bis-HCl Form III is an ethanol solvate.

2.1.3 Compound I bis-HCl Form IV

Crystalline Compound I bis-HCl Form IV was obtained from 1-propanol slurry (10 volumes). The XRPD analysis was performed using the following experimental setting: 45 kV, 40 mA, Kα1=1.5406 Å, scan range 2-40°, step size 0.0084°, counting time: 8.26 s. The characteristic peaks of Compound I bis-HCl Form IV include: 3.7, 7.5, 9.8, 11.2, 14.5°2θ (FIG. 10).

The DSC analysis was conducted using 3.4 mg of Compound I bis-HCl Form IV sample and at a heating rate of 10° C./min over the range of 20-300° C. (FIG. 11). DSC thermogram showed multiple endothermic events including solvent loss below 100° C. and melting with onset at 193° C.

Figure 12:
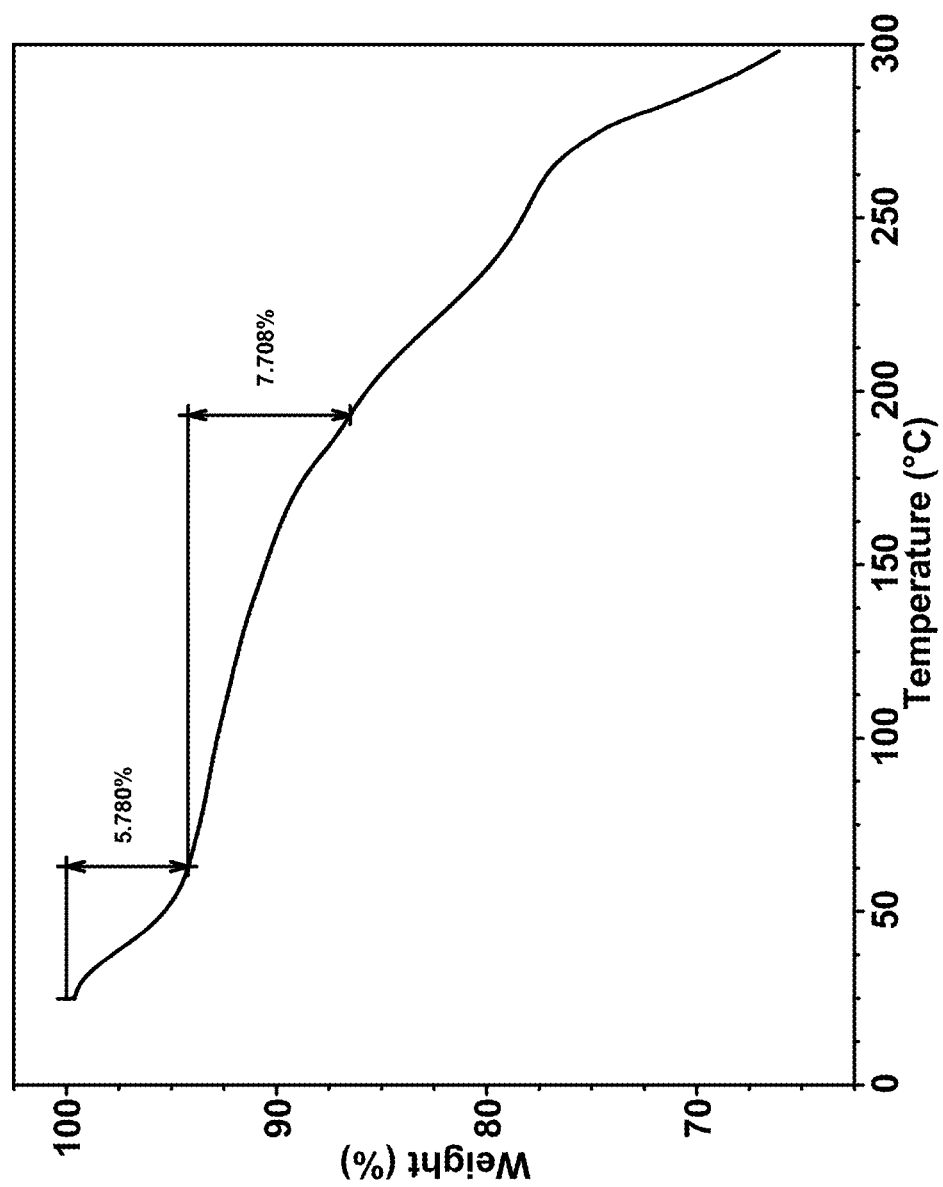
FIG. 12 shows a thermogravimetric analysis (TGA) of Compound I bis-HCl Form IV.

The TGA data were obtained using 3.5 mg Compound I bis-HCl Form IV and at a heating rate of 10° C./min over the range of 20-300° C. (FIG. 12). TGA thermogram of Compound I bis-HCl Form IV showed 5.8% weight loss below 60° C. and 7.7% weight loss at 60-190° C. Thermoanalysis data suggest that Compound I bis-HCl Form IV is a 1-propanol solvate.

2.1.4 Compound I bis-HCl Form V

Crystalline Compound I bis-HCl Form V was obtained from EtOH slurry (10 volumes) after two weeks. The XRPD analysis was performed using the following experimental setting: 45 kV, 40 mA, Kα1=1.5406 Å, scan range 2-40°, step size 0.0084°, counting time: 8.26 s. The characteristic peaks of Compound I bis-HCl Form V include: 6.3, 7.1, 10.6, 12.6, 14.1°2θ (FIG. 13).

The DSC analysis was conducted using 2.1 mg of Compound I bis-HCl Form V sample and at a heating rate of 10° C./min over the range of 20-300° C. (FIG. 14). DSC thermogram showed multiple endothermic events including solvent loss below 100° C. and melting with onset at 188° C.

Figure 15:
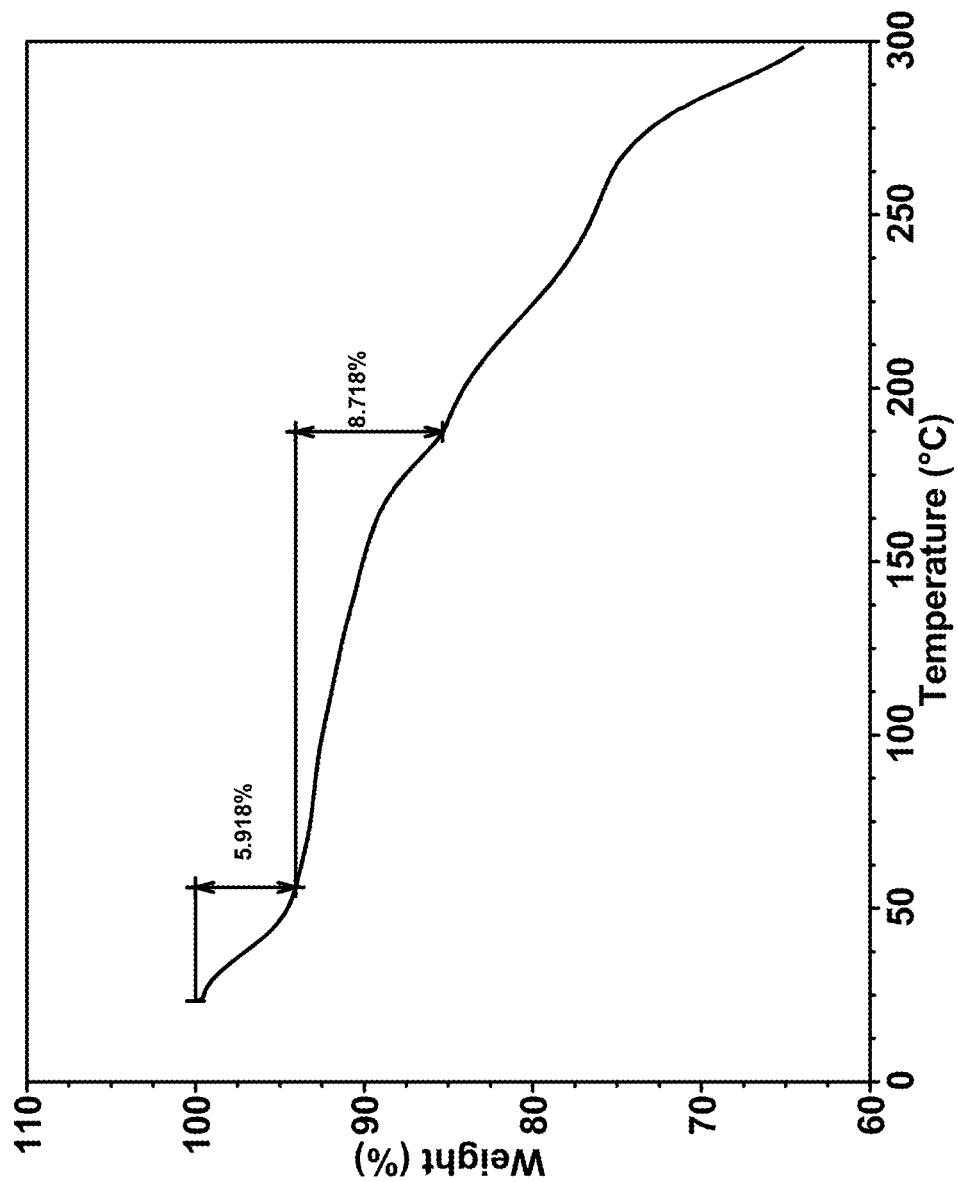
FIG. 15 shows a thermogravimetric analysis (TGA) of Compound I bis-HCl Form V.

The TGA data were obtained using 2.2 mg Compound I bis-HCl Form V and at a heating rate of 10° C./min over the range of 20-300° C. (FIG. 15). TGA thermogram of Compound I bis-HCl Form V showed 5.9% weight loss below 60° C. and 8.7% weight loss at 60-190° C. Thermoanalysis data suggest that Compound I bis-HCl Form V is an ethanol solvate.

2.1.5 Compound I bis-HCl Form VI

Crystalline Compound I bis-HCl Form VI was obtained after drying solvated Forms II through V. The XRPD analysis of Compound I bis-HCl Form VI was performed using the following experimental setting: 45 kV, 40 mA, Kα1=1.5406 Å, scan range 2-40°, step size 0.0167°, counting time: 15.875 s. The characteristic peaks of Compound I bis-HCl Form VI include: 3.8, 6.7, 7.6, 11.4°2θ (FIG. 16).

The DSC analysis was conducted using 1.4 mg of Compound I bis-HCl Form VI sample and at a heating rate of 10° C./min over the range of 20-300° C. (FIG. 17). DSC thermogram showed two broad endothermic events including solvent loss below 100° C. and melting with onset at 205° C.

Figure 18:
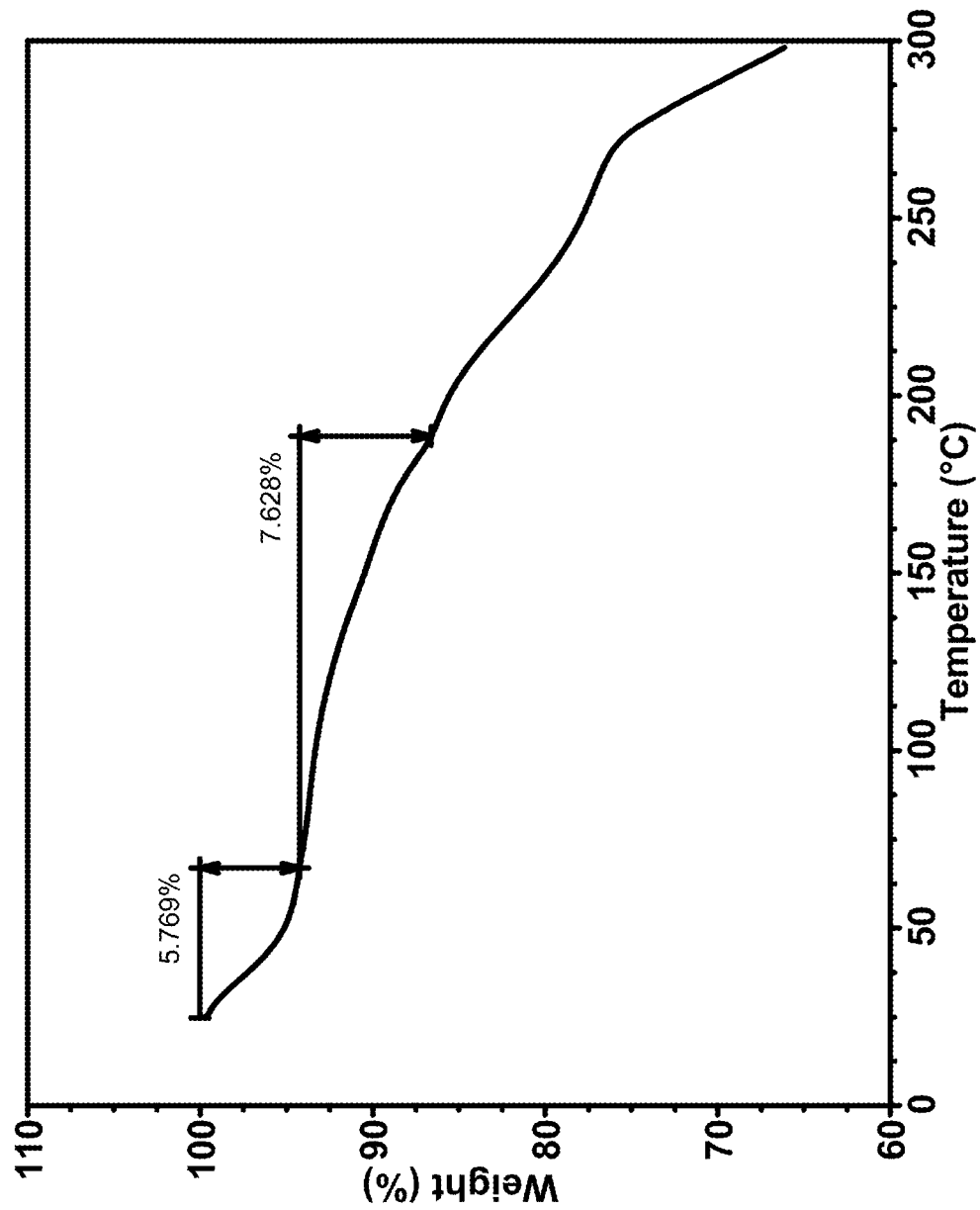
FIG. 18 shows a thermogravimetric analysis (TGA) of Compound I bis-HCl Form VI.
Figure 19:
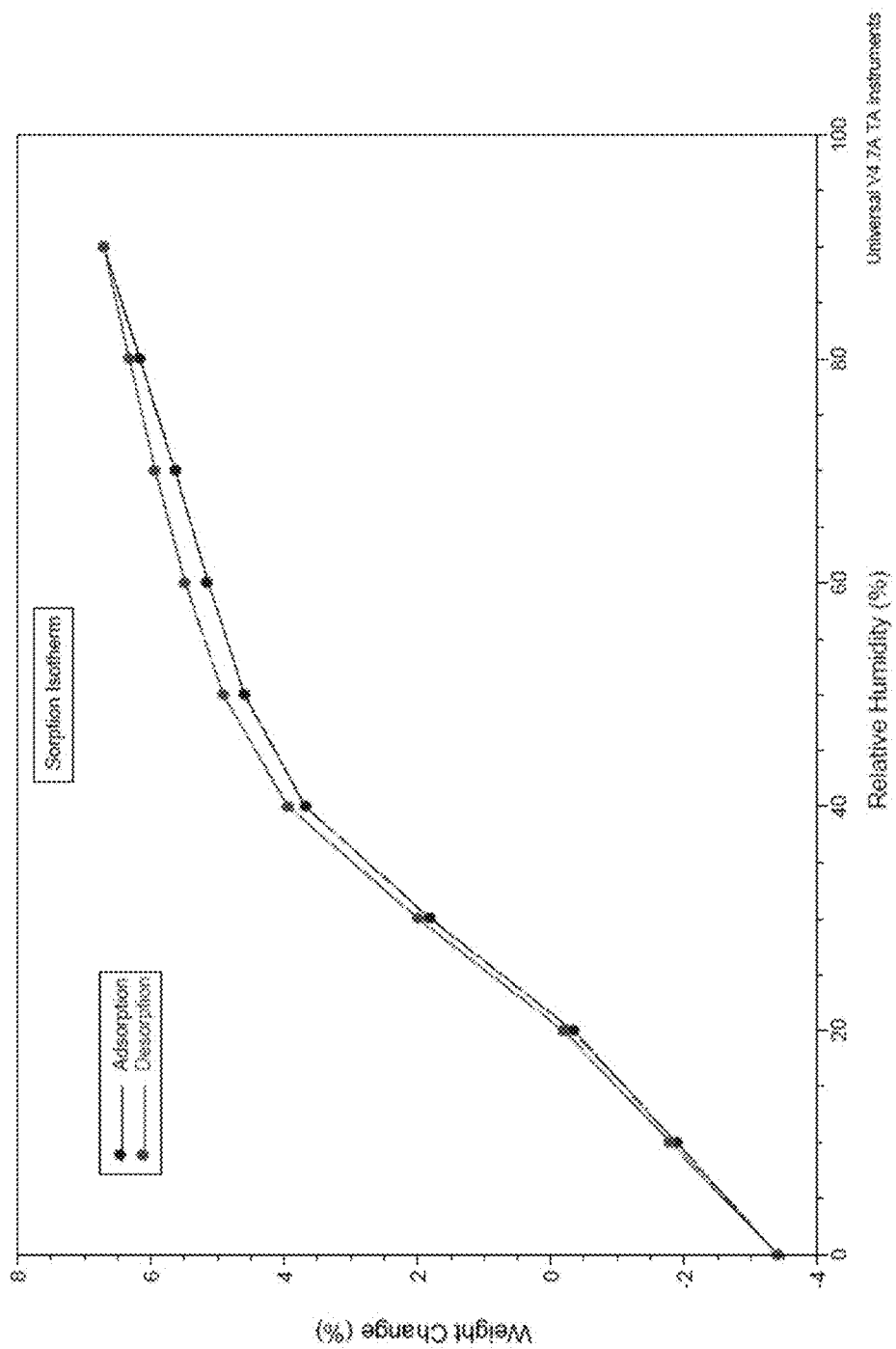
FIG. 19 shows a dynamic vapor sorption (DVS) curve of Compound I bis-HCl Form VI.

The TGA data were obtained using 2.2 mg Compound I bis-HCl Form VI and at a heating rate of 10° C./min over the range of 20-300° C. (FIG. 18). TGA thermogram of Compound I bis-HCl Form VI showed 5.8% weight loss below 60° C. and 7.6% weight loss at 60-190° C. KF analysis showed 5.2% water. DVS analysis showed this form is hygroscopic, which explains the water content of 5.2% (FIG. 19).

2.2 Compound I Phosphate

Crystalline Compound I Phosphate Form VII was first obtained from EtOH/water solution with significant excess of phosphoric acid (10 equivalents). Eight crystalline forms were found later (Table 3) in the stable form screening. Compound I Phosphate Form VII was observed in the wet solids from EtOH/water, and was converted to Compound I Phosphate Form VIII upon vacuum drying. Compound I Phosphate Form IX was obtained after air drying of Form VII. Compound I Phosphate Form X was formed by slurrying for 2 weeks either in water or in a solution of water and ethanol of 0.9 water activity. This Form converted to Compound I Phosphate Form XI after drying. Compound I Phosphate Form XII was obtained from methanol, and had the same XRPD pattern after drying. Compound I Phosphate Form XIII was formed in acetone or MEK, and it converted to Compound I Phosphate Form VIII upon drying. Compound I Phosphate Form XIV was obtained from 9:1 acetone/water mixture or 10:1 2-MeTHF/water mixture, and had the same XRPD pattern upon air drying. Most of these forms were found to be hydrates except for Compound I Phosphate Form XIII, which is a channel solvate. Compound I Phosphate Form XII (wet) could be a hydrate or solvate, and converts to an isostructural hydrate after drying at ambient conditions.

TABLE 3

Crystalline forms of Compound I Phosphate

| Wet Form | Solvent | Form Classification | Drying conditions | Form after drying | Form Classification after drying | Amount of $H_3PO_4$ by IC |
|---|---|---|---|---|---|---|
| VII | Water (24 h); EtOH/water (1:3) | Hydrated | Vacuum at RT; or at 45° C. | VIII | Hydrate (~3 eq. of water) | 3-3.5 eq. |
| | | | Air dried | IX | Hydrate (~7 eq. of water) | — |
| X | 0.9 water activity; water (2 weeks) | Hydrated | Vacuum at 45° C.; or air dried | XI | Hydrate (~4.4 eq. of water) | 2-2.5 eq. |
| XII | MeOH | Possible Hydrate or solvate | Air dried | XII | Hydrate (2-3 eq. of water) Note: no residual | ~3 eq. |

TABLE 3-continued

Crystalline forms of Compound I Phosphate

| Wet Form | Solvent | Form Classification | Drying conditions | Form after drying | Form Classification after drying | Amount of $H_3PO_4$ by IC |
|---|---|---|---|---|---|---|
| XIII | Acetone, MEK | Possible channel solvate | Air dried | VIII | MeOH by NMR Hydrate (~3 eq. of water) | — |
| XIV | Acetone/water (10:1); 2-MeTHF/MeOH/water (10:1:1); IPA/MeOH/water (10:1:1) | Possible Hydrate | Air dried | XIV | Hydrate (~3 eq. of water) | ~2.5 eq. |
| XV | EtOH | Possible hydrate or solvate | Air dried | VIII | Hydrate (~3 eq. of water) | 3-3.5 eq. |

2.2.1 Compound I Phosphate Form VII

The XRPD analysis of Compound I Phosphate Form VII was performed on the wet solids obtained from EtOH/water (1:3) using the following experimental setting: 45 kV, 40 mA, K$\alpha$1=1.5406 Å, scan range 2-40°, step size 0.0167°, counting time: 15.875 s. The characteristic peaks of Compound I Phosphate Form VII include: 7.2, 7.5, 14.6, 19.3, 21.6°2θ (FIG. 20). Compound I Phosphate Form VII converted to Compound I Phosphate Form VIII upon vacuum drying.

2.2.2 Compound I Phosphate Form VIII

The following procedure was used to obtain Compound I Phosphate Form VIII: A solution of Compound I (1.0 g) and 85% phosphoric acid (1.3 g), water (9.0 ml) and ethanol (3.0 ml) was heated to 30° C. and seeded with Compound I Phosphate seeds (5 mg). The mixture was cooled from 30° C. to 0° C. The solids were isolated by filtration, rinsed with a solution of 72.5% water, 19% ethanol and 8.5% phosphoric acid (3×2 ml) and dried to afford Compound I Phosphate Form VIII (1.4 g).

The XRPD analysis of Compound I Phosphate Form VIII was performed for the dry solids using the following experimental setting: 45 kV, 40 mA, K$\alpha$1=1.5406 Å, scan range 2-40°, step size 0.0167°, counting time: 15.875 s. The characteristic peaks of Compound I Phosphate Form VIII include: 4.2, 8.3, 10.1, 11.5, 13.1, 16.0°2θ (FIG. 21).

The DSC analysis was conducted using 2-3 mg of Compound I Phosphate Form VIII sample and at a heating rate of 10° C./min over the range of 20-300° C. (FIG. 22). DSC thermogram showed multiple endothermic events including solvent loss below 100° C. and the melting onset at 181° C.

Figure 23:
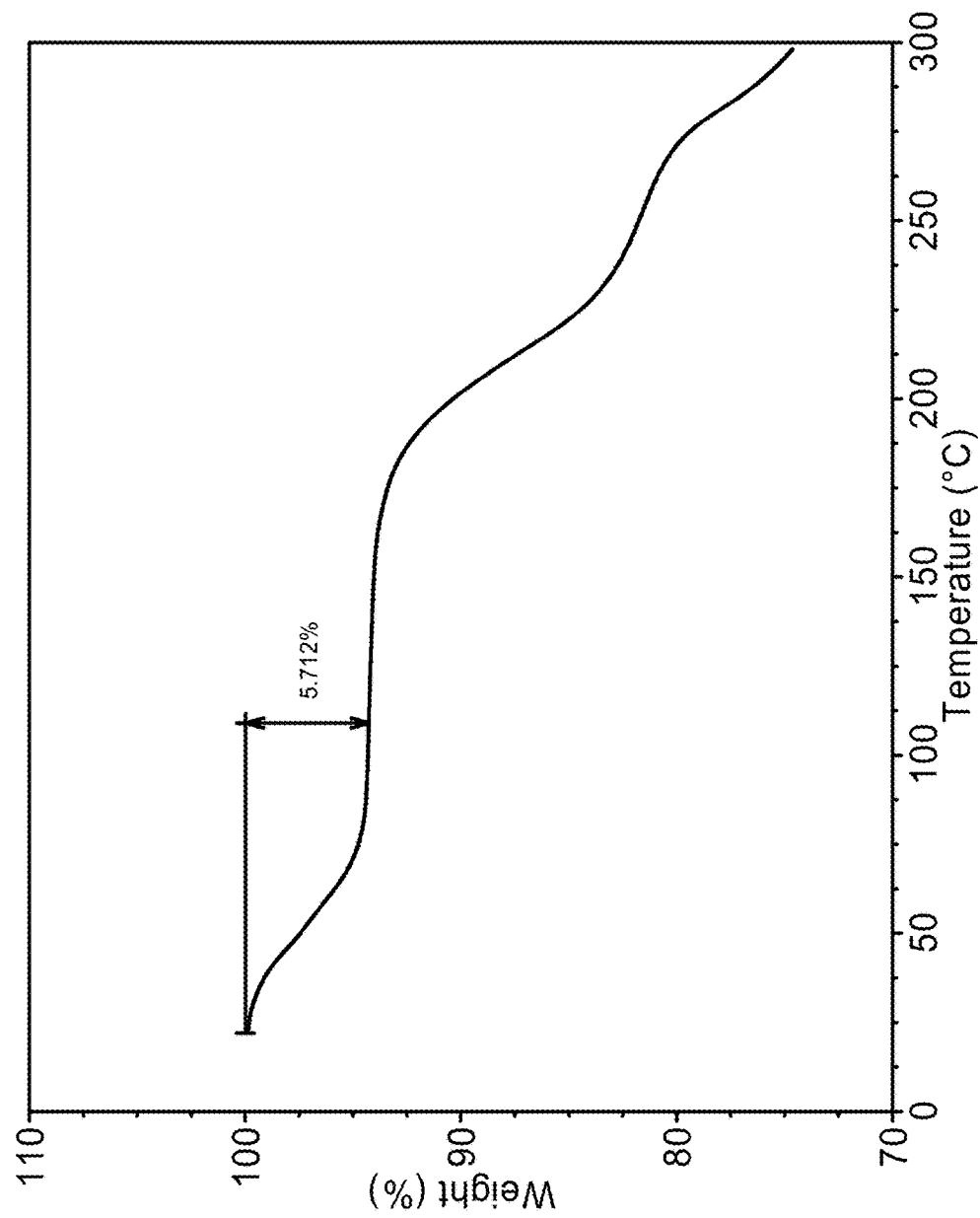
FIG. 23 shows a thermogravimetric analysis (TGA) of Compound I Phosphate Form VIII.

The TGA data were obtained using 2-3 mg Compound I Phosphate Form VIII and at a heating rate of 10° C./min over the range of 20-300° C. (FIG. 23). TGA thermogram of Compound I Phosphate Form VIII showed 5.7% weight loss below 100° C. corresponding to the loss of residual solvent. KF analysis showed 5.4% water content. IC analysis showed 3-3.5 equivalents of phosphoric acid in Compound I Phosphate Form VIII.

2.2.3 Compound I Phosphate Form IX

Compound I Phosphate Form IX was obtained after drying Compound I Phosphate Form VII at ambient conditions. The XRPD analysis of Compound I Phosphate Form IX was performed using the following experimental setting: 45 kV, 40 mA, K$\alpha$1=1.5406 Å, scan range 2-40°, step size 0.0167°, counting time: 15.875 s. The characteristic peaks of Compound I Phosphate Form IX include: 8.4, 10.2, 16.1, 16.3, 20.5, 21.7°2θ (FIG. 24).

The DSC analysis was conducted using 2-3 mg of Compound I Phosphate Form IX sample and at a heating rate of 10° C./min over the range of 20-300° C. (FIG. 25). DSC thermogram showed multiple endothermic events including solvent loss below 150° C. and two broad endotherms with onsets at 177° C. and 204° C.

Figure 26:
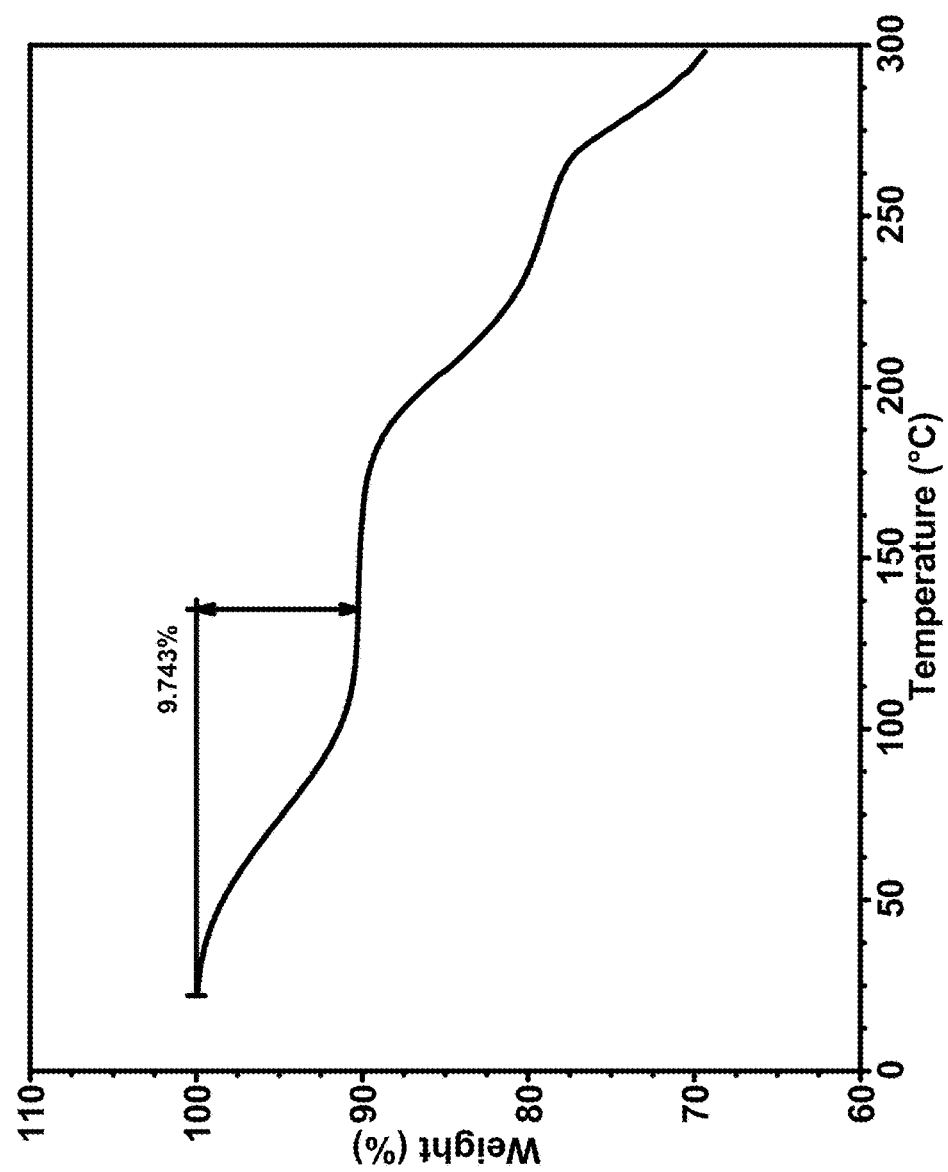
FIG. 26 shows a thermogravimetric analysis (TGA) of Compound I Phosphate Form IX.

The TGA data were obtained using 5-6 mg Compound I Phosphate Form IX and at a heating rate of 10° C./min over the range of 20-300° C. (FIG. 26). TGA thermogram of Compound I Phosphate Form IX showed 9.7% weight loss below 120° C. corresponding to the loss of residual solvent. KF analysis showed about 11.4% water content, corresponding to 6-7 equivalents of water.

2.2.4. Compound I Phosphate Form X

Compound I Phosphate Form X was obtained from 2 weeks slurry of Compound I Phosphate Form VIII in water or EtOH/water mixture of 0.9 water activity (~50 mg of Compound I Phosphate Form VIII in 1 mL of solvent). The XRPD analysis of Compound I Phosphate Form X was performed using the following experimental setting: 45 kV, 40 mA, K$\alpha$1=1.5406 Å, scan range 2-40°, step size 0.0167°, counting time: 15.875 s. The characteristic peaks of Compound I Phosphate Form X include: 3.4, 4.3, 6.6, 9.5, 10.6°2θ (FIG. 27). Compound I Phosphate Form X converted to Compound I Phosphate Form XI upon air or vacuum drying. Compound I Phosphate Form X appears to be a hydrated form.

2.2.5 Compound I Phosphate Form XI

Compound I Phosphate Form XI was obtained after drying of Compound I Phosphate Form X. The XRPD analysis of Compound I Phosphate Form XI was performed using the following experimental setting: 45 kV, 40 mA, K$\alpha$1=1.5406 Å, scan range 2-40°, step size 0.0167°, counting time: 15.875 s. The characteristic peaks of Compound I Phosphate Form XI include: 4.0, 8.9, 13.1, 17.5, 18.1°2θ (FIG. 28).

The DSC analysis was conducted using 2-3 mg of Compound I Phosphate Form XI sample and at a heating rate of 10° C./min over the range of 20-300° C. (FIG. 29). DSC thermogram showed multiple endothermic events including solvent loss below 150° C. and two broad endotherms with onsets at 172° C. and 198° C.

Figure 30:
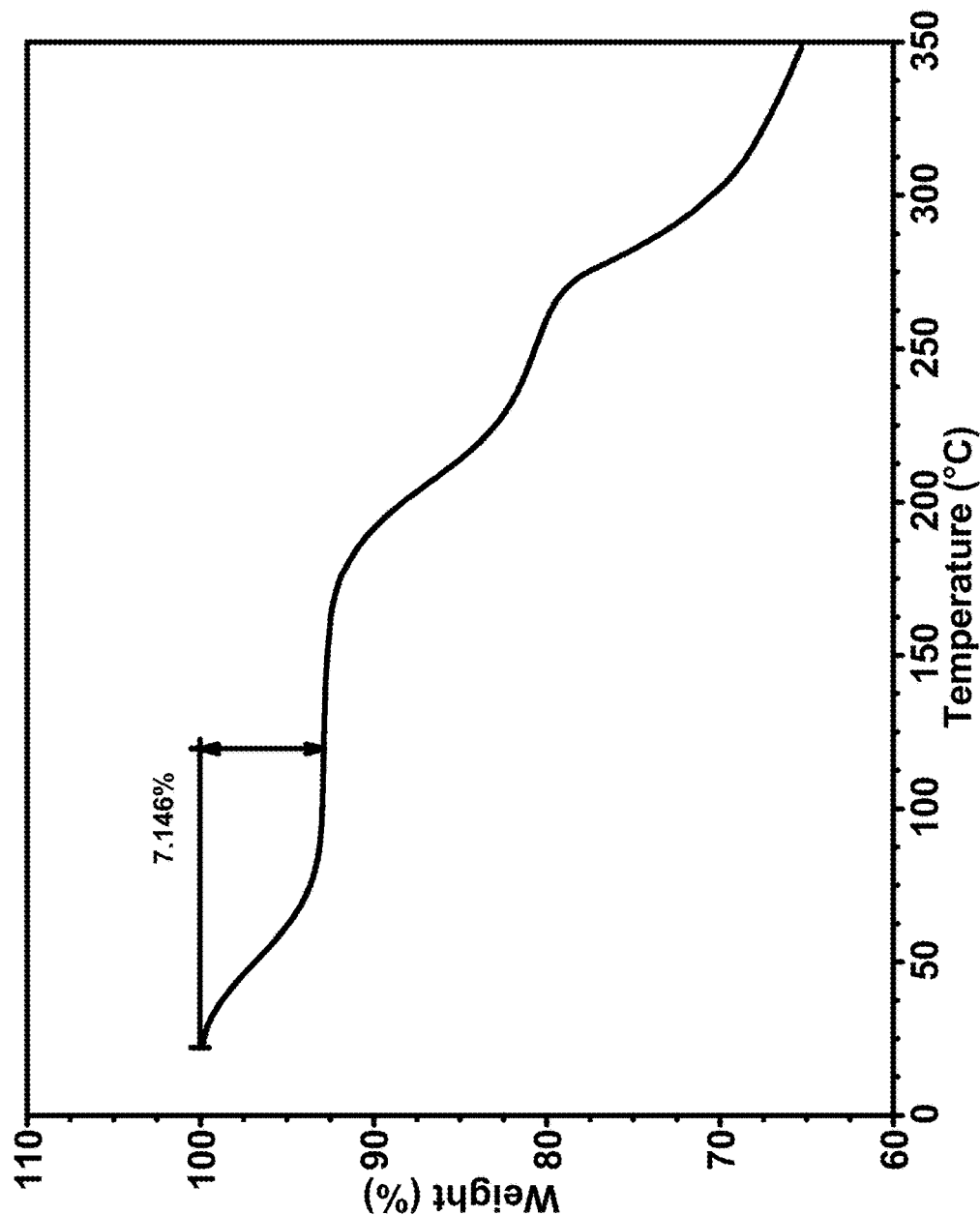
FIG. 30 shows a thermogravimetric analysis (TGA) of Compound I Phosphate Form XI.

The TGA data were obtained using 3-4 mg Compound I Phosphate Form XI and at a heating rate of 10° C./min over the range of 20-300° C. (FIG. 30). TGA thermogram of Compound I Phosphate Form XI showed 7.1% weight loss below 120° C., corresponding to the loss of residual solvent (~4 equivalents of water).

2.2.6 Compound I Phosphate Form XII

Compound I Phosphate Form XII was obtained from the slurry of Compound I Phosphate Form VIII in MeOH (~50 mg of Compound I Phosphate Form VIII in 1 mL of solvent). The XRPD analysis was performed using the following experimental setting: 45 kV, 40 mA, Kα1=1.5406 Å, scan range 2-40°, step size 0.0167°, counting time: 15.875 s. The characteristic peaks of Compound I Phosphate Form XII include: 3.8, 7.5, 8.5, 10.0, 12.4, 16.9°2θ (FIG. 31). No significant changes were observed after drying of Compound I Phosphate Form XII. Compound I Phosphate Form XII appears to be a hydrated form due to 4% water content by KF and no residual MeOH by NMR.

The DSC analysis was conducted using 2-3 mg of Compound I Phosphate Form XII sample and at a heating rate of 10° C./min over the range of 20-300° C. (FIG. 32). DSC thermogram showed multiple endothermic events including solvent loss below 120° C. and two broad endotherms with onset at 191° C. and peaks at 205° C. and 229° C., respectively.

Figure 33:
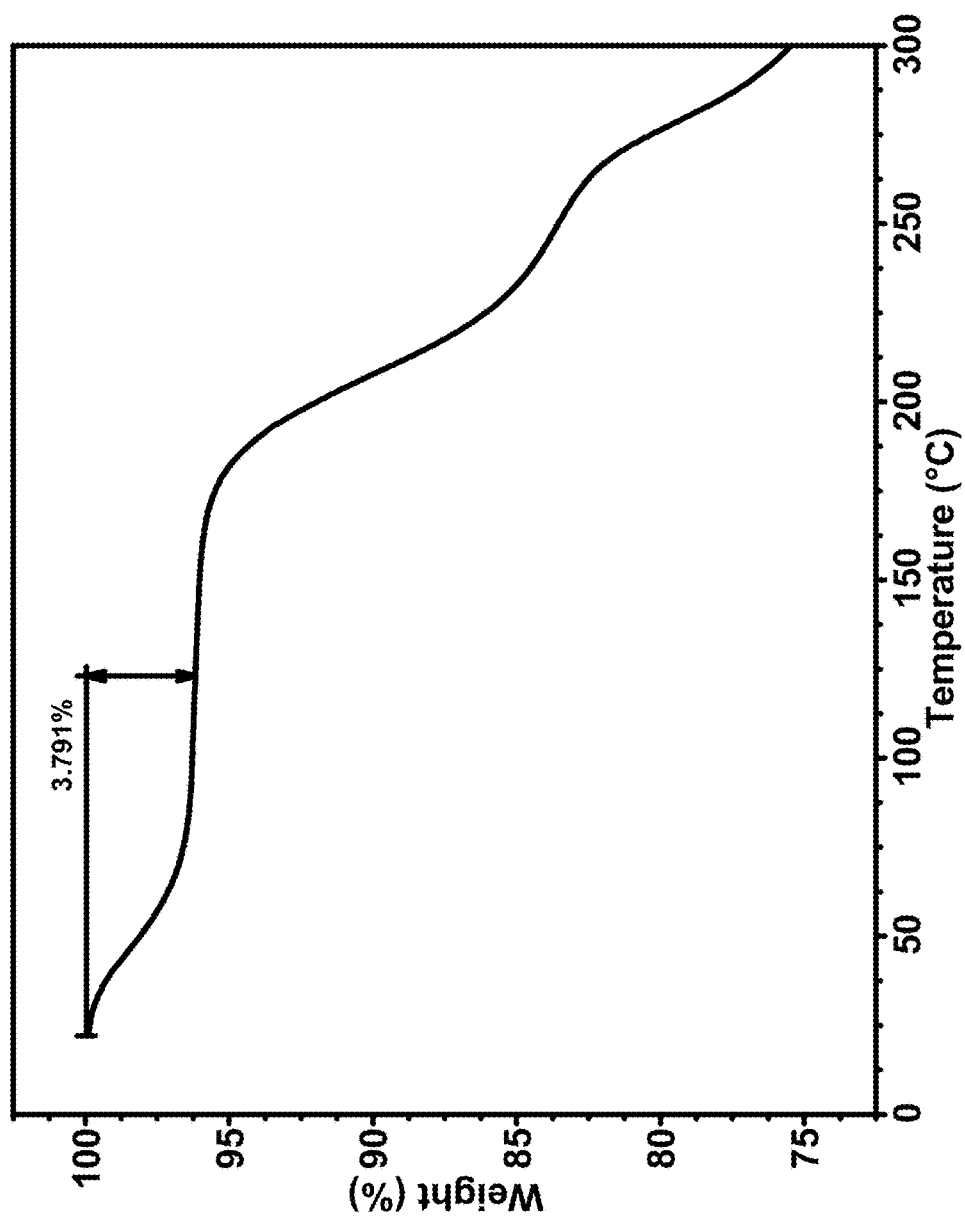
FIG. 33 shows a thermogravimetric analysis (TGA) of Compound I Phosphate Form XII.

The TGA data were obtained using 3-4 mg Compound I Phosphate Form XII and at a heating rate of 10° C./min over the range of 20-300° C. (FIG. 33). TGA thermogram of Compound I Phosphate Form XII showed 3.8% weight loss below 120° C., corresponding to the loss of residual solvent (~2.5 equivalents of water).

2.2.7 Compound I Phosphate Form XIII

Compound I Phosphate Form XIII was obtained from the slurry of Compound I Phosphate Form VIII in acetone or MEK (~50 mg of Compound I Phosphate Form VIII in 1 mL of solvent). The XRPD analysis was performed using the following experimental setting: 45 kV, 40 mA, Kα1=1.5406 Å, scan range 2-40°, step size 0.0167°, counting time: 15.875 s. The characteristic peaks of Compound I Phosphate Form XIII include: 4.1, 7.9, 10.0, 15.9, 17.9, 22.9°2θ (FIG. 34). Compound I Phosphate Form XIII converted to Compound I Phosphate Form VIII upon air drying. Compound I Phosphate Form XIII appears to be a channel solvate.

2.2.8 Compound I Phosphate Form XIV

Compound I Phosphate Form XIV was obtained from the slurry of amorphous phosphate complex in acetone/water (10:1), in 2-MeTHF/MeOH/water (10:1:1), or in IPA/MeOH/water (10:1:1) (~50 mg in ~1 mL of solvent). The XRPD analysis was performed using the following experimental setting: 45 kV, 40 mA, Kα1=1.5406 Å, scan range 2-40°, step size 0.0167°, counting time: 15.875 s. The characteristic peaks of Compound I Phosphate Form XIV include: 3.5 and 6.9°2θ (FIG. 35). Compound I Phosphate Form XIV appears to be a hydrate based on ~4.5% water by KF, which also contains some residual organic solvent.

Figure 36:
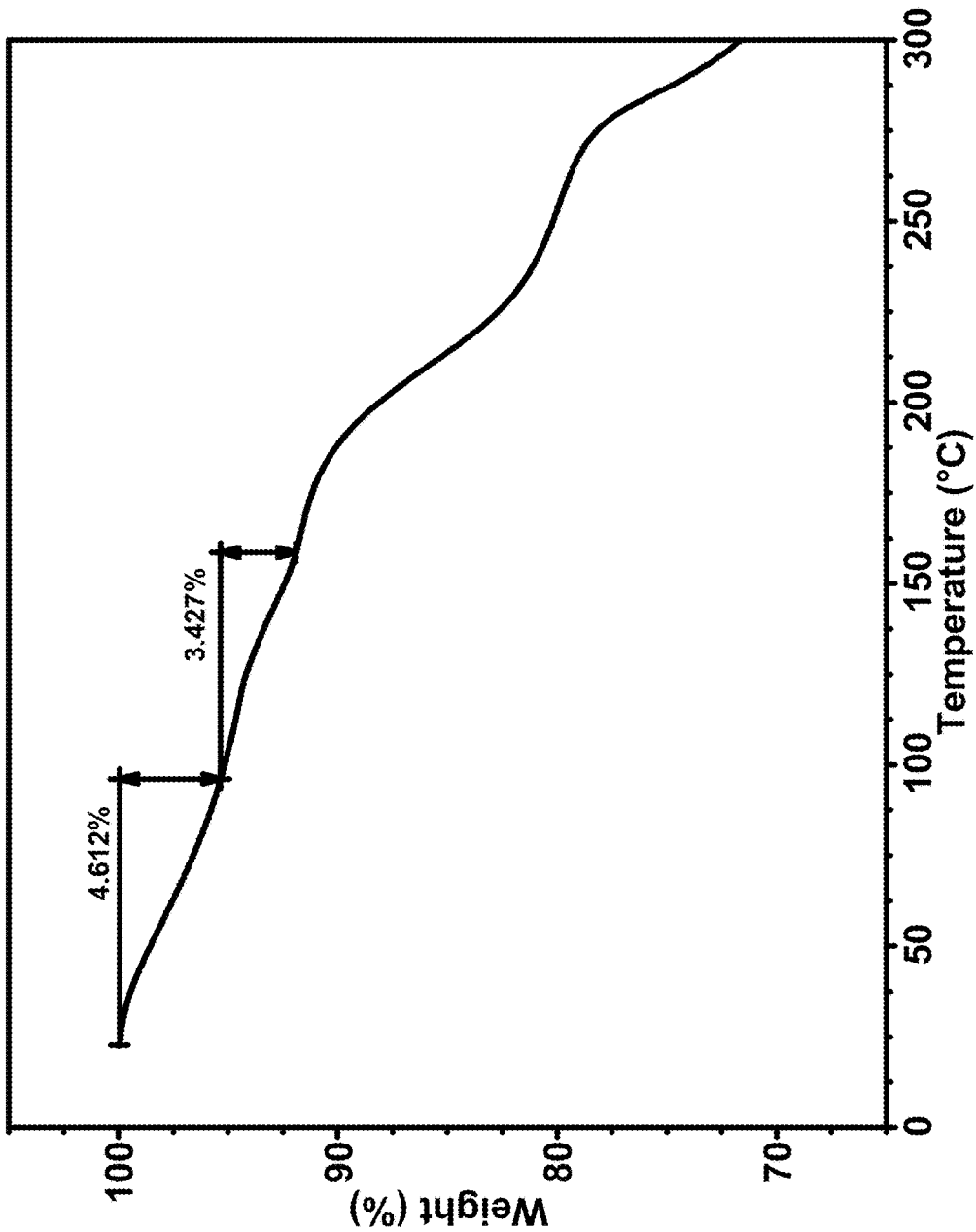
FIG. 36 shows a thermogravimetric analysis (TGA) of Compound I Phosphate Form XIV.

The TGA data were obtained using 3-4 mg Compound I Phosphate Form XIV and at a heating rate of 10° C./min over the range of 20-300° C. (FIG. 36). TGA thermogram of Compound I Phosphate Form XIV showed 4.6% weight loss below 100° C., corresponding to the loss of residual water (~3 equivalents of water), and also 3.4% weight loss at 100-150° C., most likely corresponding to the loss of residual solvent.

2.2.8 Compound I Phosphate Form XIV

Compound I Phosphate Form XIV was obtained using the following procedure: 100 mg Compound I Phosphate Form VIII was dissolved in 950 μL ethanol and 50 μL 85% phosphoric acid at about 50° C. The solution was cooled and stirred at ambient temperature. After 5 days, slurry of Compound I Phosphate Form XIV formed. The XRPD analysis was performed using the following experimental setting: 45 kV, 40 mA, Kα1=1.5406 Å, scan range 2-40°, step size 0.0167°, counting time: 15.875 s. The characteristic peaks of Compound I Phosphate Form XIV include: 4.0, 7.8, 15.9, 23.0, and 24.2°2θ (FIG. 48).

Figure 49:
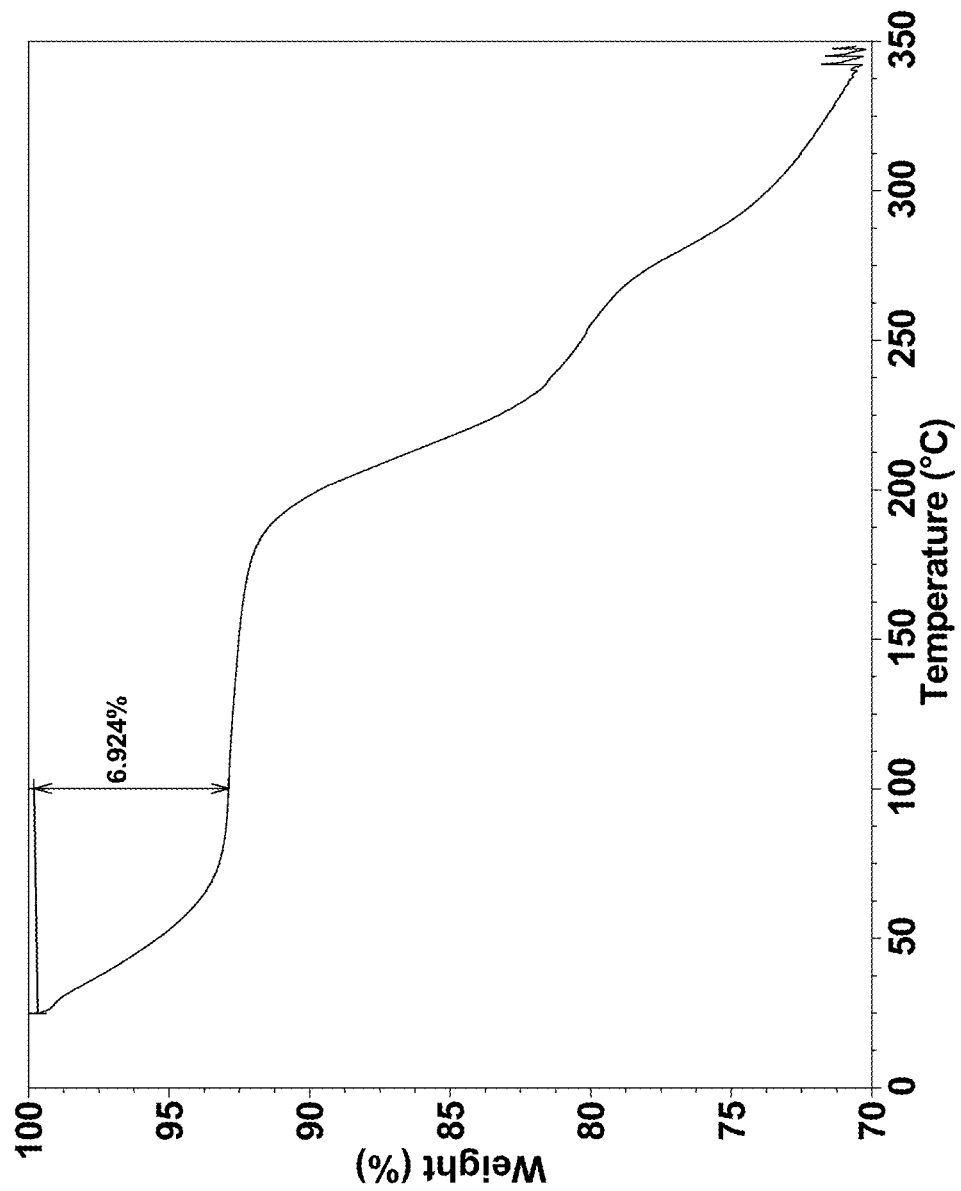
FIG. 49 shows a differential scanning calorimeter (DSC) curve of Compound I Phosphate Form XV.

The TGA data were obtained using 2.3 mg Compound I Phosphate Form XIV and at a heating rate of 10° C./min over the range of 20-350° C. (FIG. 49). TGA thermogram of Compound I Phosphate Form XIV showed about 7% weight loss below 100° C. Compound I Phosphate Form XIV appears to be a solvate.

2.3 Compound I L-tartrate

Crystalline Compound I L-tartrate was obtained using similar conditions as were used for the phosphate complex formation with significant excess of L-tartaric acid (10 equivalents). The dried form was designated as Compound I L-tartrate Form XVI. Compound I L-tartrate Form XVII was observed for the wet solids after stirring Compound I L-tartrate Form XVI in water. Compound I L-tartrate Form XVII converted to Compound I L-tartrate Form XVI upon drying.

2.3.1 Compound I L-tartrate Form XVI

The following procedure was used to obtain Compound I L-tartrate Form XVI: a solution of Compound I (1.0 g) and L-(+)-tartaric acid (1.6 g) in ethanol (10 ml) and water (1.6 ml) at 20° C. was stirred and seeded Compound I L-tartrate seed crystals (5 mg). After stirring for 3 days, the solids were isolated by filtration, rinsed with ethanol (2×1 ml) and dried to afford Compound I L-tartrate Form XVI (0.47 g).

The XRPD analysis of Compound I L-tartrate Form XVI was performed using the following experimental setting: 45 kV, 40 mA, Kα1=1.5406 Å, scan range 2-40°, step size 0.0167°, counting time: 15.875 s. The characteristic peaks of Compound I L-tartrate Form XVI include: 4.1, 8.1, 10.0, 12.9, 14.6, 15.6°2θ (FIG. 37).

The DSC analysis was conducted using 1.4 mg of Compound I L-tartrate Form XVI sample and at a heating rate of 10° C./min over the range of 20-300° C. (FIG. 38). DSC thermogram showed multiple endothermic events including solvent loss below 100° C. and endotherms with onsets at 103, 148 and 178° C., respectively.

Figure 39:
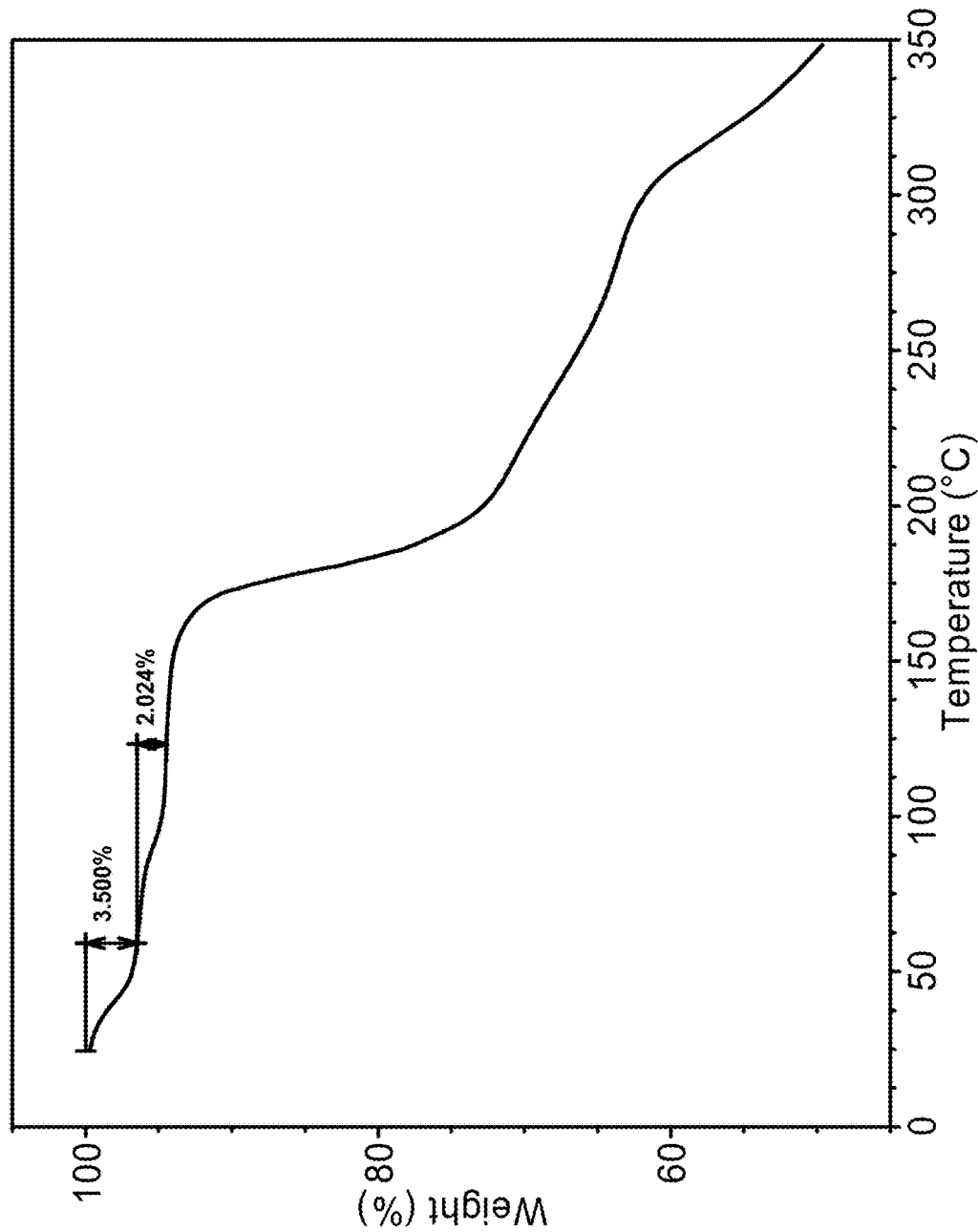
FIG. 39 shows a thermogravimetric analysis (TGA) of Compound I L-tartrate Form XVI.

The TGA data were obtained using 2.2 mg Compound I L-tartrate Form XVI and at a heating rate of 10° C./min over the range of 20-350° C. (FIG. 39). TGA thermogram of Compound I L-tartrate Form XVI showed 3.5% weight loss below 60° C. and 2.0% weight loss at 60-120° C., corresponding to the loss of residual solvents. KF analysis showed 3.1% water content. $^1$H NMR was consistent with structure of Compound I L-tartrate (with 2-3 equivalents of L-tartaric acid) and showed 0.5 equivalents of residual EtOH.

2.3.2 Compound I L-tartrate Form XVII

The XRPD analysis of Compound I L-tartrate Form XVII was performed on wet solids from water slurry using the following experimental setting: 45 kV, 40 mA, Kα1=1.5406 Å, scan range 2-40°, step size 0.0167°, counting time: 15.875 s. The characteristic peaks of Compound I L-tartrate Form XVII include: 4.3, 8.2, 10.1, 15.8, 17.9, 22.6°2θ (FIG. 40). Compound I L-tartrate Form XVII converted to Compound I L-tartrate Form XVI upon air drying.

2.4 Compound I bis-HBr

Since Compound I bis-HCl was found to be crystalline, a similar attempt was carried out to crystallize Compound I bis-HBr. The experiment was carried out by charging 50 mg Compound I and 19 mg HBr (48% solution) in 0.5 ml mixture of MeOH and MTBE. No crystals precipitated after 2 h. After seeding with Compound I HCl Form II, thick slurry was formed after 1 h. XRPD shows that the pattern of precipitated crystalline solids resembles that of Compound I HCl Form II, but they have substantial differences.

2.4.1 Compound I bis-HBr Form XVIII

Crystalline solids of Compound I bis-HBr Form XVIII were analyzed by XRPD, DSC, TGA, KF and IC. The XRPD analysis of Compound I bis-HBr Form XVIII was performed the following experimental setting: 45 kV, 40 mA, Kα1=1.5406 Å, scan range 2-40°, step size 0.0084°, counting time: 8.26 s. The characteristic peaks of Compound I bis-HBr Form XVIII include: 6.7, 7.6, 11.3, 15.1, 18.9, 21.8°2θ (FIG. 41).

The DSC analysis was conducted using 1.9 mg of Compound I bis-HBr Form XVIII sample and at a heating rate of 10° C./min over the range of 20-300° C. (FIG. 42). DSC thermogram showed multiple endothermic events including solvent loss below 100° C. and melting with onset at 203° C.

Figure 43:
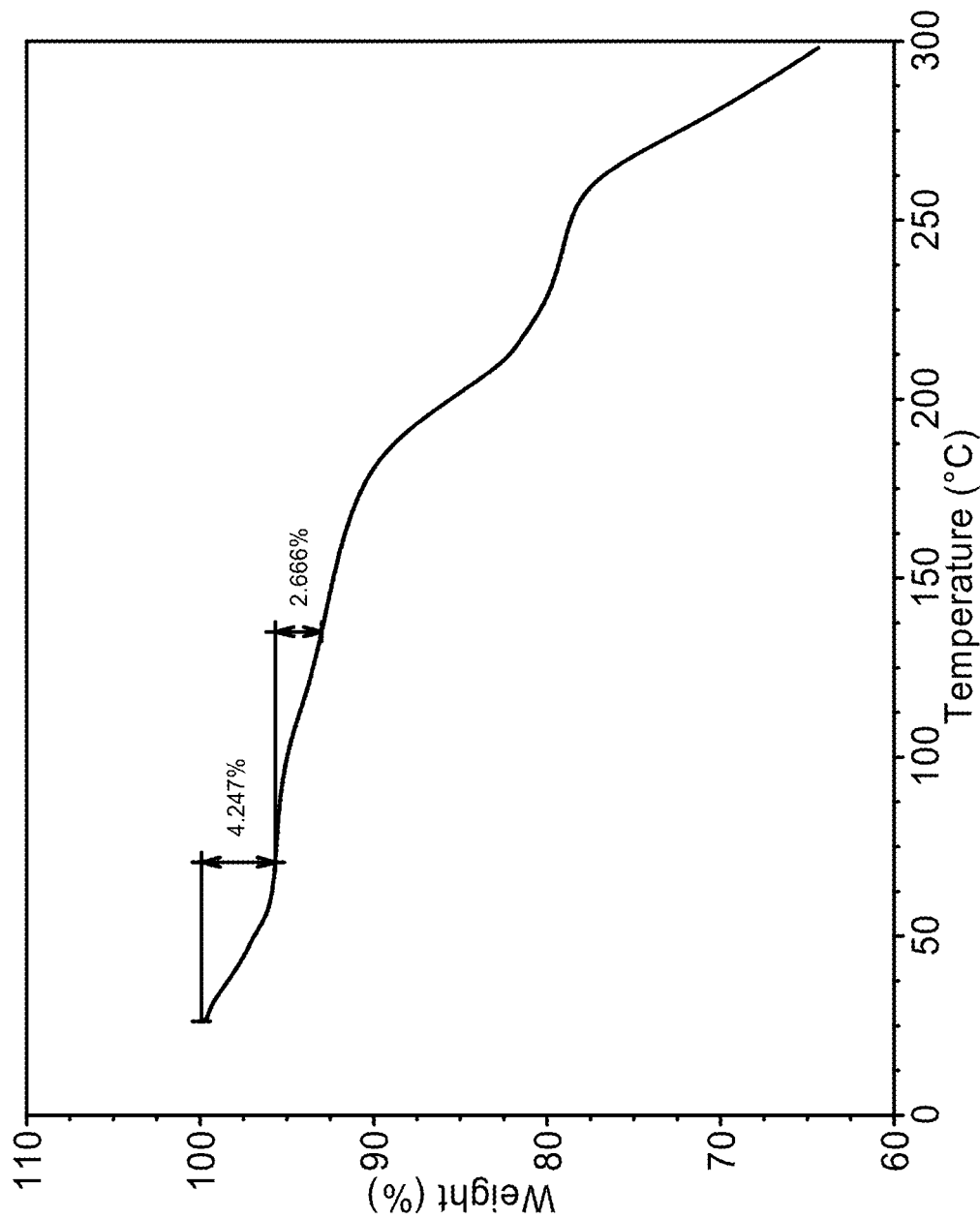
FIG. 43 shows a thermogravimetric analysis (TGA) of Compound I bis-HBr Form XVIII.

The TGA data were obtained using 2.1 mg Compound I bis-HBr Form XVIII and at a heating rate of 10° C./min over the range of 20-300° C. (FIG. 43). TGA thermogram of Compound I bis-HBr Form XVIII showed 4.2% weight loss below 60° C. and 2.7% weight loss at 60-130° C. corresponding to the loss of residual solvents. KF analysis showed 2.5% water content. IC analysis was performed to determine the stoichiometry of the salt and showed about 2 equivalents of HBr.

2.5 Compound I D-Tartrate

Crystalline Compound I D-tartrate was obtained using similar conditions as were used for Compound I L-Tartrate.

An abbreviated screen of Compound I D-tartrate was performed by stirring amorphous Compound I D-tartrate solids in 6 solvents (IPA, EtOAc, acetone, MTBE, THF and toluene) for about 2 weeks at about 21° C. No crystalline solids were obtained.

2.5.1 Compound I D-Tartrate Form I

Figure 50:
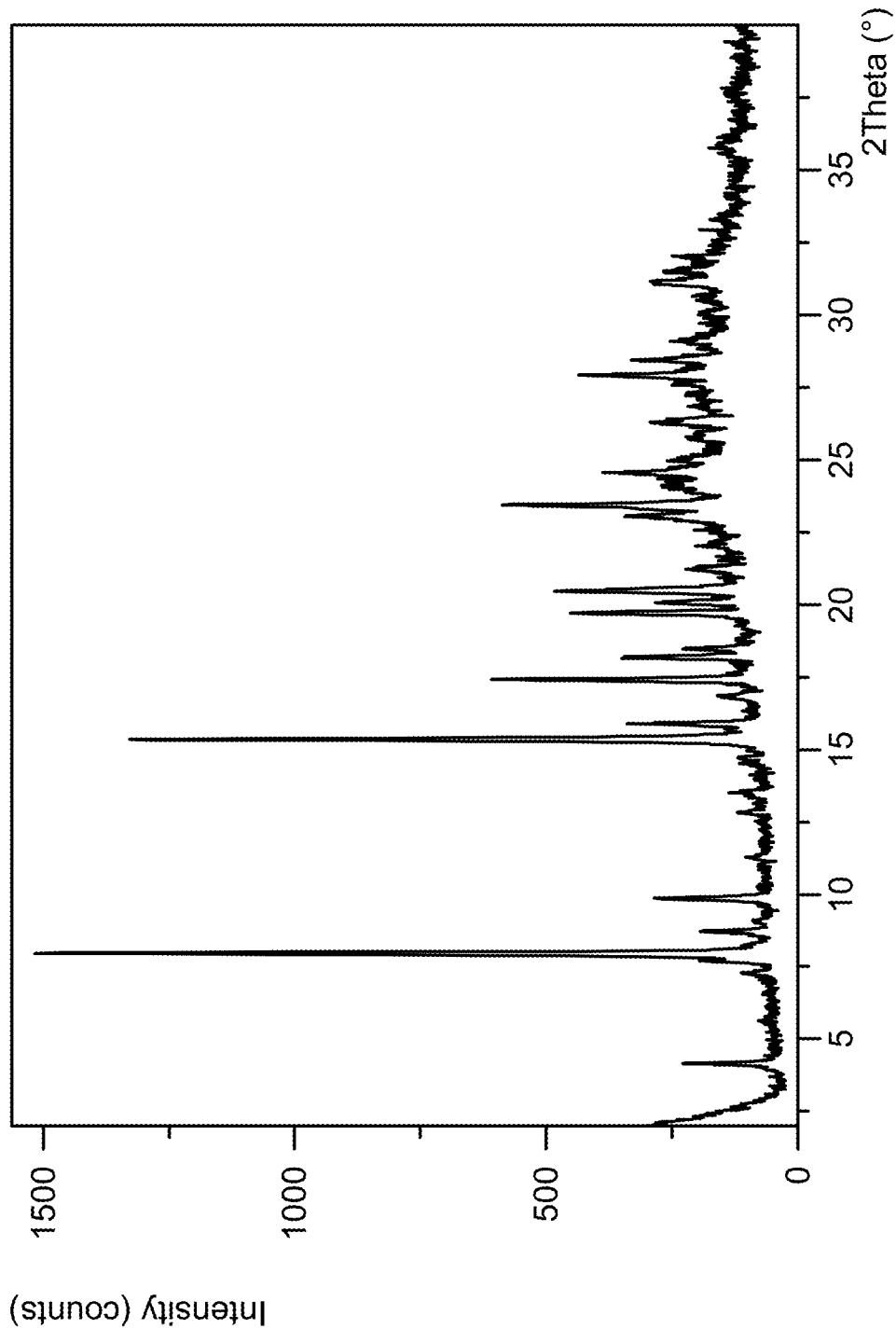
FIG. 50 shows an X-ray powder diffraction (XRPD) of Compound I D-tartrate Form I.

The following procedure was used to obtain Compound I D-tartrate Form I: a solution of Compound I (100 mg) and D-tartaric acid (10 eq.) in ethanol (0.5 mL) and water (0.5 mL) at about 21° C. was stirred for about 2 weeks. An aliquot of the slurry was centrifuged and the wet solids were analyzed by XRPD analysis using the following experimental setting: 45 kV, 40 mA, Kα1=1.5406 Å, scan range 2-40°, step size 0.0084°, and counting time: 8.26 s; which showed characteristic peaks for Compound I D-tartrate Form I at 4.2, 8.0, 9.9, 15.3, and 17.4°2θ (FIG. 50).

2.5.2 Compound I D-Tartrate Form II

Figure 51:
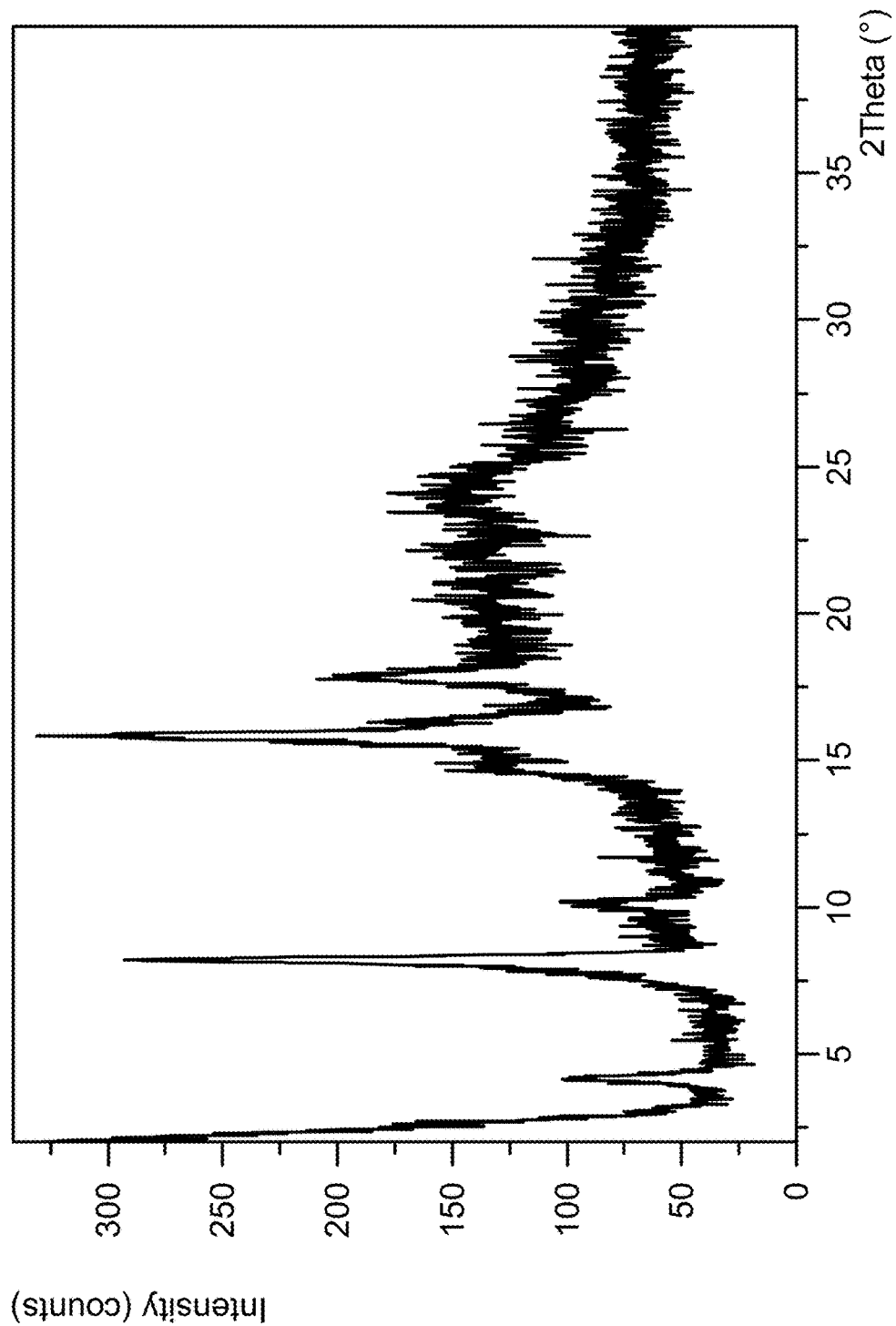
FIG. 51 shows an X-ray powder diffraction (XRPD) of Compound I D-tartrate Form II.

After drying Compound I D-tartrate Form I at about 40° C. under vacuum overnight, Form I became Form II resulting in a different XRPD pattern with characteristic peaks at 4.2, 8.2, 10.1, 15.9, and 17.8°2θ (FIG. 51); based on the following experimental settings: 45 kV, 40 mA, Kα1=1.5406 Å, scan range 2-40°, step size 0.084°, counting time: 8.26 s.

Figure 52A:
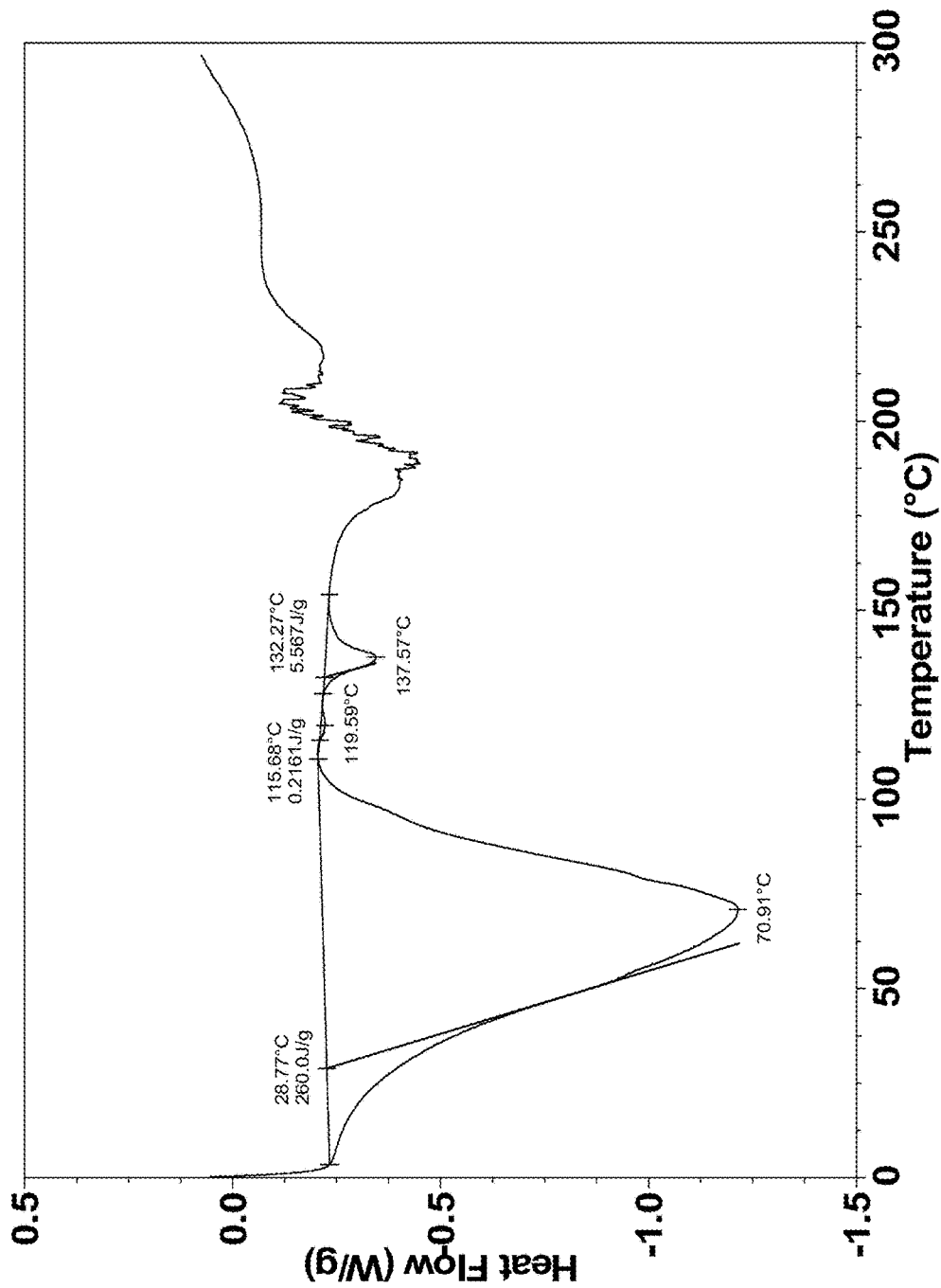
FIG. 52A shows a differential scanning calorimeter (DSC) curve of Compound I D-tartrate Form II.
Figure 52B:
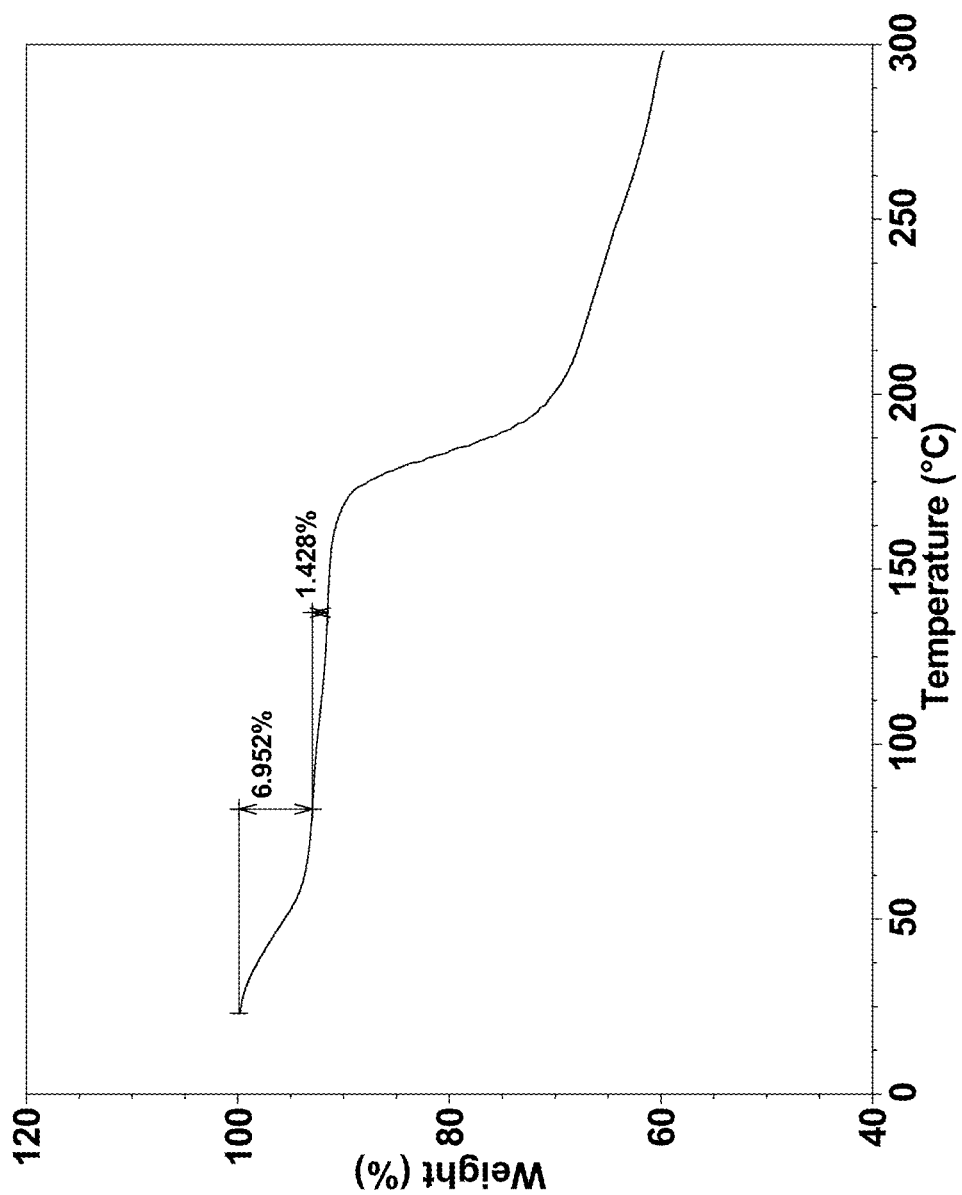
FIG. 52B shows a thermogravimetric analysis (TGA) of Compound I D-tartrate Form II.
Figure 53:
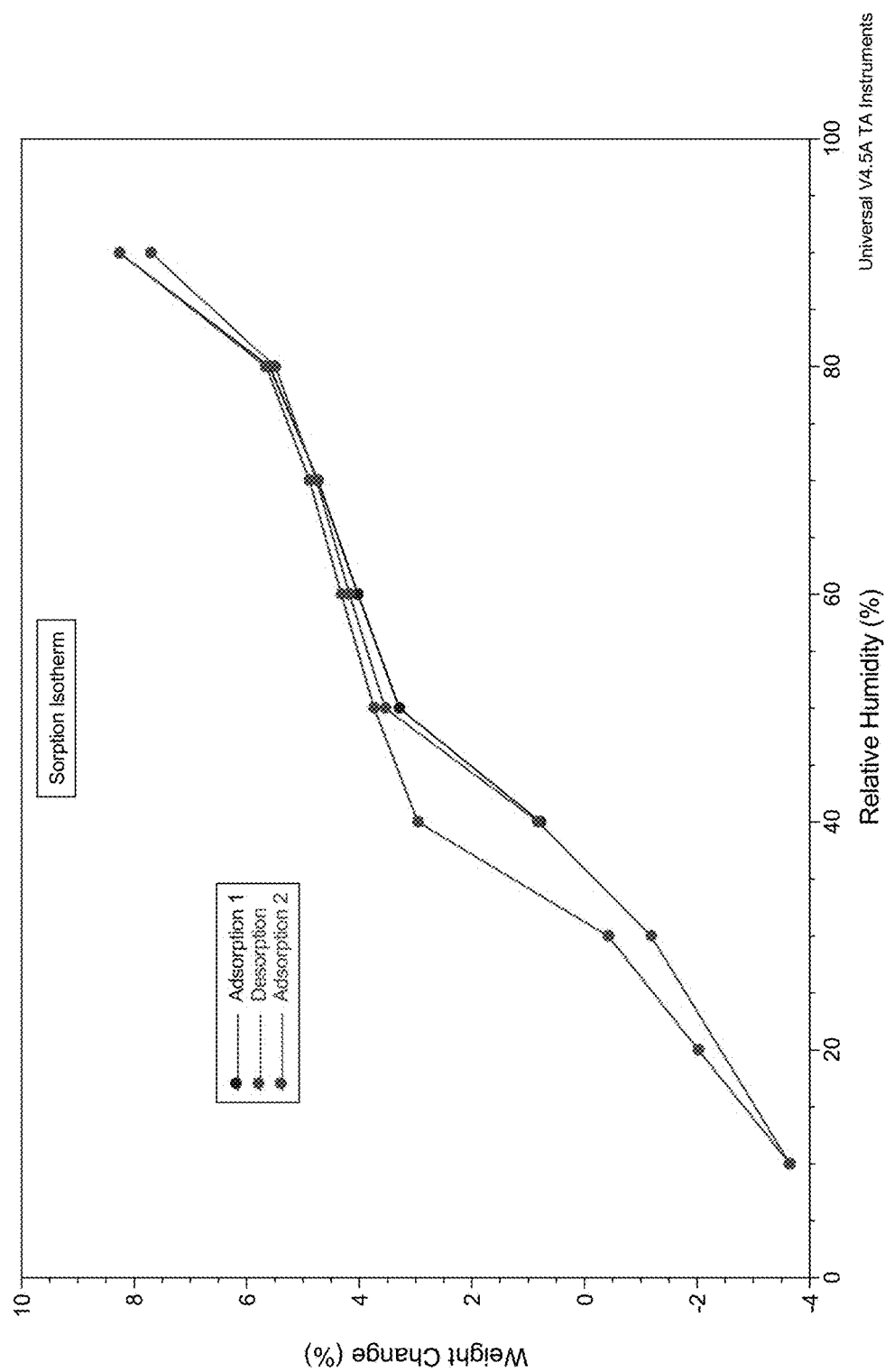
FIG. 53 shows a dynamic vapor sorption (DVS) curve of Compound I D-tartrate Form II.

A DSC analysis was also conducted using 3.06 mg of Compound I D-tartrate Form II at a heating rate of 10° C./min over the range of 25-300° C. which showed endotherms with onsets at about 29, 116, and 132° C.; wherein the first two endothermic events seem to correspond to a two-step weight loss (FIG. 52A). In addition, a TGA thermogram showed that Compound I D-tartrate Form II had a 6.95% weight loss below 80° C. and another 1.4% weight loss between about 80 and 132° C. (FIG. 52B). Considering the significant moisture uptake in the dynamic vapor sorption (DVS) data shown in FIG. 53 between about 10-50% RH (e.g. about 7%), the weight loss indicated in the TGA thermogram was most likely caused by a loss of water.

The invention claimed is:

1. Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form VIII) characterized by an X-ray powder diffractogram comprising the following peaks: 4.2, 8.3, and 16.0° 2θ±0.2° 2θ, as determined on a diffractometer using Cu-Kα radiation at a wavelength of 1.5406 Å.

2. Compound I Phosphate Form VIII according to claim 1, wherein the diffractogram further comprises peaks at 10.1, 11.5, and 13.1° 2θ±0.2° 2θ.

3. Compound I Phosphate Form VIII according to claim 1, wherein the diffractogram is substantially as shown in FIG. 21.

4. Compound I Phosphate Form VIII according to claim 1, characterized by a differential scanning calorimetry (DSC) curve that comprises an endotherm at about 181° C.

5. Compound I Phosphate Form VIII according to claim 4, wherein the DSC curve is substantially as shown in FIG. 22.

6. Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form IX) characterized by an X-ray powder diffractogram comprising the following peaks: 8.4, 16.1, and 16.3° 2θ±0.2° 2θ, as determined on a diffractometer using Cu-Kα radiation at a wavelength of 1.5406 Å.

7. Compound I Phosphate Form IX according to claim 6, wherein the diffractogram further comprises peaks at 10.2, 20.5, and 21.7° 2θ±0.2° 2θ.

8. Compound I Phosphate Form IX according to claim 6, wherein the diffractogram is substantially as shown in FIG. 24.

9. Compound I Phosphate Form IX according to claim 6, characterized by a differential scanning calorimetry (DSC) curve that comprises an endotherm at about 177° C. and an endotherm at about 204° C.

10. Compound I Phosphate Form IX according to claim 9, wherein the DSC curve is substantially as shown in FIG. 25.

11. Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XI) characterized by an X-ray powder diffractogram comprising the following peaks: 8.9, 13.1, and 18.1° 2θ±0.2° 2θ, as determined on a diffractometer using Cu-Kα radiation at a wavelength of 1.5406 Å.

12. Compound I Phosphate Form XI according to claim 11, wherein the diffractogram further comprises peaks at 4.0 and 17.5° 2θ±0.2° 2θ.

13. Compound I Phosphate Form XI according to claim 11, wherein the diffractogram is substantially as shown in FIG. 28.

14. Compound I Phosphate Form XI according to claim 11, characterized by a differential scanning calorimetry (DSC) curve that comprises an endotherm at about 172° C. and an endotherm at about 198° C.

15. Compound I Phosphate Form XI according to claim 14, wherein the DSC curve is substantially as shown in FIG. 29.

16. Crystalline methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate phosphate (Compound I Phosphate Form XII) characterized by an X-ray powder diffractogram comprising the following peaks: 3.8, 7.5, and 16.9° 2θ±0.2° 2θ, as determined on a diffractometer using Cu-Kα radiation at a wavelength of 1.5406 Å.

17. Compound I Phosphate Form XII according to claim 16, wherein the diffractogram further comprises peaks at 8.5, 10.0, and 12.4° 2θ±0.2° 2θ.

18. Compound I Phosphate Form XII according to claim 16, wherein the diffractogram is substantially as shown in FIG. 31.

19. Compound I Phosphate Form XII according to claim 16, characterized by a differential scanning calorimetry (DSC) curve that comprises an endotherm at about 205° C. and an endotherm at about 229° C.

20. Compound I Phosphate Form XII according to claim 16, wherein the DSC curve is substantially as shown in FIG. 32.

* * * * *